(12) United States Patent
Abbott et al.

(10) Patent No.: US 6,284,197 B1
(45) Date of Patent: Sep. 4, 2001

(54) OPTICAL AMPLIFICATION OF MOLECULAR INTERACTIONS USING LIQUID CRYSTALS

(75) Inventors: Nicholas L. Abbott, Davis; Justin J. Skaife, Lafayette, both of CA (US); Vinay K. Gupta, Urbana, IL (US); Timothy B. Dubrovsky, Flemington, NJ (US); Rahul Shah, Davis, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 09/127,382

(22) Filed: Jul. 31, 1998

Related U.S. Application Data

(63) Continuation of application No. 09/092,453, filed on Jun. 5, 1998, now abandoned.

(51) Int. Cl.[7] .......................... G01N 33/53; G01N 27/00
(52) U.S. Cl. .......................... 422/82.05; 422/55; 422/57; 422/68.01; 422/82.01; 435/4; 435/7.1; 435/7.4; 435/7.5; 436/4; 436/501; 436/524; 436/528; 436/805
(58) Field of Search ..................... 422/55, 57, 68.1, 422/82.01, 82.05, 83; 435/4, 7.1, 7.4, 7.5; 436/4, 501, 524, 528, 805

(56) References Cited

U.S. PATENT DOCUMENTS

| | | | |
|---|---|---|---|
| 4,513,034 | 4/1985 | Sparer et al. | 428/1 |
| 4,597,942 | * 7/1986 | Meathrel | 422/57 |
| 4,902,106 | 2/1990 | Dijon et al. | 350/350 |
| 5,071,526 | 12/1991 | Pletcher et al. | |
| 5,130,828 | 7/1992 | Fergason | |
| 5,156,810 | * 10/1992 | Ribi | 422/82.01 |
| 5,451,683 | * 9/1995 | Barrett et al. | 548/302.7 |
| 5,618,493 | 4/1997 | Goldstein et al. | |
| 5,620,850 | * 4/1997 | Bamdad et al. | 530/300 |
| 5,658,491 | 8/1997 | Kistner et al. | 252/299.01 |
| 5,677,195 | 10/1997 | Winkler et al. | 436/518 |

FOREIGN PATENT DOCUMENTS

| | | |
|---|---|---|
| WO 94/03496 | 2/1994 | (WO) . |
| WO 97/32202 | 9/1997 | (WO) . |
| WO 97/33737 | 9/1997 | (WO) . |
| WO 97/35198 | 9/1997 | (WO) . |
| WO 98/04652 | 2/1998 | (WO) . |

OTHER PUBLICATIONS

Bladek, New Method of Visualizing THin Layer Chrtomatograms by Using Liquid Crystals, Journal of Chromat., v. 405, pp. 203–211, 1987.*
Dubois et al., Synthesis, Structure . . . , Annu. Rev. Phys. Chem., v. 43, p. 437, 1992.*
Drawhorn et al., Anchoring of Nematic . . . , J. Phys. Chem., v.99, 16511–16515, 1995.*
Gupta et al., Optical Binding of Ligand Receptor Binding Using Liquid Crystals, Science, v. 279, 2077–2080, 1998.*
Jerome and Shen, Anchoring of nematic . . . , Phys. Rev. E, v.48, 4556–4574, 1993.*
Bladek, Parameters of the Liquid Crystal Method of Visualizing Thin Layer Chromatograms, Journal of Chromatography, v.437, 131–137, 1988.*
Yang et al., Binary Self Assembled Monolayers, Microchemistry: Spectroscopy and Chemistry in Small Domains, Masahura et al. (edrs), North Holland, Amsterdam, 441–454, 1994.*
Jerome, Rep. Prog. Phys., v. 54, 391–451, 1991.*
Gupta et al., "Optical Amplification of Ligand–Receptor Binding Using Liquid Crystals," Science, 279:2077–2080 (1998).
Miller et al., "Planar anchoring of nematic 4–n–pentyl–4'–cyanobiphenyl on self–assembled monolayers formed from alkanethiols on gold," Appl. Phys. Lett., 69(13):1852–1854 (1996).
Lenk et al., "Structural Investigation of Molecular Organization in Self–Assembled Monolayers of a Semifluorinated Amidethiol," Langmuir, 10:4610–4617 (1994).
Poziomek, E.J., et al., "Use of Liquid Crystals as Vapor Detectors," Mol. Cryst. Liq. Cryst., 27:175–185 (1973).
Cognard, J., "Alignment of Nematic Liquid Crystals and Their Mixtures," Mol. Cryst. Liq. Cryst., 1:1–74 (1982).
Xia, Y., et al., "Use of Controlled Reactive Spreading of Liquid Alkanethiol on the Surface of Gold To Modify the Size of Features Produced by Microcontact Printing," J. Am. Chem. Soc., 117:3274–3275 (1995).
Hickman, J.J., et al., "Rational pattern design for in vitro cellular networks using surface photochemistry," J. Vac. Sci. Technol., 12(3):607–16 (1994).
Yang, J.Y., et al., "Binary self–assembled monolayers: spectroscopy and application to liquid crystal alignment," Masuhara et al., Eds,; Microchemistry, North–Holland, Amsterdam, 1994, p. 441.
Gupta, V.K., et al., "Design of Surfaces for Patterned Alignment of Liquid Crystals on Planar and Curved Substrates," Science 276:1533–1536 (1997).
Proust, J.E., et al., "Orientation of a Nematic Liquid Crystal by Suitable Boundary Surfaces," Solid State Commun. 11:1227–1230 (1972).

(List continued on next page.)

Primary Examiner—Bennett Celsa
(74) Attorney, Agent, or Firm—Townsend and Townsend and Crew LLP

(57) ABSTRACT

Interactions between molecules which are components of self-assembled monolayers and other molecules can be amplified and transduced into an optical signal through the use of a mesogenic layer. The invention provides a device and methods for detecting analytes. The device comprises a substrate onto which a self-assembled monolayer is attached and a mesogenic layer which is anchored by the self-assembled monolayer. The mesogenic layer undergoes a change in conformation in response to the molecular interaction.

21 Claims, 25 Drawing Sheets

OTHER PUBLICATIONS

Drawhorn, R.A., et al., "Anchoring of Nematic Liquid Crystals on Self–Assembled Monolayers Formed form Alkanethiols on Semitransparent Films of Gold," *J. Phys. Chem.*, 99(45)11–16515 (1995).

Wagner, P., et al., "Covalent Immobilizaton of Native Biomolecules onto Au (111) via N–Hydroxysuccinimide Ester Functionalized Self–Assembled Monolayers for Scanning Probe Microscopy," *Biophysical Journal*, 70:2052–2066 (1996).

Bain, C.D., et al. "Formation of Monolayers by the Coadsorption of Thiols on Gold: Variation in the Length of the Alkyl Chain," *J. Am. Chem. Soc.*, 111:7164–7175 (1989).

Frey, B.L., et al., "Covalent Attachment and Derivatization of Poly(L–Iysine) Monolayers on Gold Surfaces As Characterized by Polarization–Modulation FT–IR Spectroscopy," *Analytical Chemistry* 68(18):3187–3193 (1996).

Tarlov, M.J., et al., "UV Photopatterning of Alkanethiolate Monolayers Self–Assembled on Gold and Silver," *J. Am. Chem. Soc.*, 115:5305 (1993).

Kumar, A., et al., "Patterned Self–Assembled Monolayers and Meso–Scale Phenomena," *Acc. Chem. Res.*, 28:219–226 (1995).

Jackman, R.J., et al., "Fabrication of Submicrometer Features on Curved Substrates by Microcontact Printing," *Science*, 269:664–665 (1995).

Spinke, J., et al. "Molecular recognition at self–assembled monolayers: Optimization of surface functionalization," *J. Chem. Phys.*, 99(9):7012–7019 (1993).

Charych, D.H., et al., "Direct Colorimetric Detection of a Receptor–Ligand Interaction by a Polymerized Bilayer Assembly," *Science* 261:585–588 (1993).

Charych, D., et al., "A 'litmus test' for molecular recognition using artificial membranes," *Chemistry & Biology* 3(2):113–120 (1996).

Pan, J.J., et al., "Molecular Recognition and Colorimetric Detection of Cholera Toxin by Poly(diacetylene) Liposomes Incorporating $G_{m1}$ Ganglioside," *Langmuir* 13:1365–1367 (1997).

Hiltrop, J.K., et al., "On the Alignment of Thermotropic Nematic and Smectic Liquid Crystals on Lecithin Coated Surfaces," *Ber. Bunsenges. Phys. Chem.*, 98(2):209–213 (1994).

Kim, T., "Polymeric Self–Assembled Monolayers. 5. Synthesis and Characterization of 107 –Functionalized, Self––Assembled Diacetylenic and Polydiacetylenic Monolayers," *Langmuir* 12:6065–6073 (1996).

Mrksich, M, et al., "Using Self–Assembled Monolayers to Understand the Interactions of Man–Made Surfaces with Proteins and Cells," *Annu. Rev. Biophys. Biomol. Struct.*, 25:55–78 (1996).

Jerome, B., "Surface effects and anchoring in liquids crystals," *Rep. Prog. Phys.* 54:391–451 (1991).

Gupta, V.K., et al., "Uniform Anchoring of Nematic Liquid Crystals on Self–Assembled Monolayers Formed from Alkanethiols on Obliquely Deposited Films of Gold," *Langmuir* 12:2587–2593 (1996).

Miller, W., et al., "Comparison of the anchoring of nematic liquid crystals on self–assembled monolayers formed from semifluorinated thiols and alkanethiols," *Liquid Crystals*, 23:175–184.

* cited by examiner

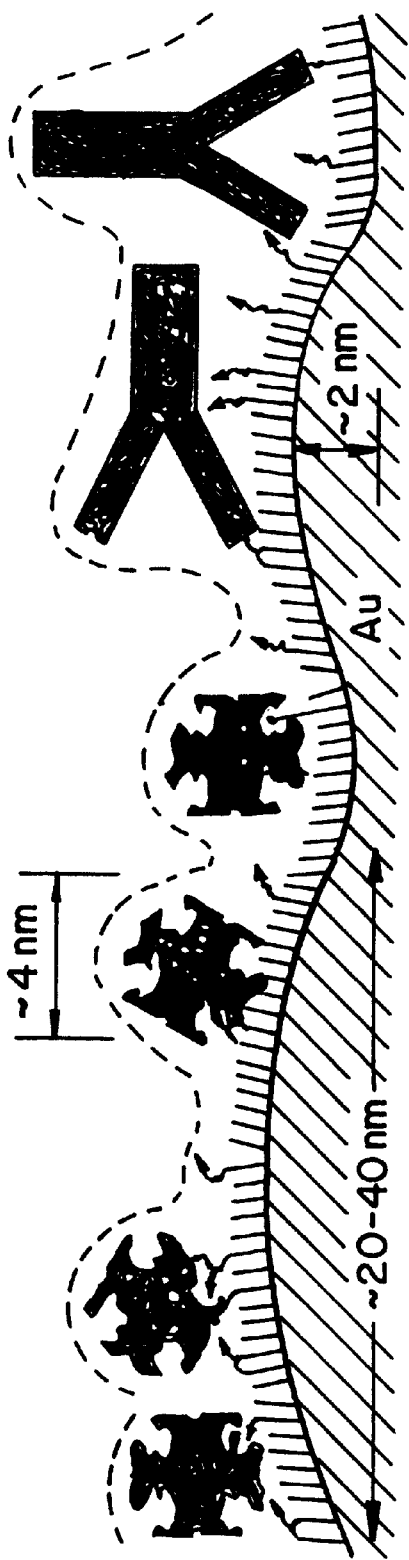
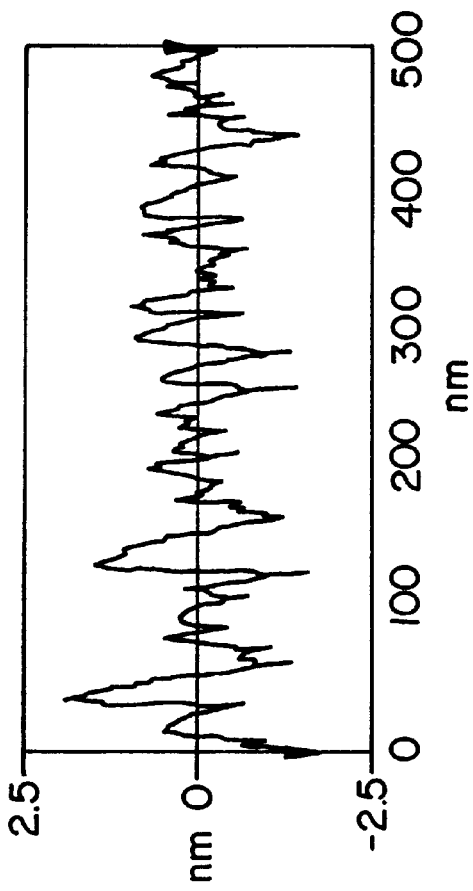
FIG. 1A.
FIG. 1B.

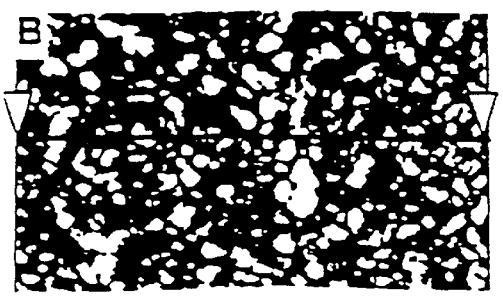
FIG. 1C.
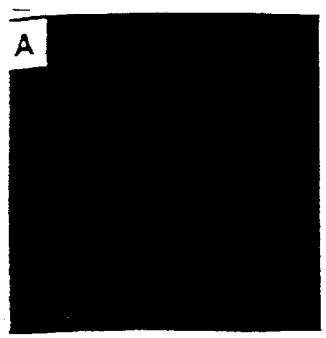  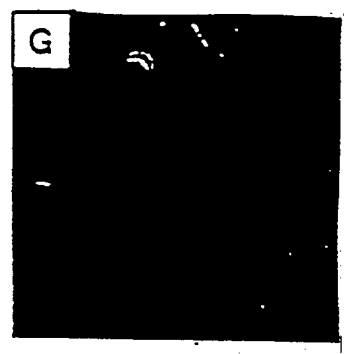
FIG. 3A.    FIG. 3D.    FIG. 3G.
  
FIG. 3B.    FIG. 3E.    FIG. 3H.
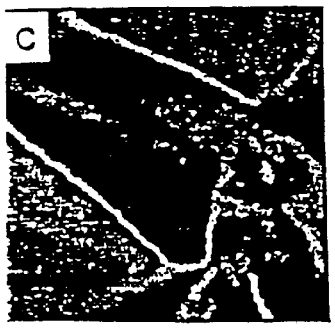 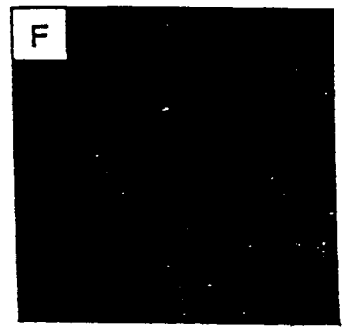 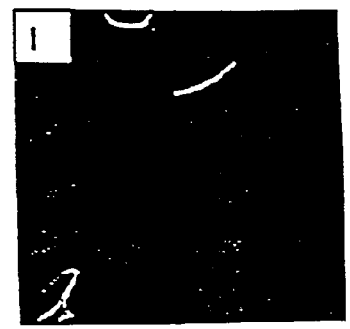
FIG. 3C.    FIG. 3F.    FIG. 3I.

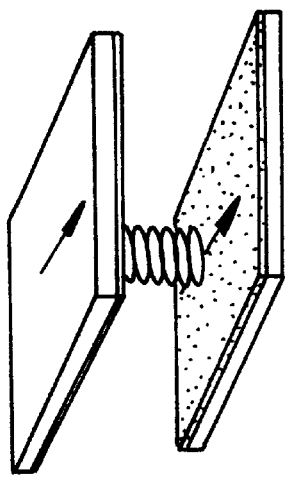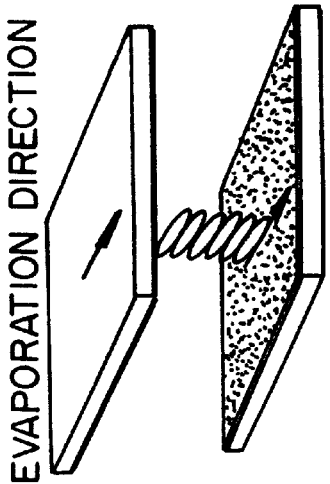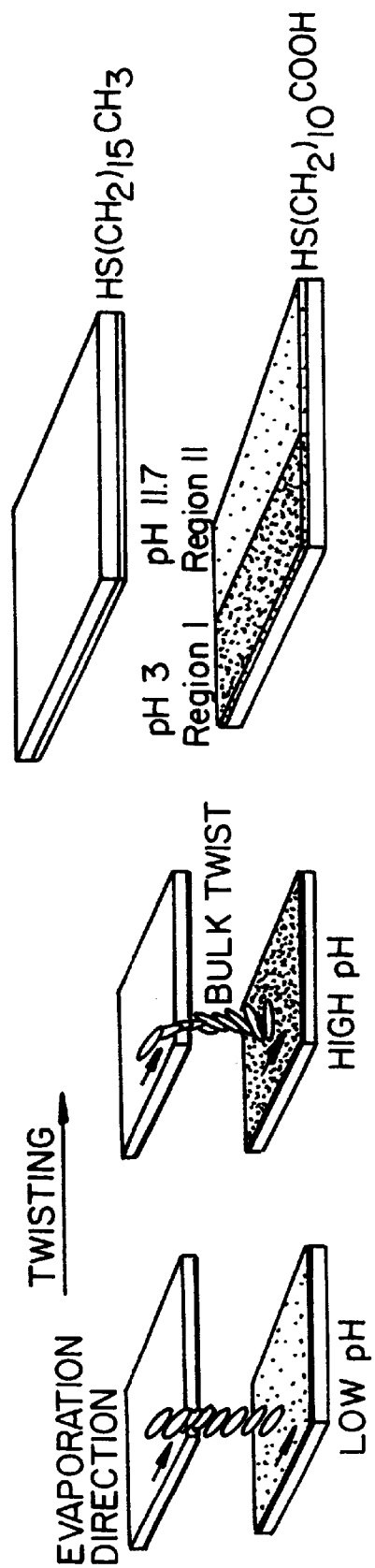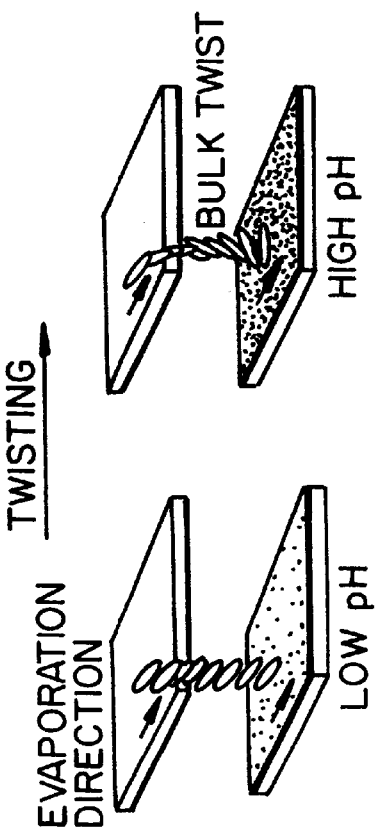

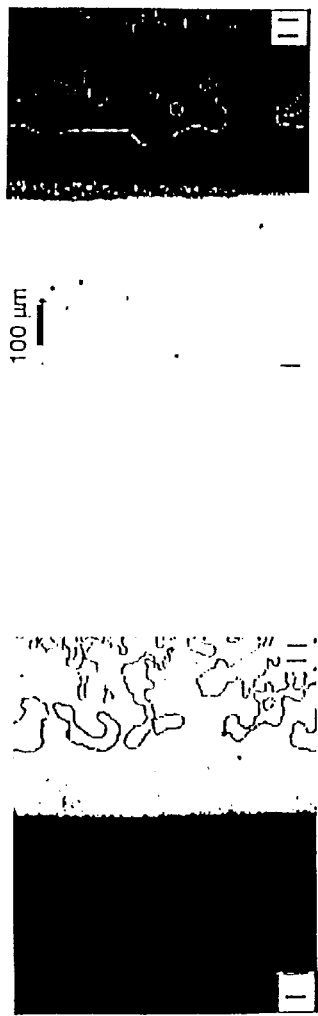
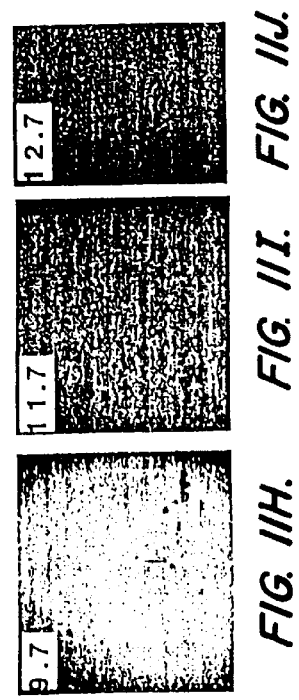
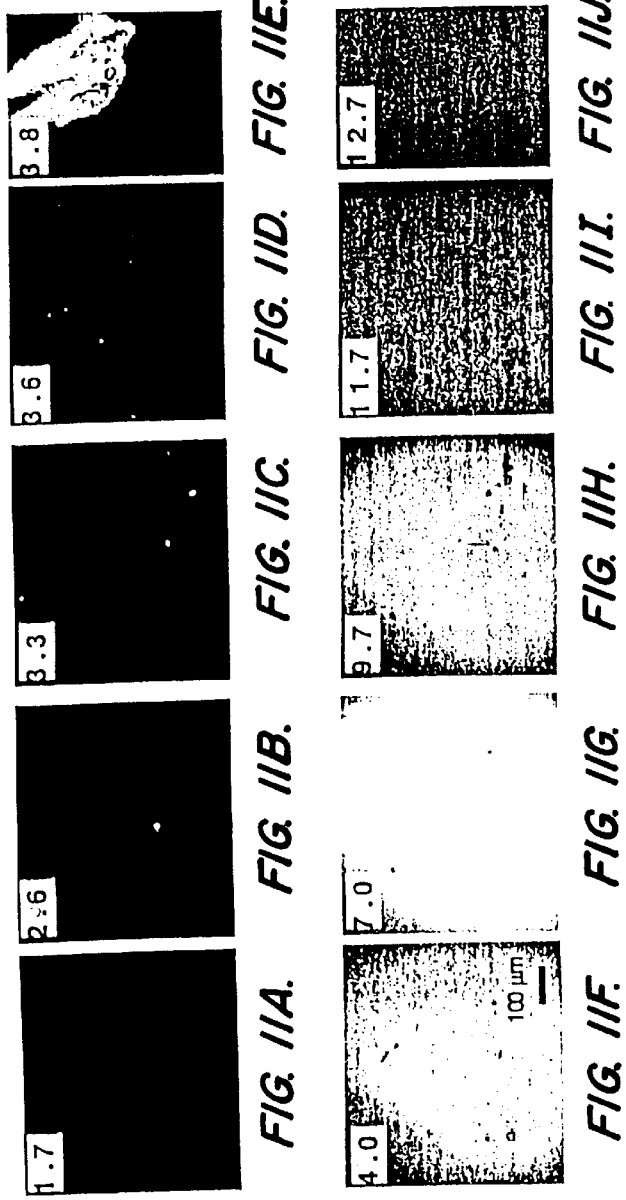
FIG. 10C. FIG. 10D.
FIG. 11A. FIG. 11B. FIG. 11C. FIG. 11D. FIG. 11E.
FIG. 11F. FIG. 11G. FIG. 11H. FIG. 11I. FIG. 11J.

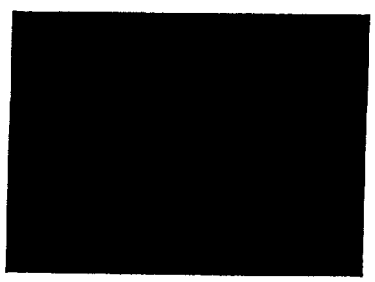
0.01 mM $Cu^{2+}$
FIG. 15A.
0.1 mM $Cu^{2+}$
FIG. 15B.
FIG. 15C.
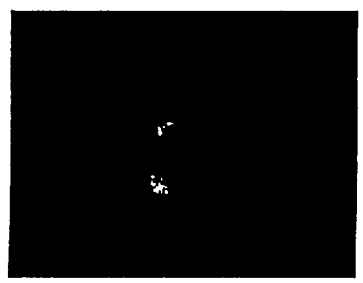
18 mM $Cu^{2+}$
FIG. 15D.
1 mM $Cu^{2+}$
| Contacted in 1 mM $Cu^{2+}$ | No Pretreatment |
FIG. 15E.

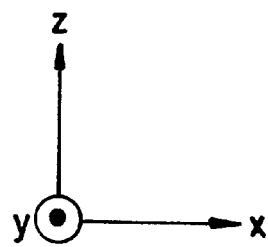
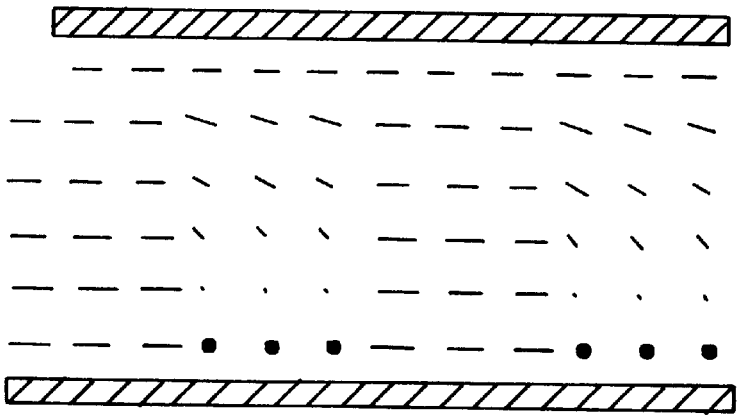
FIG. 16A.
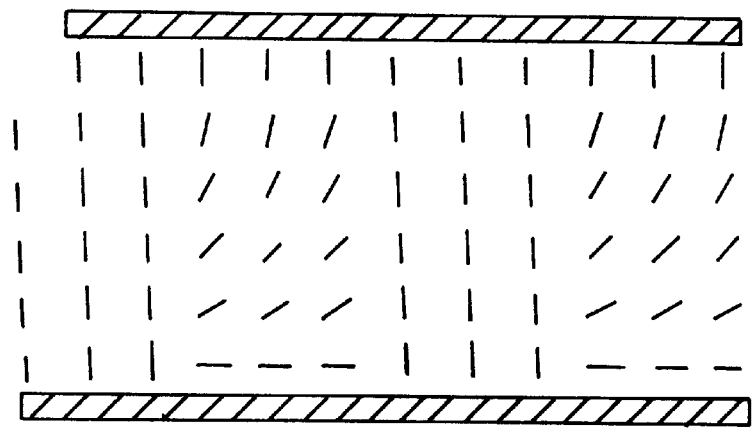
FIG. 16B.
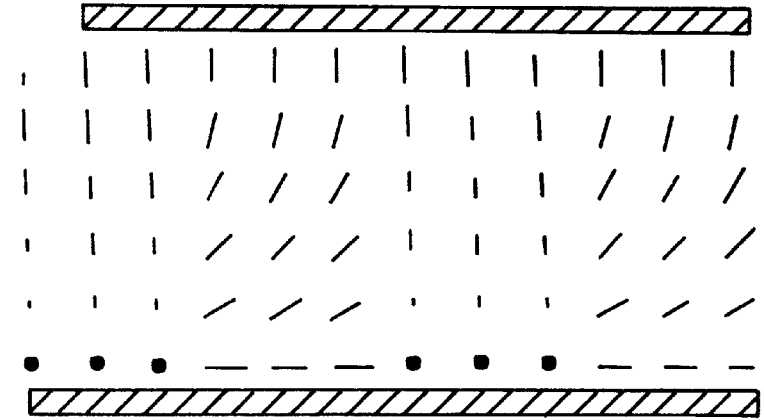
FIG. 16C.

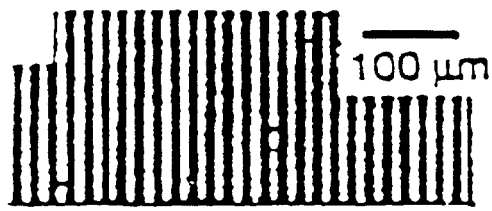 
FIG. 18A.    FIG. 18B.
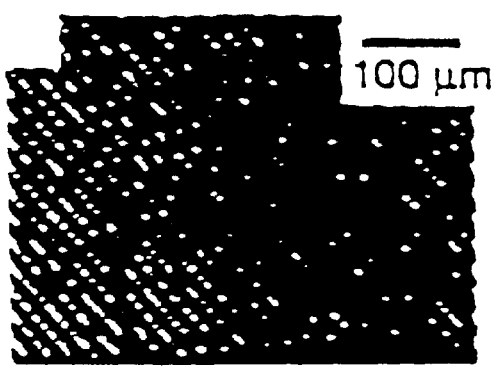 
FIG. 18C.    FIG. 18D.

OPTICAL AMPLIFICATION OF MOLECULAR INTERACTIONS USING LIQUID CRYSTALS

CROSS-REFERENCE TO RELATED APPLICATIONS

This application is a continuation of and claims the benefit of U.S. application Ser. No. 09/092,453, filed Jun. 5, 1998, now abandoned, the disclosure of which is incorporated by reference.

GOVERNMENT RIGHTS

This invention was made with Government support under Grant (or Contract) No. DMR-9400354, CTS 9414147 and CTS 9502263 awarded by the National Science Foundation and Grant No. ONR-N00014-97-10703 awarded by the Office of Naval research. The Government has certain rights in this invention.

FIELD OF THE INVENTION

This invention relates to devices containing liquid crystals which are optionally patterned. Also provided are methods of using these devices as sensors. More particularly, the present invention relates to liquid crystal devices for detecting the interaction an analyte to a recognition moiety that is contained within the device.

BACKGROUND OF THE INVENTION

Liquid crystals possess physical properties which are normally associated with both solids and liquids. Similar to fluids, the molecules in liquid crystals are free to diffuse about, however, a small degree of long range orientational and sometimes positional order is maintained causing the substance to be anisotropic as is typical of solids.

A vast array of organic and metal-containing substances exhibit liquid, crystallinity. A common feature of these molecules is either an elongated or flattened, somewhat inflexible molecular framework which is usually depicted as either cigar- or disk-shaped. The orientational and positional order in a liquid crystal phase is only partial, with the intermolecular forces striking a very delicate balance between attractive and repulsive forces. As a result, liquid crystals display an extraordinary sensitivity to external perturbations (e.g., temperature, pressure, electric and magnetic fields, shearing stress or foreign vapors).

The phenomenon of orientation, or anchoring, of liquid crystals by surfaces has been known nearly as long as have liquid crystals themselves. Anchoring of a liquid crystal by a surface fixes the mean orientation taken by the molecules with respect to the surface. This fixed direction is called the anchoring direction of the liquid crystal. A liquid population of mesogenic molecules can undergo a transition, between two or more anchoring directions, as a result of an external perturbation. Several anchoring transitions have been observed. These transitions involve a change in the orientation of the liquid crystal in the plane of the substrate which can be continuous or discontinuous. The transitions can be induced by a number of different perturbations, including the adsorption of foreign molecules. Such adsorption modifies the interface between the substrate and the liquid crystal, thereby inducing a "switching" between anchoring directions. See, Jerome, B; Shen, Y. R., *Phys. Rev. E,* 48:4556–4574 (1993) and Bechhoefer et al., *Phase Transitions* 33:227–36 (1991).

Past interest in the orientations assumed by liquid crystals near surfaces has been largely driven by their use in electrooptical devices such as flat-panel displays (FPDs). A goal of many studies has, therefore, been the development of methods for the fabrication of surfaces that uniformly orient liquid crystals over large areas. Future uses of liquid crystals in electrooptic devices, in contrast, will rely increasingly on liquid crystals with patterned orientations over small areas (Gibbons et al. *Appl. Phys. Lett.* 65:2542 (1994); Bos et al., *J. Soc. Inf. Disp.* 3–4: 195 (1995); Morris et al., *Emmel, Proc. Soc. Photo-Opt. Instrum. Eng.* 2650, 112 (1996); Mural et al., ibid, 1665:230 (1992); Patel et al., *Opt. Lett.* 16:532 (1991); Zhang et al., *J. Am. Chem. Soc.* 114:1506 (1992); W. P. Parker, *Proc. Soc. Photo-Opt. Instrum. Eng.* 2689:195 (1996)). For example, light can be diffracted or redirected by using patterned mesogenic layer structures that are tuned by application of a uniform electric field (W. P. Parker, *Proc. Soc. Photo-Opt. Instrum. Eng.* 2689:195 (1996)), and FPDs with wide viewing angles and broad gray scales can be fabricated by using pixels that are divided into subpixels, where each sub-pixel is defined by a different orientation of the liquid crystal (Schadt et al., *Nature* 381:212 (1996)). Methods capable of patterning mesogenic layers on curved surfaces are also required for the development of new types of tunable electrooptic mesogenic layer devices, including devices that combine the diffraction of light from the patterned mesogenic layer structure with the refraction of light at the curved surface (Resler et al., *Opt. Lett.* 21:689 (1996); S. M. Ebstein, ibid, p.1454; M. B. Stem, *Microelectron. Eng.* 32:369 (1996): Goto et al., *Jpn. J. Appl. Phys.* 31:1586 (1992); Magiera et al., *Soc. PhotoOpt. Instrum. Eng.,* 2774:204(1996)).

Current procedures for the fabrication of patterned mesogenic layer structures use either spatially nonuniform electric fields from patterned electrodes or patterned "anchoring" surfaces. Fringing of electric fields from patterned electrodes prevents high-resolution patterning of mesogenic layers by this method (Gibbons et al. *Appl. Phys. Lett.* 65:2542 (1994); Williams et al., *Proc. Soc. PhotoOpt. Instrum. Eng.* 1168:352 (1989)).

Patterned anchoring surfaces have been prepared by using mechanical rubbing of spin-coated polymer films, photolithographic masking, and a second rubbing step performed in a direction orthogonal to the first (Patel et al., *Opt. Lett.* 16:532 (1991); W. P. Parker, *Proc. Soc. Photo-Opt. Instrum. Eng.* 2689:195 (1996); Chen et al., *Appl. Phys. Lett.* 67:2588 (1995)). This method of patterning mesogenic layers on surfaces is complex and suffers from the disadvantages of rubbing-based methods, such as the generation of dust and static charge. Recently developed photo-alignment techniques for orienting mesogenic layers provide promising alternatives (Gibbons et al. *Appl. Phys. Lett.* 65:2542 (1994); Schadt et al., *Nature* 381:212 (1996); Chen et al., *Appl. Phys. Lett.* 68:885 (1996); Gibbons et al., *Nature* 351:49 (1991); Gibbons et al., ibid 377:43 (1995); Shannon et al. 368:532 (1994); Ikeda et al., *Science* 268:1873 (1995); Schadt et al., *Jpn. J. Appl. Phys.* 34:3240.(1995)). However, because light-based methods generally require surfaces to be spin-coated by uniformly thin films of photopolymer, and because the orientations of mesogenic layers on photo-aligned surfaces are determined by the angle of incidence of the light used for alignment, these methods are not easily applied to the patterning of mesogenic layers on nonplanar surfaces.

The methods of the present invention permit fabrication of complex mesogenic layer structures in two simple processing steps. Surfaces can be patterned with regions of mesogenic layers that differ in shape and have sizes ranging from micrometers to centimeters. The mesogenic layers can also be patterned on nonplanar surfaces (mesogenic layers have been anchored within pores of alumina and vycor glass coated with surface-active reagents, Crawford. et al. *Phys. Rev. E* 53:3647 (1996), and references therein). The present invention differs from this past work in two principal ways. (i) Scale: Mesogenic layers have been anchored on curved surfaces with radii of curvature that are large compared with the thickness, of the mesogenic layer. The local state of the mesogenic layer is similar to that of mesogenic layers anchored on a planar surface and thus properties of the mesogenic layer are not dominated by elastic energies caused by curvature. Methodologies used for anchoring mesogenic layers on planar surfaces (for example, twisted nematic cells) can be translated to our curved surfaces; and (ii) Patterns: The methods of the invention allow the formation of patterned curved surfaces.

Self-assembled monolayers formed by the chemisorption of alkanethiols on gold are likely to now be the most intensively characterized synthetic organic monolayers prepared to date. See, Ulman, A., 1991, *An Introduction to Ultrathin Organic Films: From Langmuir-Blodgett to Self Assembly* (San Diego, Calif.: Academic Press); Dubois, L. H. et al., 1992, *Annu. Rev. Phys. Chem.,* 43, 437. These monolayers form spontaneously during immersion of evaporated films of gold in solutions of alkanethiols as a result of chemisorption of sulfur on the (111) textured surface of the films. The molecules self-organize into a commensurate _3×_3R30° lattice on the surface of the Au(111). See, "Porter, M. D. 1987, *J. Am. Chem. Soc.,* 109, 3559; Camillone III, N. et al., 1993, *Chem. Phys.,* 98, 3503; Fenter, P. et al., 1994, *Science,* 266, 1216; 20; Chidsey, C. E. D. et al., 1990, *Langmuir,* 6, 682; Sun, F.; Mao, G.; Grainger, D. W. et al., 1994, *Thin Solid Films,* 242, 106. For monolayers formed from $CH_3(CH_2)_nSH$, n>9, at least, the aliphatic chains of the monolayers are extended in the all-trans conformation and tilted approximately 30° from the normal of the surface. Because the spacing between sulfur groups on the _3×3R30° lattice is, on average, 4.9 Å, whereas the van der Waals diameter of an aliphatic chains is, only ~4 Å, the aliphatic chains within these SAMs tilt from the normal so as to come into van der Waals contact and thereby maximize their cohesive dispersive interactions. Studies of the lateral structure within monolayers using X-ray diffraction reveal the existence of domains of size ~100 Å, where each domain has one of six different tilt directions relative to the Au(111) face. See, Fenter, P. et al., 1994, *Science,* 266, 1216.; Recent studies have shown the existence a c(4×2) superlattice, the cause of which remains unresolved.

Surfaces prepared by the chemisorption of organosulfur compounds on evaporated films of gold are not limited to the alkanethiols. Self-assembled monolayers formed from perfluorinated organosulfur compounds have also been reported. See, Lenk, T. J., et al. 1994, *Langmuir,* 10, 4610.; Drawhorn, R. A. et al., 1995, *J. Phys. Chem.,* 99, 16511. These surfaces, too, can be highly ordered, although, interestingly, the origin of the order within the monolayer is largely intramolecular and contrasts, therefore, to monolayers formed from alkanethiols (where the order largely reflects the cohesive intermolecular dispersion force). Steric interactions between adjacent fluorine atoms of a perfluorinated chain cause the chain to twists itself into a rigid, helical conformation. That is, an isolated perfluoro chain is stiff, as compared to an aliphatic chain. Because perfluorinated chains have larger cross-sectional areas than alkanethiols, monolayers formed on gold from perfluorinated thiols are not tilted from the normal to the same degree as alkanethiols. See, Drawhorn, R. A. et al., 1995, *J. Phys. Chem.,* 99, 16511. Estimates by IR studies place the tilt of the perfluorinated chains at 0~10°. Because perfluorinated chains within SAMs on Au(111) are not tilted to the same degree as the alkanethiols, their surfaces are not expected to possess domains formed from regions of monolayer with different tilt directions (as occurs with monolayers formed from alkanethiols). Past reports do not describe the anchoring of liquid crystals on densely-packed monolayers formed from semifluorinated chains. Past investigations on fluorocarbon surfaces have focused on surfaces coated with films of fluorinated polymers such as poly-(tetrafluoroethylene) (Teflon™) and poly-(vinylidene fluoride) (Tedlar™), or fluorine containing surface reagents that pack loosely and host polar/charged groups. See, Cognard, J., 1982, *Mol. Cryst. Liq. Cryst. Supp.,* 78, 1; Uchida, T. et al., 1992, *Liquid Crystals Applications and Uses,* edited by Bahadur, B. (New Jersey: World Scientific), p.2; Hoffman, C. L.; Tsao, M.-W; Rabolt, J. F.; Johnson, H. et al., unpublished results. Due to differences in the method of preparation (e.g., plasma polymerization of teflon vs. sliding contact of a teflon block) results reported in the past for the anchoring of liquid crystals on fluorinated surfaces are variable. In general, however, the fluorocarbon surface, which is a low energy surface, is reported to cause homeotropic anchoring. See, Uchida, T. et al., 1992, *Liquid Crystals Applications and Uses,* edited by Bahadur, B. (New Jersey: World Scientific), p.2.

The use of self-assembled monolayers formed from noon-fluorinated, semifluorinated and perfluorinated organosulfur compounds permits the preparation of well-defined fluorocarbon surfaces for the anchoring mesogenic layers. Mesogenic layers anchored onto these well-defined surfaces are sensitive to perturbations caused from a wide range of sources.

Numerous practical applications of the mesogenic layer's sensitivity to perturbation have been realized. For example, liquid crystals have been used as temperature sensors (U.S. Pat. No. 5,130,828, issued to Fergason on Jul. 14, 1992). Devices containing liquid crystal components have also been used as sensors for indicating the concentration of ethylene oxide in the workplace (U.S. Pat. No. 4,597,942, issued to Meathrel on Jul. 1, 1986). Meathral teaches a device which has an absorbent layer on top of a paper substrate. Neither Meathral not Fergason teach the switchable anchoring of liquid crystals on self-assembled monolayers. Additional information on the use of liquid crystals as vapor sensors is available in Poziomek et al., *Mol. Cryst. Liq. Cryst.,* 27:175–185 (1973).

Liquid crystal devices which undergo anchoring transitions as a result of protein-ligand binding have been reported by Gupta, V. K., Abbott, N. L., *Science* 276:1533–1536 (1998). Switchable liquid crystals supported on self-assembled monolayers were used to detect the binding of avidin and goat-anti-biotin to a biotinylated self-assembled monolayer. Biotin exhibits a very specific, high affinity binding to both avidin (Kd~$10^{-15}$) and anti-biotin (Kd~$10^{-9}$). Gupta et al. teaches the binding of biotin to the self-assembled monolayer and the interaction of this ligand with proteins which are known to display specific and strong binding to biotin.

There is a recognized need in the chemical and pharmaceutical arts for devices having patterned liquid crystals as a component thereof. Further, there is a need for a facile method to produce such patterned liquid crystals. In addition, there is a long recognized need for both methods and devices to detect and characterize analytes in a simple, inexpensive and reliable manner. Even more desirable are systems that can detect the specific interaction of an analyte with another molecule. A device having a detection spatial resolution on approximately the micrometer scale would prove ideal for numerous applications including the synthesis and analysis of combinatorial libraries of compounds. If detecting molecular interactions could be accomplished without the need for prelabeling the analyte with, for example a radiolabel or a fluorescent moiety, this would represent a significant advancement. Quite surprisingly, the present invention provides such devices and methods.

SUMMARY OF THE INVENTION

It has now been discovered that liquid crystals can be used to amplify, and transduce into an optical signal, the interaction of a wide array of molecules with various surfaces. The interaction of the molecule with the surface can be converted into an easily detected optical output.

A variety of surfaces, including spontaneously organized surfaces, can be designed so that molecules, on interacting with these surfaces, trigger changes in the orientations of films of mesogenic compounds. When the molecule interacting with the surface has a size on the order of a protein, the interaction can result in the reorientation of approximately $10^5$–$10^6$ mesogens per molecule. Interaction-induced changes in the intensity of light transmitted through the mesogenic layer can be easily seen with the naked eye.

Thus, in a first aspect, the present invention provides a device comprising: a first substrate having a surface, the surface comprising a recognition moiety; a mesogenic layer oriented on the surface; and an interface between the mesogenic layer and a member selected from the group consisting of gases, liquids, solids and combinations thereof.

In a second aspect, the present invention provides a device comprising: a first substrate having a surface; a second substrate having a surface, the first substrate and the second substrate being aligned such that the surface of the first substrate opposes the surface of the second substrate; a first organic layer attached to the surface of the first substrate, wherein the first organic layer comprises a first recognition moiety; and a mesogenic layer between the first substrate and the second substrate, the mesogenic layer comprising a plurality of mesogenic compounds.

In a third aspect, the present invention provides a device for detecting an interaction between an analyte and a recognition moiety, the device comprising: a first substrate having a surface; a second substrate having a surface, the first substrate and the second substrate being aligned such that the surface of the first substrate opposes the surface of the second substrate; a first organic layer attached to the surface of the first substrate, wherein the organic layer comprises a first recognition moiety which interacts with the analyte; and a mesogenic layer between the first substrate and the second substrate, the mesogenic layer comprising a plurality of mesogens, wherein at least a portion of the plurality of mesogens undergo a detectable switch in orientation upon interaction between the first recognition moiety and the analyte, whereby the interaction between the analyte and the first recognition moiety is detected.

In a fourth aspect, the present invention provides a method for detecting an analyte, comprising:
(a) contacting with the analyte a recognition moiety for the analyte, wherein the contacting causes at least a portion of a plurality of mesogens proximate to the recognition moiety to detectably switch from a first orientation to a second orientation upon contacting the analyte with the recognition moiety; and (b) detecting the second configuration of the at least a portion of the plurality of mesogens, whereby the analyte is detected.

In a fifth aspect, the present invention provides a device for synthesizing and screening a library of compounds, comprising:
(1) a synthesis component, comprising:
 (a) a first substrate having a surface;
 (b) a self-assembled monolayer on the surface, the monolayer comprising a reactive functionality; and
(2) an analysis component, comprising:
 (a) a second substrate having a surface; and
 (b) a mesogenic layer between the surface of the first substrate and the surface of the second substrate.

In a sixth aspect, the present invention provides a library of compounds synthesized on a self-assembled monolayer.

In a seventh aspect, the invention provides a low energy surface having a mesogenic layer anchored planarly thereon.

In an eighth aspect, the invention provides a method for controlling tilt in an organic layer comprising a haloorganosulfur moiety, having a halogen content, adsorbed onto a substrate, the method comprising selecting the halogen content of the haloorganosulfur.

In a ninth aspect, the invention provides a method for controlling optical texture in a mesogenic layer anchored by an organic layer comprising a haloorganosulfur moiety, having a halogen content, the method comprising: selecting the halogen content of the haloorganosulfur.

Other features, objects and advantages of the present invention and its preferred embodiments will become apparent from the detailed description that follows.

BRIEF DESCRIPTION OF THE DRAWINGS

FIG. 1A is a schematic illustration of the change in surface roughness caused by the binding of molecules of Av (left) or IgG (right) to ligands hosted within a SAM of molecules supported on a gold film. The approximate roughness of the surface after binding of Av and IgG is shown by a dashed line. The presence of the SAM on the gold renormalizes the position of the surface and does not erase the roughness of the gold.

FIG. 1B is a scanning tunneling microscopy image of the surface of a thin (~10 nm), semitransparent, obliquely deposited (50° from normal) gold film prepared by electron beam evaporation onto a glass substrate at 0.02 nm s$^{-1}$. A layer of titanium (~200 nm, also deposited obliquely) was used to promote adhesion between the gold and the glass. The vertical and horizontal dimensions of the image are 300 nm and 500 nm, respectively. The gray scale of contrast represents a height range of 0 to 5 nm.

FIG. 1C is a profile of the surface of the gold along the black line shown in Figure B.

FIG. 3 displays optical images (light transmitted through crossed polarizers) of nematic LC sandwiched between mixed SAMs formed from BiSH and $C_8SH$ with or without bound proteins. The thickness of each LC layer was ~2 μm. Unless stated otherwise, the mixed SAMs were supported on anisotropic gold films with preferred directions aligned parallel within the LC cell. All images were recorded by aligning one of the polarizers parallel to the preferred direction within the gold films. The horizontal dimension in each image is 1.1 mm.

FIG. 3A displays mixed SAMs before immersion in PBS containing protein molecules. The optical image became uniformity bright when the sample was rotated by 45° between the crossed polarizers.

FIG. 3B displays mixed SAMs pretreated by immersion in PBS containing 0.5 μM Av.

FIG. 3C displays mixed SAMs formed on gold without anisotropic roughness.

FIG. 3D displays mixed SAMs pretreated by immersion in PBS containing 0.5 μM Av blocked with biotin. The bright lines in the image are caused by scattering of light from disclination loops in the LC [similarly for (G) and (I) below].

FIG. 3E shows mixed SAMs pretreated by immersion for 5 mins. in PBS containing 0.5 μM anti-Bi-IgG.

FIG. 3F shows mixed SAMs pretreated with a nonspecific antibody by immersion for 15 mins. in PBS containing 0.5 μM anti-FITC-IgG.

FIG. 3G shows mixed SAMs pretreated by immersion for 10 mins. in PBS containing 0.5 μM FITC-Av.

FIG. 3H shows mixed SAMs pretreated by immersion for 10 mins. in PBS containing 0.5 μM FITC-Av, then 15 mins. in PBS containing 0.5 μM anti-FITC-lgG.

FIG. 3I shows mixed SAMs pretreated by immersion for 10 mins. in PBS containing 0.5 μM FITC-Av, then 15 mins. in PBS containing 0.5 μM anti-FITC-lgG blocked with fluorescein.

FIG. 8 displays orientations of 5CB from the edge of the optical cell inward.

FIG. 9 is a schematic design of LC cells used to determine the direction of the in-plane (azimuthal) orientation of LC. The bold arrows indicate the direction of gold deposition on the substrate.

FIG. 9A is parallel to evaporation at low pH.

FIG. 9B is perpendicular to evaporation of gold at high pH.

FIG. 10A is an illustration of an optical cell prepared with one surface formed from $HS(CH_2)_{15}CH_3$ and the opposing surface from $HS(CH_2)_{10}COOH$ at low pH and high pH. The bold arrows indicate the direction of gold deposition on the substrate.

FIG. 10B is a schematic illustration of patterned optical cell which supports SAMs of $HS(CH_2)_{15}CH_3$ on $HS(CH_2)_{10}COOH$ pretreated at pH 3 and pH 11.7. Photographs of two different locations this patterned cell shows transmittance of light using polarized light microscopy through;

FIG. 10C cross polars and;

FIG. 10D parallel polars.

FIG. 14 (A to B) demonstrates the use of anchored mesogenic layers to quantitatively follow the conversion of a carboxylic acid to its salt.

FIG. 15 shows the change in orientation of a mesogenic layer caused by binding of $Cu^{+2}$ onto a self-assembled monolayer formed from $HS(CH_2)_{11}COOH$.

FIG. 16 (A to C) display schematic illustrations of optical cells with patterned surfaces. The deformation of the LC within each cell results from patterned anchoring of the LC on the surfaces of the cells.

FIG. 16A displays a SAM formed from alkanethiols with odd numbers of carbon atoms on gold. A nematic LC anchored between two such surfaces is aligned parallel to the surfaces and perpendicular to the direction of gold deposition (indicated by the arrows).

FIG. 16B displays a SAM formed from alkanethiols with even numbers of carbon atoms on gold. A nematic LC anchored between two such surfaces is aligned parallel to the surfaces and parallel to the direction of gold deposition (indicated by the arrows).

FIG. 16C displays a mixed SAM formed from long and short alkanethiols. A nematic LC anchored between two such surfaces is aligned perpendicular to the surfaces.

FIG. 18 displays optical images of mesogenic diffraction gratings.

DETAILED DESCRIPTION OF THE INVENTION AND PREFERRED EMBODIMENTS

Abbreviations and Definitions

Figure 2:
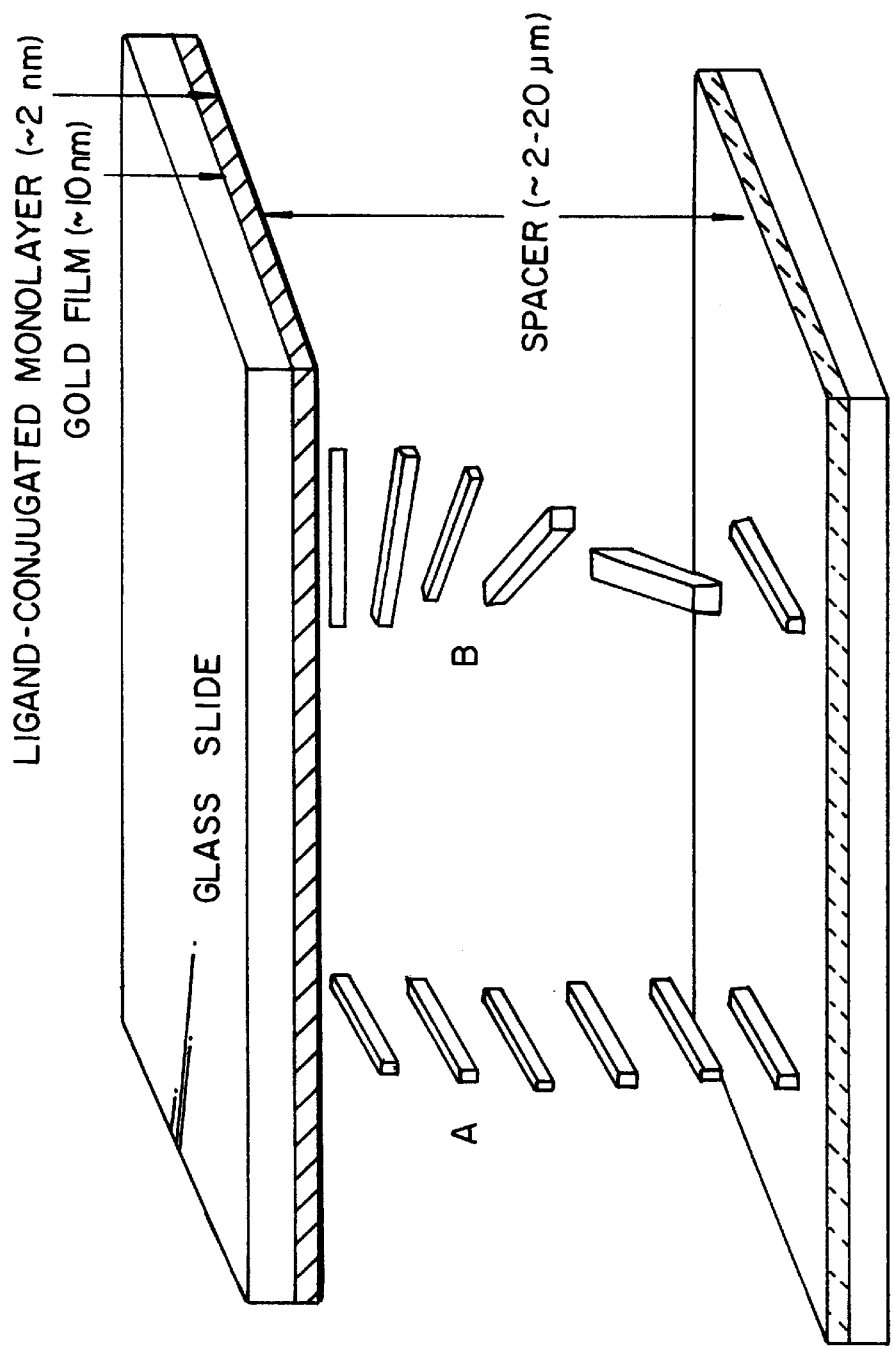
FIG. 2A is a schematic illustration of a LC cell assembled using SAMs formed from ligand-conjugated thiols and alkanethiols on semitransparent gold films supported on glass substrates. A thin layer of titanium separates the gold and glass. Also shown are uniform orientations of bulk LC bounded by two surfaces.
FIG. 2B is a schematic illustration of a LC cell assembled using SAMs formed from ligand-conjugated thiols and alkanethiols on semitransparent gold films supported on glass substrates. A thin layer of titanium separates the gold and glass. Also shown are twisted orientations of bulk LC bounded by two surfaces.

SAM, self assembled monolayer.

The terms used to describe the preferred embodiments of the present invention will generally have their art-recognized meanings. The definitions offered below are intended to supplement, not supplant, the art-recognized meanings.

As used herein, the terms, "mesogen," "mesogenic" and "liquid crystal" are used essentially interchangeably to refer to molecules that form a liquid crystal phase.

The term "attached," as used herein encompasses interaction including, but not limited to, covalent bonding, ionic bonding, chemisorption, physisorption and combinations thereof.

The term "independently selected" is used herein to indicate that the groups so described can be identical or different The term "alkyl" is used herein to refer to a branched or unbranched, saturated or unsaturated, monovalent hydrocarbon radical having from 1–30 carbons and preferably, from 4–20 carbons and more preferably from 6–18 carbons. When the alkyl group has from 1–6 carbon atoms, it is referred to as a "lower alkyl." Suitable alkyl radicals include, for example, structures containing one or more methylene, methine and/or methyne groups. Branched structures have a branching motif similar to i-propyl, t-butyl, i-butyl, 2-ethylpropyl, etc. As used herein, the term encompasses "substituted alkyls."

"Substituted alkyl" refers to alkyl as just described including one or more functional groups such as lower alkyl, aryl, acyl, halogen (i.e., alkylhalos, e.g., $CF_3$), hydroxy, amino, alkoxy, alkylamino, acylamino, thioamido, acyloxy, aryloxy, aryloxyalkyl, mercapto, thia, aza, oxo, both saturated and unsaturated cyclic hydrocarbons, heterocycles and the like. These groups may be attached to any carbon of the alkyl moiety. Additionally, these groups may be pendent from, or integral to, the alkyl chain.

The term "aryl" is used herein to refer to an aromatic substituent which may be a single aromatic ring or multiple aromatic rings which are fused together, linked covalently, or linked to a common group such as a methylene or ethylene moiety. The common linking group may also be a carbonyl as in benzophenone. The aromatic ring(s) may include phenyl, naphthyl, biphenyl, diphenylmethyl and benzophenone among others. The term "aryl" encompasses "arylalkyl."

The term "arylalkyl" is used herein to refer to a subset of "aryl" in which the aryl group is attached to the nucleus shown in Formulae 1–4 by an alkyl group as defined herein.

"Substituted aryl" refers to aryl as just described including one or more functional groups such as lower alkyl, acyl, halogen, alkylhalos (e.g. $CF_3$), hydroxy, amino, alkoxy, alkylamino, acylamino, acyloxy, phenoxy, mercapto and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone. The term "substituted aryl" encompasses "substituted arylalkyl."

"Substituted arylalkyl" defines a subset of "substituted aryl" wherein the substituted aryl group is attached to the nucleus shown in Formulae 1–4 by an alkyl group as defined herein.

The term "acyl" is used to describe a ketone substituent, —C(O)R, where R is alkyl or substituted alkyl, aryl or substituted aryl as defined herein.

The term "halogen" is used herein to refer to fluorine, bromine, chlorine and iodine atoms.

The term "hydroxy" is used herein to refer to the group —OH.,

The term "amino" is used to describe primary amines, R—$NH_2$.

The term "alkoxy" is used herein to refer to the R group, where R is a lower alkyl, substituted lower alkyl, aryl, substituted aryl, arylalkyl or substituted arylalkyl wherein the alkyl, aryl, substituted aryl, arylalkyl and substituted arylalkyl groups are as described herein. Suitable alkoxy radicals include, for example, methoxy, ethoxy, phenoxy, substituted phenoxy, benzyloxy, phenethyloxy, t-butoxy, etc.

The term "alkylamino" denotes secondary and tertiary amines wherein the alkyl groups may be either the same or different and are as described herein for "alkyl groups."

As used herein, the term "acylamino" describes substituents of the general formula RC(O)NR', wherein R' is a lower alkyl group and R represents the nucleus shown in Formulae 1–4 or an alkyl group, as defined herein, attached to the nucleus.

The term "acyloxy" is used herein to describe an organic radical derived from an organic acid by the removal of the acidic hydrogen. Simple acyloxy groups include, for example, acetoxy, and higher homologues derived from carboxylic acids such as ethanoic, propanoic, butanoic, etc. The acyloxy moiety may be oriented as either a forward or reverse ester (i.e. RC(O)OR' or R'OC(O)R, respectively, wherein R comprises the portion of the ester attached either directly or through an intermediate hydrocarbon chain to the nucleus shown in Formulae 1–4).

As used herein, the term "aryloxy" denotes aromatic groups which are linked to the nucleus shown in Formulae 1–4 directly through an oxygen atom. This term encompasses "substituted aryloxy" moieties in which the aromatic group is substituted as described above for "substituted aryl."

As used herein "aryloxyalkyl" defines aromatic groups attached, through an oxygen atom to an alkyl group, as defined herein. The alkyl group is attached to the nucleus shown in Formula 1–4. The term "aryloxyalkyl" encompasses "substituted aryloxyalkyl" moieties in which the aromatic group is substituted as described for "substituted aryl."

As used herein, the term "mercapto" defines moieties of the general structure R—S—R' wherein R and R' are the same or different and are alkyl, aryl or heterocyclic as described herein.

The term "saturated cyclic hydrocarbon" denotes groups such as the cyclopropyl, cyclobutyl, cyclopentyl, etc., and substituted analogues of these structures. These cyclic hydrocarbons can be single- or multi-ring structures.

The term "unsaturated cyclic hydrocarbon" is used to describe a monovalent non-aromatic group with at least one double bond, such as cyclopentene, cyclohexene, etc. and substituted analogues thereof. These cyclic hydrocarbons can be single- or multi-ring structures.

The term "heteroaryl" as used herein refers to aromatic rings in which one or more carbon atoms of the aromatic ring(s) are substituted by a heteroatom such as nitrogen, oxygen or sulfur. Heteroaryl refers to structures which may be a single aromatic ring, multiple aromatic ring(s), or one or more aromatic rings coupled to one or more non-aromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, phthalimide, pyrazole, indole, furan, etc. or benzo-fused analogues of these rings are defined by the term "heteroaryl.""Heteroarylalkyl" defines a subset of "heteroaryl" wherein an alkyl group, as defined herein, links the heteroaryl group to the nucleus shown in Formulae 1–4.

"Substituted heteroaryl" refers to heteroaryl as just described wherein the heteroaryl nucleus is substituted with one or more functional groups such as lower alkyl, acyl, halogen, alkylhalos (e.g. $CF_3$), hydroxy, amino, alkoxy, alkylamino, acylamino, acyloxy, mercapto, etc. Thus, substituted analogues of heteroaromatic rings such as thiophene, pyridine, isoxazole, phthalimide, pyrazole, indole, furan, etc. or benzo-fused analogues of these rings are defined by the term "substituted heteroaryl."

"Substituted heteroarylalkyl" refers to a subset of "substituted heteroaryl" as described above in which an alkyl group, as defined herein, links the heteroaryl group to the nucleus shown in Formulae 1–4.

The term "heterocyclic" is used herein to describe a monovalent saturated or unsaturated non-aromatic group having a single ring or multiple condensed rings from 1–12 carbon atoms and from 14 heteroatoms selected from nitrogen, sulfur or oxygen within the ring. Such heterocycles are, for example, tetrahydrofuran, morpholine, piperidine, pyrrolidine, etc.

The term "substituted heterocyclic" as used herein describes a subset of "heterocyclic" wherein the heterocycle nucleus is substituted with one or more functional groups such as lower alkyl, acyl, halogen, alkylhalos (e.g. $CF_3$), hydroxy, amino, alkoxy, alkylamino, acylamino, acyloxy, mercapto, etc.

The term "heterocyclicalkyl" defines a subset of "heterocyclic" wherein an alkyl group, as defined herein, links the heterocyclic group to the nucleus shown in Formulae 1–4.

As used herein, "conical anchoring" refers to an anchoring characterized by an infinite number of anchoring directions making a fixed angle $\Theta$ with the normal to the interface which is different from 0 and $\Pi/2$.

The term "degenerate anchoring" describes an anchoring mode in which there are an infinite number of anchoring directions.

"Homeotropic anchoring" refers to an anchoring mode characterized by one anchoring direction perpendicular to the plane of the interface. "Multistable anchoring" refers to an anchoring mode characterized by a finite number of anchoring directions greater than one.

As used herein, the term "planar anchoring" refers to an anchoring characterized by anchoring directions parallel to the plane of the interface.

"Tilted anchoring," as used herein, refers to anchoring which makes an angle with the normal to the interface different than 0 and II/2.

The present invention is directed to liquid crystal devices. More particularly, the present invention provides liquid crystal devices that detect the interaction of an analyte with a surface to which the liquid crystal is coupled. The invention provide devices and methods which allow for the amplification and transduction of a molecular interaction. The amplification provides a high degree of resolution and the transduction allows, in its simplest embodiment, the device to be used to optically detect the interaction.

The present invention provides liquid crystal devices and methods of using these devices to detect the presence of an analyte of interest. The devices and methods of the invention can be used to detect both macromolecules (e.g., polymers, proteins, antibodies) and small organic and inorganic molecules.

The devices of the invention are generally multilayered and consist of one or more substrates. A recognition moiety can be bound directly to the substrate or through an organic layer which has optionally been deposited on the substrate. The substrate or the organic layer serves to anchor a mesogenic layer which is orientationally sensitive to interactions (e.g, binding) between the organic layer and the analyte of interest.

Thus in a first aspect, the present invention provides a device comprising: a first substrate having a surface, said surface comprising a recognition moiety; a mesogenic layer oriented on said surface; and an interface between said mesogenic layer and a member selected from the group consisting of gases, liquids, solids and combinations thereof.

This aspect of the present invention allows for the formation of devices of both simple planar and also more complex geometries (e.g., curved, cylindrical, sinusoidal). In a presently preferred embodiment, the substrate of the device is a mesh, for example a TEM grid. In this embodiment, the recognition moiety can be attached to the spaces between the mesh members (i.e., in wells) and the mesogenic layer is floated on the top of the substrate.

In a presently preferred embodiment of this aspect of the invention, the recognition moiety is attached to the surface of the substrate by any of a number of interaction types. Useful attachment modes include, for example, covalent bonding, ionic bonding, chemisorption and physisorption. Devices in which more than one of these modes is used in combination are also within the scope of the present invention.

In another preferred embodiment, the device utilizes a substrate which further comprises an organic layer attached thereto. Similar to the recognition moiety, the organic layer can be attached to the substrate by covalent bonding, ionic bonding, chemisorption, physisorption or combinations of these attachment modes.

In a still further preferred embodiment, the recognition moiety is attached to one or more components of the organic layer. The attachment of the recognition moiety and the organic layer can utilize covalent bonding, ionic bonding, chemisorption, physisorption or combinations of these attachment modes.

In yet a further preferred embodiment, the mesogenic layer is a polymeric mesogen. An array of suitable polymeric mesogens is known to those of skill in the art. See, for example, Imrie et al., *Macromolecules* 26:545–550 (1993); and Percec, V., In, HANDBOOK OF LIQUID CRYSTAL RESEARCH, Collings and Patel, Eds., 1997.

In another preferred embodiment, the interface is between the ambient atmosphere and the mesogen that is layered on either the substrate or on an organic layer. In another presently preferred embodiment, the interface is between the mesogenic layer and a liquid. In a still further preferred embodiment, the interface is between the mesogenic layer and a solid, for example, a second substrate.

In a second aspect, the present invention provides a device comprising: a first substrate having a surface; a second substrate having a surface, said first substrate and said second substrate being aligned such that said surface of said first substrate opposes said surface of said second substrate; a first organic layer attached to said surface of said first substrate, wherein said first organic layer comprises a first recognition moiety; and a mesogenic layer between said first substrate and said second substrate, said mesogenic layer comprising a plurality of mesogenic compounds.

In a third aspect, the present invention provides a device for detecting an interaction between an analyte and a recognition moiety, said device comprising: a first substrate having a surface; a second substrate having a surface, said first substrate and said second substrate being aligned such that said surface of said first substrate opposes said surface of said second substrate; a first organic layer attached to said surface of said first substrate, wherein said organic layer comprises a first recognition moiety which interacts with said analyte; and a mesogenic layer between said first substrate and said second substrate, said mesogenic layer comprising a plurality of mesogens, wherein at least a portion of said plurality of mesogens undergo a detectable switch in orientation upon interaction between said first recognition moiety and said analyte, whereby said interaction between said analyte and said first recognition moiety is detected.

In a fourth aspect, the present invention provides a method for detecting an analyte, comprising:
  (a) contacting with said analyte a recognition moiety for said analyte, wherein said contacting causes at least a portion of a plurality of mesogens proximate to said recognition moiety to detectably switch from a first orientation to a second orientation upon contacting said analyte with said recognition moiety; and
  (b) detecting said second configuration of said at least a portion of said plurality of mesogens, whereby said analyte is detected.

A. Substrates

Substrates that are useful in practicing the present invention can be made of practically any physicochemically stable material. In a preferred embodiment, the substrate material is non-reactive towards the constituents of the mesogenic layer. The substrates can be either rigid or flexible and can be either optically transparent or optically opaque. The substrates can be electrical insulators, conductors or semiconductors. Further the substrates can be substantially impermeable to liquids, vapors and/or gases or, alternatively, the substrates can be permeable to one or more of these classes of materials.

Exemplary substrate materials include, but are not limited to, inorganic crystals, inorganic glasses, inorganic oxides, metals, organic polymers and combinations thereof.

A.1 Inorganic crystal and glasses

Inorganic crystals and inorganic glasses that are appropriate for substrate materials include, for example, LiF, NaF, NaCl, KBr, KI, $CaF_2$, $MgF_2$, $HgF_2$, BN, $AsS_3$, ZnS, $Si_3N_4$ and the like. The crystals and glasses can be prepared by art standard techniques. See, for example, Goodman, C. H. L., Crystal Growth Theory and Techniques, Plenum Press, New York 1974. Alternatively, the crystals can be purchased commercially (e.g., Fischer Scientific). The crystals can be the sole component of the substrate or they can be coated with one or more additional substrate components. Thus, it is within the scope of the present invention to utilize crystals coated with, for example one or more metal films or a metal film and an organic polymer. Additionally, a crystal can constitute a portion of a substrate which contacts another portion of the substrate made of a different material, or a different physical form (e.g., a glass) of the same material. Other useful substrate configurations utilizing inorganic crystals and/or glasses will be apparent to those of skill in the art.

A.2 Inorganic oxides

Inorganic oxides can also form a substrate of the device of the present invention. Inorganic oxides of use in the present invention include, for example, $Cs_2O$, $Mg(OH)_2$, $TiO_2$, $ZrO_2$, $CeO_2$, $Y_2O_3$, $Cr_2O_3$, $Fe_2O_3$, NiO, ZnO, $Al_2O_3$, $SiO_2$ (glass), quartz, $In_2O_3$, $SnO_2$, $PbO_2$ and the like. The inorganic oxides can be utilized in a variety of physical forms such as forms, supported powders, glasses, crystals and the like. A substrate can consist of a single inorganic oxide or a composite of more than one inorganic oxide. For example, a composite of inorganic oxides can have a layered structure (i.e., a second oxide deposited on a first oxide) or two or more oxides can be arranged in a contiguous non-layered structure. In addition, one or more oxides can be admixed as particles of various sizes and deposited on a support such as a glass or metal sheet. Further, a layer of one or more inorganic oxides can be intercalated between two other substrate layers (e.g., metal-oxide-metal, metal-oxide-crystal).

In a presently preferred embodiment, the substrate is a rigid structure that is impermeable to liquids and gases. In this embodiment, the substrate consists of a glass plate onto which a metal, such as gold is layered by evaporative deposition. In a still further preferred embodiment, the substrate is a glass plate ($SiO_2$) onto which a first metal layer such as titanium has been layered. A layer of a second metal such as gold is then layered on top of the first metal layer.

A.3 Metals

Metals are also of use as substrates in the present invention. The metal can be used as a crystal, a sheet or a powder. The metal can be deposited onto a backing by any method known to those of skill in the art including, but not limited to, evaporative deposition, sputtering and electroless deposition.

Any metal that is chemically inert towards the mesogenic layer will be useful as a substrate in the present invention. Metals that are presently preferred as substrates include, but are not limited to, gold, silver, platinum, palladium, nickel and copper. In one embodiment, more than one metal is used. The more than one metal can be present as an alloy or they can be formed into a layered "sandwich" structure, or they can be laterally adjacent to one another. In a preferred embodiment, the metal used for the substrate is gold. In a particularly preferred embodiment the metal used is gold layered on titanium.

The metal layers can be either permeable or impermeable to materials such as liquids, solutions, vapors and gases.

A.4 Organic polymers

Organic polymers are a useful class of substrate materials. Organic polymers useful as substrates in the present invention include polymers which are permeable to gases, liquids and molecules in solution. Other useful polymers are those which are impermeable to one or more of these same classes of compounds.

Organic polymers that form useful substrates include, for example, polyalkenes (e.g., polyethylene, polyisobutene, polybutadiene), polyacrylics (e.g., polyacrylate, polymethyl methacrylate, polycyanoacrylate), polyvinyls (e.g., polyvinyl alcohol, polyvinyl acetate, polyvinyl butyral, polyvinyl chloride), polystyrenes, polycarbonates, polyesters, polyurethanes, polyamides, polyimides, polysulfone, polysiloxanes, polyheterocycles, cellulose derivative (e.g., methyl cellulose, cellulose acetate, nitrocellulose), polysilanes, fluorinated polymers, epoxies, polyethers and phenolic resins. See, Cognard, J. ALIGNMENT OF NEMATIC LIQUID CRYSTALS AND THEIR MIXTURES, in *Mol. Cryst. Liq. Cryst.* 1:1–74 (1982). Presently preferred organic polymers include polydimethylsiloxane, polyethylene, polyacrylonitrile, cellulosic materials, polycarbonates and polyvinyl pyridinium.

In a presently preferred embodiment, the substrate is permeable and it consists of a layer of gold, or gold over titanium, which is deposited on a polymeric membrane, or other material, that is permeable to liquids, vapors and/or gases. The liquids and gases can be pure compounds (e.g., chloroform, carbon monoxide) or they can be compounds which are dispersed in other molecules (e.g., aqueous protein solutions, herbicides in air, alcoholic solutions of small organic molecules). Useful permeable membranes include, but are not limited to, flexible cellulosic materials (e.g., regenerated cellulose dialysis membranes), rigid cellulosic materials (e.g., cellulose ester dialysis membranes), rigid polyvinylidene fluoride membranes, polydimethylsiloxane and track etched polycarbonate membranes.

In a further preferred embodiment, the layer of gold on the permeable membrane is itself permeable. In a still further preferred embodiment, the permeable gold layer has a thickness of about 70 Å or less.

In those embodiments wherein the permeability of the substrate is not a concern and a layer of a metal film is used, the film can be as thick as is necessary for a particular application. For example, if the film is used as an electrode, the film can be thicker than in an embodiment in which it is necessary for the film to be transparent or semi-transparent to light.

Thus, in a preferred embodiment, the film is of a thickness of from about 0.01 nanometer to about 1 micrometer. In a further preferred embodiment, the film is of a thickness of from about 5 nanometers to about 100 nanometers. In yet a further preferred embodiment, the film is of a thickness of from about 10 nanometers to about 50 nanometers.

A.5 Substrate surfaces

The nature of the surface of the substrate has a profound effect on the anchoring of the mesogenic layer which is associated with the surface. The surface can be engineered by the use of mechanical and/or chemical techniques. The surface of each of the above enumerated substrates can be substantially smooth. Alternatively, the surface can be roughened or patterned by rubbing, etching, grooving, stretching, oblique deposition or other similar techniques known to those of skill in the art. Of particular relevance is the texture of the surface which is in contact with the mesogenic compounds.

Thus, in one preferred embodiment, the substrate is glass or an organic polymer and the surface has been prepared by rubbing. Rubbing can be accomplished using virtually any material including tissues, paper, brushes, polishing paste, etc. In a preferred embodiment, the rubbing is accomplished by use of a diamond rubbing paste. In another preferred embodiment, the face of the substrate that contacts the mesogenic compounds is a metal layer that has been obliquely deposited by evaporation. In a further preferred embodiment, the metal layer is a gold layer.

The substrate can also be patterned using techniques such as photolithography (Kleinfield et al., *J. Neurosci.* 8:4098–120 (1998)), photoetching, chemical etching and microcontact printing (Kumar et al., *Langmuir* 10:1498–511 (1994)). Other techniques for forming patterns on a substrate will be readily apparent to those of skill in the art.

The size and complexity of the pattern on the substrate is limited only by the resolution of the technique utilized and the purpose for which the pattern is intended. For example, using microcontact printing, features as small as 200 nm have been layered onto a substrate. See, Xia, Y.; Whitesides, G., *J. Am. Chem. Soc.* 117:3274–75 (1995). Similarly, using photolithography, patterns with features as small as 1 $\mu$m have been produced. See, Hickman et al., *J. Vac. Sci. Technol.* 12:607–16(1994). Patterns which are useful in the present invention include those which comprise features such as wells, enclosures, partitions, recesses, inlets, outlets, channels, troughs, diffraction gratings and the like.

In a presently preferred embodiment, the patterning is used to produce a substrate having a plurality of adjacent wells, wherein each of the wells is isolated from the other wells by a raised wall or partition and the wells do not fluidically communicate. Thus, an analyte, or other substance, placed in a particular well remains substantially confined to that well. In another preferred embodiment, the patterning allows the creation of channels through the device whereby an analyte can enter and/or exit the device.

The pattern can be printed directly onto the substrate or, alternatively, a "lift off" technique can be utilized. In the lift off technique, a patterned resist is laid onto the substrate, an organic layer is laid down in those areas not covered by the resist and the resist is subsequently removed. Resists appropriate for use with the substrates of the present invention are known to those of skill in the art. See, for example, Kleinfield et al., *J. Neurosci.* 8:4098–120 (1998). Following removal of the photoresist, a second organic layer, having a structure different from the first organic layer can be bonded to the substrate on those areas initially covered by the resist. Using this technique, substrates with patterns having regions of different chemical characteristics can be produced. Thus, for example, a pattern having an array of adjacent wells can be created by varying the hydrophobicity/hydrophilicity, charge and other chemical characteristics of the pattern constituents. In one embodiment, hydrophilic compounds can be confined to individual wells by patterning walls using hydrophobic materials. Similarly, positively or negatively charged compounds can be confined to wells having walls made of compounds with charges similar to those of the confined compounds. Similar substrate configurations are accessible through microprinting a layer with the desired characteristics directly onto the substrate. See, Mrkish, M.; Whitesides, G. M., *Ann. Rev. Biophys. Biomol. Struct.* 25:55–78 (1996).

In yet another preferred embodiment, the patterned substrate controls the anchoring alignment of the liquid crystal. In a particularly preferred embodiment, the substrate is patterned with an organic compound which forms a self-assembled monolayer. In this embodiment, the organic layer controls the azimuthal orientation and/or polar orientation of a supported mesogenic layer.

B. Organic Layers

In addition to the ability of a substrate to anchor a mesogenic layer, an organic layer attached to the substrate is similarly able to provide such anchoring. A wide range of organic layers can be used in conjunction with the present invention. These include organic layers formed from organothiols, organosilanes, amphiphilic molecules, cyclodexins, polyols (e.g., poly(ethyleneglycol), poly(propyleneglycol), fullerenes, and biomolecules. Other useful compounds will be apparent to those of skill in the art.

B.1 Anchoring

An organic layer that is bound to, supported on or adsorbed onto, the surface of the substrate can anchor a mesogenic layer. As used herein, the term "anchoring") refers to the set of orientations adopted by the molecules in the mesogenic phase. The mesogenic layer will adopt particular orientations while minimizing the free energy of the interface between the organic layer and the mesogenic layer. The orientation of the mesogenic layer is referred to as an "anchoring direction." A number of anchoring directions are possible.

The particular anchoring direction adopted will depend upon the nature of the mesogenic layer, the organic layer and the substrate. Anchoring directions of use in the present invention include, for example, conical anchoring, degenerate anchoring, homeotropic anchoring, multistable anchoring, planar anchoring and tilted anchoring. Planar anchoring and homeotropic anchoring are preferred with homeotropic anchoring being most preferred.

The anchoring of mesogenic compounds by surfaces has been extensively studied for a large number of systems. See, for example, Jerome, B., *Rep. Prog. Phys.* 54:391–451 (1991). The anchoring of a mesogenic substance by a surface is specified, in general, by the orientation of the director of the bulk phase of the mesogenic layer. The orientation of the director, relative to the surface, is described by a polar angle (measured from the normal of the surface) and an azimuthal angle (measured in the plane of the surface).

Control of the anchoring of mesogens has been largely based on the use of organic surfaces prepared by coating surface-active molecules or polymer films on inorganic (e.g., silicon oxide) substrates followed by surface treatments such as rubbing. Other systems which have been found useful include surfaces prepared through the reactions of organosilanes with various substrates. See, for example, Yang et al., In, MICROCHEMISTRY: SPECTROSCOPY AND CHEMISTRY IN SMALL DOMAINS; Masuhara et al., Eds.; North-Holland, Amsterdam, 1994; p.441.

Molecularly designed surfaces formed by organic layers on a substrate can be used to control both the azimuthal and polar orientations of a supported mesogenic layer. SAMs can be patterned on a surface. For example, patterned organic layers made from $CH_3(CH_2)_{14}SH$ and $CH_3(CH_2)_{15}SH$ on obliquely deposited gold produce a supported mesogenic layer which is twisted 90°. Other anchoring modes are readily accessible by varying the chain length and the number of species of the organic layer constituents. See, Gupta, V. K.; Abbott, N. L., *Science* 276:1533–1536 (1997).

Transitions between anchoring modes have been obtained on a series of organic layers by varying the structure of the organic layer. The structural features which have been found to affect the anchoring of mesogenic compounds include, for example, the density of molecules within the organic layer, the size and shape of the molecules constituting the organic layer and the number of individual layers making up the bulk organic layer.

The density of the organic layer on the substrate has been shown to have an effect on the mode of mesogen anchoring. For example, transitions between homeotropic and degenerate anchorings have been obtained on surfactant monolayers by varying the density of the monolayers. See, Proust et al., *Solid State Commun.* 11:1227–30 (1972). Thus, it is within the scope of the present invention to tailor the anchoring mode of a mesogen by controlling the density of the organic layer on the substrate.

The molecular structure, size and shape of the individual molecules making up the organic layer also affects the anchoring mode. For example, it has been demonstrated that varying the length of the aliphatic chains of surfactants on a substrate can also induce anchoring transitions: with long chains, a homeotropic anchoring is obtained while with short chains, a conical anchoring is obtained with the tilt angle κ increasing as the chain becomes shorter. See, for example, Porte, *J. Physique* 37:1245–52 (1976). Additionally, recent reports have demonstrated that the polar angle of the mesogenic phase can be controlled by the choice of the constituents of the organic layer. See, Gupta, V. K.; Abbott, N. L., *Langmuir* 12:2587–2593 (1996). Thus, it is within the scope of the present invention to engineer the magnitude of the anchoring shift as well as the type of shift by the judicious choice of organic layer constituents.

A wide variety of organic layers are useful in practicing the present invention. These organic layers can comprise monolayers, bilayers and multilayers. Furthermore, the organic layers can be attached by covalent bonds, ionic bonds, physisorption, chemisorption and the like, including, but not limited to, hydrophobic interactions, hydrophilic interactions, van der Waals interactions and the like.

In a presently preferred embodiment, organic layers which form self- assembled monolayers are used.

The use of self-assembled monolayers (SAMs) formed from alkanethiols on thin, semitransparent films of gold in studies on the anchoring of liquid crystals on surfaces has been reported. See, Drawhorn, R. A.; Abbott, N. L., *J. Phys. Chem.* 45:16511 (1995). The principal result of that work was the demonstration that SAMs formed from n-alkanethiols with long ($CH_3(CH_2)_{15}SH$) and short ($CH_3(CH_2)_4SH$ or $CH_3(CH_2)_9SH$) aliphatic chains can homeotropically anchor mesogens. In contrast, single-component SAMs ($CH_3(CH_2)_nSH$, 2<n>15) caused non-uniform, planar, or tilted anchoring at room temperature.

In the discussion that follows, self-assembled monolayers are utilized as an exemplary organic layer. This use is not intended to be limiting. It will be understood that the various configurations of the self-assembled monolayers and their methods of synthesis, binding properties and other characteristics are equally applicable to each of the organic layers of use in the present invention.

B.2 Self-Assembled Monolayers

Self-assembled monolayers are generally depicted as an assembly of organized, closely packed linear molecules. There are two widely-used methods to deposit molecular monolayers on solid substrates: Langmuir-Blodgett transfer and self-assembly. Additional methods include techniques such as depositing a vapor of the monolayer precursor onto a substrate surface.

The composition of a layer of a SAM useful in the present invention, can be varied over a wide range of compound structures and molar ratios. In one embodiment, the SAM is formed from only one compound. In a presently preferred embodiment, the SAM is formed from two or more components. In another preferred embodiment, when two or more components are used, one component is a long-chain hydrocarbon having a chain length of between 10 and 25 carbons and a second component is a short-chain hydrocarbon having a chain length of between 1 and 9 carbon atoms. In particularly preferred embodiments, the SAM is formed from $CH_3(CH_2)_{15}SH$ and $CH_3(CH_2)_4SH$ or $CH_3(CH_2)_{15}SH$ and $CH_3(CH_2)_9SH$. In any of the above described embodiments, the carbon chains can be functionalized at the ω-terminus (e.g., $NH_2$, COOH, OH, CN), at internal positions of the chain (e.g., aza, oxa, thia) or at both the ω-terminus and internal positions of the chain.

The mesogenic layer can be layered on top of one SAM layer or it can be sandwiched between two SAM layers. In those embodiments in which the mesogenic layer is sandwiched between two SAMs, a second substrate, optionally substantially identical in composition to that bearing the SAM can be layered on top of the mesogenic layer. Alternatively a compositionally different substrate can be layered on top of the mesogenic layer. In a preferred embodiment, the second substrate is permeable.

In yet another preferred embodiment two substrates are used, but only one of the substrates has an attached organic layer.

When the mesogenic layer is sandwiched between two layers of SAMs several compositional permutations of the layers of SAMs are available. For example, in one embodiment, the first organic layer and the second organic layer have substantially identical compositions and both of the organic layers bear an attached recognition moiety. A variation on this embodiment utilizes first and second organic layers with substantially similar compositions, wherein only one of the layers bears a recognition moiety.

In another embodiment, the first and second organic layers have substantially different compositions and only one of the organic layers has an attached recognition moiety. In a further embodiment, the first organic layer and said second organic layer have substantially different compositions and both of the organic layers have an attached recognition moiety.

In a presently preferred embodiment, the organic layers have substantially identical compositions and one or both of the organic layers has attached thereto a recognition moiety.

A recognition moiety can be attached to the surface of a SAM by any of a large number of art-known attachment methods. In one preferred embodiment, a reactive SAM component is attached to the substrate and the recognition moiety is subsequently bound to the SAM component via the reactive group on the component and a group of complementary reactivity on the recognition moiety. See, for example, Hegner et al. *Biophys. J.* 70:2052–2066 (1996). In another preferred embodiment, the recognition moiety is attached to the SAM component prior to immobilizing the SAM component on the substrate surface: the recognition moiety-SAM component cassette is then attached to the substrate. In a still further preferred embodiment, the recognition moiety is attached to the substrate via a displacement reaction. In this embodiment, the SAM is preformed and then a fraction of the SAM components are displaced by a recognition moiety or a SAM component bearing a recognition moiety.

B.3 Functionalized SAMs

The discussion which follows focuses on the attachment of a reactive SAM component to the substrate surface. This focus is for convenience only and one of skill in the art will understand that the discussion is equally applicable to embodiments in which the SAM component-recognition moiety is preformed prior to its attachment to the substrate. As used herein, "reactive SAM components" refers to components which have a functional group available for reaction with a recognition moiety or other species following the attachment of the component to the substrate.

Currently favored classes of reactions available with reactive SAM components are those which proceed under relatively mild conditions. These include, but are not limited to nucleophilic substitutions (e.g., reactions of amines and alcohols with acyl halides), electrophilic substitutions (e.g, enamine reactions) and additions to carbon—carbon and carbon-heteroatom multiple bonds (e.g., Michael reaction, Diels-Alder addition). These and other useful reactions are discussed in March, J., ADVANCED ORGANIC CHEMISTRY, Third Ed., John Wiley & Sons, New York, 1985.

According to the present invention, a substrate's surface is functionalized with SAM components and other species by covalently binding a reactive SAM component to the substrate surface in such a way as to derivatize the substrate surface with a plurality of available reactive functional groups. reactive groups which can be used in practicing the present invention include, for example, amines, hydroxyl groups, carboxylic acids, carboxylic acid derivatives, alkenes, sulfhydryls, siloxanes, etc.

A wide variety of reaction types is available for the functionalization of a substrate surface. For example, substrates constructed of a plastic such as polypropylene, can be surface derivatized by chromic acid oxidation, and subsequently converted to hydroxylated or aminomethylated surfaces. Substrates made from highly crosslinked divinylbenzene can be surface derivatized by chloromethylation and subsequent functional group manipulation. Additionally, functionalized substrates can be made from etched, reduced polytetrafluoroethylene When the substrates are constructed of a siliceous material such as glass, the surface can be derivatized by reacting the surface Si—OH, SiO—H, and/or Si—Si groups with a functionalizing reagent. When the substrate is made of a metal film, the surface can be derivatized with a material displaying avidity for that metal.

In a preferred embodiment, wherein the substrates are made from glass, the covalent bonding of the reactive group to the glass surface is achieved by conversion of groups on the substrate's surface by a silicon modifying reagent such as:

  (1)

where R is an alkyl group, such as methyl or ethyl, $R^1$ is a linking group between silicon and X and X is a reactive group or a protected reactive group. The reactive group can also be a recognition moiety as discussed below. Silane derivatives having halogens or other leaving groups beside the displayed alkoxy groups are also useful in the present invention.

A number of siloxane functionalizing reagents can be used, for example:

1. Hydroxyalkyl siloxanes (Silylate surface, functionalize with diborane, and $H_2O_2$ to oxidize the alcohol)
   a. allyl trichlorosilane→→3-hydroxypropyl
   b. 7-oct-1-enyl trichlorchlorosilane→→8-hydroxyoctyl
2. Diol (dihydroxyalkyl) siloxanes (silylate surface and hydrolyze to diol)
   a. (glycidyl trimethoxysilane→→(2,3-dihydroxypropyloxy)propyl
3. Aminoalkyl siloxanes (amines requiring no intermediate functionalizing step)
   a. 3-aminopropyl trimethoxysilane→→aminopropyl
4. Dimeric secondary aminoalkyl siloxanes
   a. bis (3-trimethoxysilylpropyl) amine→bis (silyloxylpropyl)amine.

It will be apparent to those of skill in the art that an array of similarly useful functionalizing chemistries are available when SAM components other than siloxanes are used. Thus, for example similarly functionalized alkyl thiols can be attached to metal films and subsequently reacted to produce the functional groups such as those exemplified above In another preferred embodiment, the substrate is at least partially a metal film, such as a gold film, and the reactive group is tethered to the metal surface by an agent displaying avidity for that surface. In a presently preferred embodiment, the substrate is at least partially a gold film and the group which reacts with the metal surface comprises a thiol, sulfide or disulfide such as:

  (2)

$R^2$ is a linking group between sulfur and $X^2$ and $X^2$ is a reactive group or a protected reactive group. $X^2$ can also be a recognition moiety as discussed below. Y is a member selected from the group consisting of H, $R^3$ and $R^3$—S—, wherein $R^2$ and $R^3$ are independently selected. When $R^2$ and $R^3$ are the same, symmetrical sulfides and disulfides result, and when they are different, asymmetrical sulfides and disulfides result.

A large number of functionalized thiols, sulfides and disulfides are commercially available (Aldrich Chemical Co., St. Louis). Additionally, those of skill in the art have available to them a manifold of synthetic routes with which to produce additional such molecules. For example, amine-functionalized thiols can be produced from the corresponding halo-amines, halo-carboxylic acids, etc. by reaction of these halo precursors with sodium sulfhydride. See, for example, Reid, ORGANIC CHEMISTRY OF BIVALENT SULFUR, vol. 1, pp. 21–29, 32–35, vol. 5, pp. 27–34, Chemical Publishing Co., New York, 1958, 1963. Additionally, functionalized sulfides can be prepared via alkylthio-de-halogenation with a mercaptan salt. See, Reid, ORGANIC CHEMISTRY OF BIVALENT SULFUR, vol. 2, pp. 16–21, 24–29, vol. 3, pp. 11–14, Chemical Publishing Co., New York, 1960. Other methods for producing compounds useful in practicing the present invention will be apparent to those of skill in the art.

In another preferred embodiment, the functionalizing reagent provides for more than one reactive group per each reagent molecule. Using reagents such as Compound 3, below, each reactive site on the substrate surface is, in essence, "amplified" to two or more functional groups:

  (3)

where R is an alkyl group, such as methyl, $R^1$ is a linking group between silicon and $X^1$, $X^1$ is a reactive group or a protected reactive group and n is an integer between 2 and 50, and more preferably between 2 and 20.

Similar amplifying molecules are also of use in those embodiments wherein the substrate is at least partially a metal film. In these embodiments the group which reacts with the metal surface comprises a thiol, sulfide or disulfide such as in Formula (4):

  (4)

As discussed above, $R^2$ is a linking group between sulfur and $X^2$ and $X^2$ is a reactive group or a protected reactive group. $X^2$ can also be a recognition moiety. Y is a member selected from the group consisting of H, $R^3$ and $R^3$—S—, wherein $R^2$ and $R^3$ are independently selected.

R groups of use for $R^1$, $R^2$ and $R^3$ in the above described embodiments of the present invention include, but are not limited to, alkyl, substituted alkyl, aryl, arylalkyl, substituted aryl, substituted arylalkyl, acyl, halogen, hydroxy, amino, alkylamino, acylamino, alkoxy, acyloxy, aryloxy, aryloxyalkyl, mercapto, saturated cyclic hydrocarbon, unsaturated cyclic hydrocarbon, heteroaryl, heteroarylalkyl, substituted heteroaryl, substituted heteroarylalkyl, heterocyclic, substituted heterocyclic and heterocyclicalkyl groups In each of Formulae 1–4, above, each of $R^1$, $R^2$ and $R^3$ are either stable or they can be cleaved by chemical or photochemical reactions. For example, R groups comprising ester or disulfide bonds can be cleaved by hydrolysis and reduction, respectively. Also within the scope of the present invention is the use of R groups which are cleaved by light such as, for example, nitrobenzyl derivatives, phenacyl groups, benzoin esters, etc. Other such cleaveable groups are well-known to those of skill in the art.

In another preferred embodiment, the organosulfur compound is partially or entirely halogenated. An example of compounds useful in this embodiment include:

$$X^1Q_2C(CQ^1{}_2)_mZ^1(CQ^2{}_2)_nSH \qquad (5)$$

wherein, $X^1$ is a member selected from the group consisting of H, halogen reactive groups and protected reactive groups. Reactive groups can also be recognition moieties as discussed below. Q, $Q^1$ and $Q^2$ are independently members selected from the group consisting of H and halogen. $Z^1$ is a member selected from the group consisting of —$CQ_2$—, —$CQ^1{}_2$—, —$CQ^2{}_2$—, —O—, —S—, —$NR^4$—, —$C(O)NR^4$ and $R^4NC(O)$—, in which $R^4$ is a member selected from the group consisting of H, alkyl, substituted alkyl, aryl, substituted aryl, heteroaryl and heterocyclic groups and m and n are independently a number between 0 and 40.

In yet another preferred embodiment, the organic layer comprises a compound according to Formula 5 above, in which Q, $Q^1$ and $Q^2$ are independently members selected from the group consisting of H and fluorine. In a still further preferred embodiment, the organic layer comprises compounds having a structure according to Formulae (6) and (7):

$$CF_3(CF_2)_mZ^1(CH_2)_nSH \qquad (6)$$

$$CF_3(CF_2)_oZ^2(CH_2)_pSH \qquad (7)$$

wherein, $Z^1$ and $Z^2$ are members independently selected from the group consisting of —$CH_2$—, —O—, —S—, —$NR^4$—, —$C(O)NR^4$ and $R^4NC(O)$— in which $R^4$ is a member selected from the group consisting of H, alkyl, substituted alkyl, aryl, substituted aryl, heteroaryl and heterocyclic groups. In a presently preferred embodiment, the Z groups of adjacent molecules participate in either an attractive (e.g., hydrogen bonding) or repulsive (e.g., van der Waals) interaction.

In Formula 7, m is a number between 0 and 40, n is a number between 0 and 40, o is a number between 0 and 40 and p is a number between 0 and 40.

In a further preferred embodiment, the compounds of Formulae 6 and 7 are used in conjunction with an organosulfur compound, either halogentated or unhalogenated, that bears a recognition moiety.

When the organic layer is formed from a halogenated organosulfur compound, the organic layer can comprise a single halogenated compound or more than one halogenated compound having different structures. Additionally, these layers can comprise a non-halogenated organosulfur compound.

The reactive functional groups ($X^1$ and $X^2$) are, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups which can be converted to disulfides or reacted with acyl halides;

(h) amine or sulfhydryl groups which can be, for example, acylated or alkylated;

(i) alkenes which can undergo, for example, cycloadditions, acylation, Michael addition, etc; and (i) epoxides which can react with, for example, amines and hydroxyl compounds.

The reactive moieties can also be recognition moieties. The nature of these groups is discussed in greater detail below.

The reactive functional groups can be chosen such that they do not participate in, or interfere with, the reaction controlling the attachment of the functionalized SAM component onto the substrate's surface. Alternatively, the reactive functional group can be protected from participating in the reaction by the presence of a protecting group. Those of skill in the art will understand how to protect a particular functional group from interfering with a chosen set of reaction conditions. For examples of useful protecting groups, See Greene et al., PROTECTIVE GROUPS IN ORGANIC SYNTHESIS, John Wiley & Sons, New York, 1991.

In a preferred embodiment, the SAM component bearing the recognition moiety is attached directly and essentially irreversibly via a "stable bond" to the surface of the substrate. A "stable bond", as used herein, is a bond which maintains its chemical integrity over a wide range of conditions (e.g., amide, carbamate, carbon—carbon, ether, etc.). In another preferred embodiment the SAM component bearing the recognition moiety is attached to the substrate surface by a "cleaveable bond". A "cleaveable bond", as used herein, is a bond which is designed to undergo scission under conditions which do not degrade other bonds in the recognition moiety-analyte complex. Cleaveable bonds include, but are not limited to, disulfide, imine, carbonate and ester bonds.

In certain embodiments, it is advantageous to have the recognition moiety attached to a SAM component having a structure that is different than that of the constituents of the bulk SAM. In this embodiment, the group to which the recognition moiety is bound is referred to as a "spacer arm" or "spacer." Using such spacer arms, the properties of the SAM adjacent to the recognition moiety can be controlled. Properties that are usefully controlled include, for example, hydrophobicity, hydrophilicity, surface-activity and the distance of the recognition moiety from the plane of the substrate and/or the SAM. For example, in a SAM composed of alkanethiols, the recognition moiety can be attached to the substrate or the surface of the SAM via an amine terminated poly(ethyleneglycol). Numerous other combinations of spacer arms and SAMs are accessible to those of skill in the art.

The hydrophilicity of the substrate surface can be enhanced by reaction with polar molecules such as amine-, hydroxyl- and polyhydroxyl-containing molecules. Representative examples include, but are not limited to, polylysine, polyethyleneimine, poly(ethyleneglycol) and poly(propyleneglycol). Suitable functionalization chemistries and strategies for these compounds are known in the art. See, for example, Dunn, R. L., et al., Eds. POLYMERIC DRUGS AND DRUG DELIVERY SYSTEMS, ACS Symposium Series Vol. 469, American Chemical Society, Washington, D.C. 1991.

The hydrophobicity of the substrate surface can be modulated by using a hydrophobic spacer arm such as, for example, long chain diamines, long-chain thiols, $\alpha$, $\omega$-amino acids, etc. Representative hydrophobic spacers include, but are not limited to, 1,6-hexanediamine, 1,8-octanediamine, 6-aminohexanoic acid and 8-aminooctanoic acid.

The substrate surface can also be made surface-active by attaching to the substrate surface a spacer which has surfactant properties. Compounds useful for this purpose include, for example, aminated or hydroxylated detergent molecules such as, for example, 1-aminododecanoic acid.

In another embodiment, the spacer serves to distance the recognition moiety from the substrate or SAM. Spacers with this characteristic have several uses. For example, a recognition moiety held too closely to the substrate or SAM surface may not react with incoming analyte, or it may react unacceptably slowly. When an analyte is itself sterically demanding, the reaction leading to recognition moiety-analyte complex formation can be undesirably slowed, or not occur at all, due to the monolithic substrate hindering the approach of the two components.

In another embodiment, the physicochemical characteristics (e.g., hydrophobicity, hydrophilicity, surface activity, conformation) of the substrate surface and/or SAM are altered by attaching a monovalent moiety which is different in composition than the constituents of the bulk SAM and which does not bear a recognition moiety. As used herein, "monovalent moiety" refers to organic molecules with only one reactive functional group. This functional group attaches the molecule to the substrate. "Monovalent moieties" are to be contrasted with the bifunctional "spacer" groups described above. Such monovalent groups are used to modify the hydrophilicity, hydrophobicity, binding characteristics, etc. of the substrate surface. Examples of groups useful for this purpose include long chain alcohols, amines, fatty acids, fatty acid derivatives, poly (ethyleneglycol) monomethyl ethers, etc.

When two or more structurally distinct moieties are used as components of the SAMs, the components can be contacted with the substrate as a mixture of SAM components or, alternatively, the components can be added individually. In those embodiments in which the SAM components are added as a mixture, the mole ratio of a mixture of the components in solution results in the same ratio in the mixed SAM. Depending on the manner in which the SAM is assembled, The two components do not phase segregate into islands. See, Bain, C. D.; Whitesides, G. M., *J. Am. Chem. Soc.* 111:7164 (1989). This feature of SAMs can be used to immobilize recognition moieties or bulky modifying groups in such a manner that certain interactions, such as steric hindrance, between these molecules is minimzed.

The individual components of the SAMs can also be bound to the substrate in a sequential manner. Thus, in one embodiment, a first SAM component is attached to the substrate's surface by "underlabeling" the surface functional groups with less than a stoichiometric equivalent of the first component. The first component can be a SAM component liked to a terminal reactive group or recognition group, a spacer arm or a monovalent moiety. Subsequently, the second component is contacted with the substrate. This second component can either be added in stoichiometric equivalence, stoichiometric excess or can again be used to underlabel to leave sites open for a third component.

C. Recognition Moieties

As used herein, the term "recognition moiety" refers to molecules which are attached to either $\omega$-functionalized spacer arms or $\omega$-functionalized SAM components. Furthermore, a recognition moiety can be presented by a polymer surface (e.g., a rubbed polymer surface). The recognition moieties bind to, or otherwise interact with, the analyte of interest.

In a preferred embodiment, the recognition moiety comprises an organic functional group. In presently preferred embodiments, the organic functional group is a member selected from the group consisting of amines, carboxylic acids, drugs, chelating agents, crown ethers, cyclodextrins or a combination thereof.

In another preferred embodiment, the recognition moiety is a biomolecule. In still further preferred embodiments, the biomolecule is a protein, antibody, peptide, nucleic acid (e.g., single nucleotides or nucleosides, oligo nucleotides, polynucleotides and single- and higher-stranded nucleic acids) or a combination thereof. In a presently preferred embodiment, the recognition moiety is biotin.

When the recognition moiety is an amine, in preferred embodiments, the recognition moiety will interact with a structure on the analyte which reacts by binding to the amine (e.g., carbonyl groups, alkylhalo groups). In another preferred embodiment, the amine is protonated by an acidic moiety on the analyte of interest (e.g., carboxylic acid, sulfonic acid).

In certain preferred embodiments, when the recognition moiety is a carboxylic acid, the recognition moiety will interact with the analyte by complexation (e.g., metal ions). In still other preferred embodiments, the carboxylic acid will protonate a basic group on the analyte (e.g. amine).

In another preferred embodiment, the recognition moiety is a drug moiety. The drug moieties can be agents already accepted for clinical use or they can be drugs whose use is experimental, or whose activity or mechanism of action is under investigation. The drug moieties can have a proven action in a given disease state or can be only hypothesized to show desirable action in a given disease state. In a preferred embodiment, the drug moieties are compounds which are being screened for their ability to interact with an analyte of choice. As such, drug moieties which are useful in practicing the instant invention include drugs from a broad range of drug classes having a variety of pharmacological activities.

Classes of useful agents include, for example, non-steroidal anti- inflammatory drugs (NSAIDS). The NSAIDS can, for example, be selected from the following categories: (e.g., propionic acid derivatives, acetic acid derivatives, fenamic acid derivatives, biphenylcarboxylic acid derivatives and oxicams); steroidal anti-inflammatory drugs including hydrocortisone and the like; antihistaminic drugs (e.g., chlorpheniramine, triprolidine); antitussive drugs (e.g., dextromethorphan, codeine, carmiphen and carbetapentane); antipruritic drugs (e.g., methidilizine and trimeprizine); anticholinergic drugs (e.g., scopolamine, atropine, homatropine, levodopa); anti-emetic and antinauseant drugs (e.g., cyclizine, meclizine, chlorpromazine, buclizine); anorexic drugs (e.g., benzphetamine, phentermine, chlorphentermine, fenfluramine); central stimulant drugs (e.g., amphetamine, methamphetamine, dextroamphetamine and methylphenidate); antiarrhythmic drugs (e.g., propanolol, procainamide, disopyraminde, quinidine, encainide); β-adrenergic blocker drugs (e.g., metoprolol, acebutolol, betaxolol, labetalol and timolol); cardiotonic drugs (e.g., milrinone, amrinone and dobutamine); antihypertensive drugs (e.g., enalapril, clonidine, hydralazine, minoxidil, guanadrel, guanethidine); diuretic drugs (e.g., amiloride and hydrochlorothiazide); vasodilator drugs (e.g., diltazem, amiodarone, isosuprine, nylidrin, tolazoline and verapamil); vasoconstrictor drugs (e.g., dihydroergotamine, ergotamine and methylsergide); antiulcer drugs (e.g., ranitidine and cimetidine); anesthetic drugs (e.g., lidocaine, bupivacaine, chlorprocaine, dibucaine); antidepressant drugs (e.g., imipramine, desipramine, amitryptiline, nortryptiline); tranquilizer and sedative drugs (e.g., chlordiazepoxide, benacytyzine, benzquinamide, flurazapam, hydroxyzine, loxapine and promazine); antipsychotic drugs (e.g., chlorprothixene, fluphenazine, haloperidol, molindone, thioridazine and trifluoperazine); antimicrobial drugs (antibacterial, antifungal, antiprotozoal and antiviral drugs).

Antimicrobial drugs which are preferred for incorporation into the present composition include, for example, pharmaceutically acceptable salts of β-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, hexamidine isothionate, metronidazole, pentamidine, gentamycin, kanamycin, lineomycin, methacycline, methenamine, minocycline, neomycin, netilmycin, paromomycin, streptomycin, tobramycin, miconazole and amanfadine.

Other drug moieties of use in practicing the present invention include antineoplastic drugs (e.g., antiandrogens (e.g., leuprolide or flutamide), cytocidal agents (e.g., adriamycin, doxorubicin, taxol, cyclophosphamide, busulfan, cisplatin, α-2-interferon) anti-estrogens (e.g., tamoxifen), antimetabolites (e.g., fluorouracil, methotrexate, mercaptopurine, thioguanine).

The recognition moiety can also comprise hormones (e.g., medroxyprogesterone, estradiol, leuprolide, megestrol, octreotide or somatostatin); muscle relaxant drugs (e.g., cinnamedrine, cyclobenzaprine, flavoxate, orphenadrine, papaverine, mebeverine, idaverine, ritodrine, dephenoxylate, dantrolene and azumolen); antispasmodic drugs; bone-active drugs (e.g., diphosphonate and phosphonoalkylphosphinate drug compounds); endocrine modulating drugs (e.g., contraceptives (e.g., ethinodiol, ethinyl estradiol, norethindrone, mestranol, desogestrel, medroxyprogesterone), modulators of diabetes (e.g., glyburide or chlorpropamide), anabolics, such as testolactone or stanozolol, androgens (e.g., methyltestosterone, testosterone or fluoxymesterone), antidiuretics (e.g., desmopressin) and calcitonins).

Also of use in the present invention are estrogens (e.g., diethylstilbesterol), glucocorticoids (e.g., triamcinolone, betamethasone, etc.) and progenstogens, such as norethindrone, ethynodiol, norethindrone, levonorgestrel; thyroid agents (e.g., liothyronine or levothyroxine) or antithyroid agents (e.g., methimazole); antihyperprolactinemic drugs (e.g., cabergoline); hormone suppressors (e.g., danazol or goserelin), oxytocics (e.g., methylergonovine or oxytocin) and prostaglandins, such as mioprostol, alprostadil or dinoprostone, can also be employed.

Other useful recognition moieties include immunomodulating drugs (e.g., antihistamines, mast cell stabilizers, such as lodoxamide and/or cromolyn, steroids (e.g., triamcinolone, beclomethazone, cortisone, dexamethasone, prednisolone, methylprednisolone, beclomethasone, or clobetasol), histamine $H_2$ antagonists (e.g., famotidine, cimetidine, ranitidine), immunosuppressants (e.g., azathioprine, cyclosporin), etc. Groups with anti-inflammatory activity, such as sulindac, etodolac, ketoprofen and ketorolac, are also of use. Other drugs of use in conjunction with the present invention will be apparent to those of skill in the art.

When the recognition moiety is a chelating agent, crown ether or cyclodextrin, host-guest chemistry will dominate the interaction between the recognition moiety and the analyte. The use of host-guest chemistry allows a great degree of recognition-moiety-analyte specificity to be engineered into a device of the invention. The use of these compounds to bind to specific compounds is well known to those of skill in the art. See, for example, Pitt et al. "The Design of Chelating Agents for the Treatment of Iron Overload," In, INORGANIC CHEMISTRY IN BIOLOGY AND MEDICINE; Martell, A. E., Ed.; American Chemical Society, Washington, D.C., 1980, pp. 279–312; Lindoy, L. F., THE CHEMISTRY OF MACROCYCLIC LIGAND COMPLEXES; Cambridge University Press, Cambridge, 1989; Dugas, H., BIOORGANIC CHEMISTRY; Springer-Verlag, New York, 1989, and references contained therein.

Additionally, a manifold of routes allowing the attachment of chelating agents, crown ethers and cyclodextrins to other molecules is available to those of skill in the art. See, for example, Meares et al., "Properties of In Vivo Chelate-Tagged Proteins and Polypeptides." In, MODIFICATION OF PROTEINS: FOOD, NUTRITIONAL, AND PHARMACOLOGICAL ASPECTS;" Feeney, R. E., Whitaker, J. R., Eds., American Chemical Society, Washington, D.C., 1982, pp.370–387; Kasina et al. *Bioconjugate Chem.* 9:108–117 (1998); Song et al., *Bioconjugate Chem.* 8:249–255 (1997).

In a presently preferred embodiment, the recognition moiety is a polyaminocarboxylate chelating agent such as ethylenediaminetetraacetic acid (EDTA) or diethylenetriaminepentaacetic acid (DTPA). These recognition moieties can be attached to any amine-terminated component of a SAM or a spacer arm, for example, by utilizing the commercially available dianhydride (Aldrich Chemical Co., Milwaukee, Wis.).

In still further preferred embodiments, the recognition moiety is a biomolecule such as a protein, nucleic acid, peptide or an antibody. Biomolecules useful in practicing the present invention can be derived from any source. The biomolecules can be isolated from natural sources or can be produced by synthetic methods. Proteins can be natural proteins or mutated proteins. Mutations can be effected by chemical mutagenesis, site-directed mutagenesis or other means of inducing mutations known to those of skill in the art. Proteins useful in practicing the instant invention include, for example, enzymes, antigens, antibodies and receptors. Antibodies can be either polyclonal or monoclonal. Peptides and nucleic acids can be isolated from natural sources or can be wholly or partially synthetic in origin.

In those embodiments wherein the recognition moiety is a protein or antibody, the protein can be tethered to a SAM component or a spacer arm by any reactive peptide residue available on the surface of the protein. In preferred embodiments, the reactive groups are amines or carboxylates. In particularly preferred embodiments, the reactive groups are the ε-amine groups of lysine residues. Furthermore, these molecules can be adsorbed onto the surface of the substrate or SAM by non-specific interactions (e.g., chemisorption, physisorption).

Recognition moieties which are antibodies can be used to recognize analytes which are proteins, peptides, nucleic acids, saccharides or small molecules such as drugs, herbicides, pesticides, industrial chemicals and agents of war. Methods of raising antibodies for specific molecules are well-known to those of skill in the art. See, U.S. Pat. No. 5/147,786, issued to Feng et al. on Sep. 15, 1992; No. 5/334,528, issued to Stanker et al. on Aug. 2, 1994; No. 5/686,237, issued to Al-Bayati, M. A. S. on Nov. 11, 1997; and No. 5/573,922, issued to Hoess et al. on Nov. 12, 1996. Methods for attaching antibodies to surfaces are also art-known. See, Delamarche et al. *Langmuir* 12:1944–1946 (1996).

Peptides and nucleic acids can be attached to a SAM component or spacer arm. Both naturally-derived and synthetic peptides and nucleic acids are of use in conjunction with the present invention. These molecules can be attached to a SAM component or spacer arm by any available reactive group. For example, peptides can be attached through an amine, carboxyl, sulfhydryl, or hydroxyl group. Such a group can reside at a peptide terminus or at a site internal to the peptide chain. Nucleic acids can be attached through a reactive group on a base (e.g., exocyclic amine) or an available hydroxyl group on a sugar moiety (e.g., 3'- or 5'-hydroxyl). The peptide and nucleic acid chains can be further derivatized at one or more sites to allow for the attachment of appropriate reactive groups onto the chain. See, Chrisey et al. *Nucleic Acids Res.* 24:3031–3039 (1996).

When the peptide or nucleic acid is a fully or partially synthetic molecule, a reactive group or masked reactive group can be incorporated during the process of the synthesis. Many derivatized monomers appropriate for reactive group incorporation in both peptides and nucleic acids are know to those of skill in the art. See, for example, THE PEPTIDES: ANALYSIS, SYNTHESIS, BIOLOGY, Vol. 2: "Special Methods in Peptide Synthesis," Gross, E. and Melenhofer, J., Eds., Academic Press, New York (1980). Many useful monomers are commercially available (Bachem, Sigma, etc.). This masked group can then be unmasked following the synthesis, at which time it becomes available for reaction with a SAM component or a spacer arm.

In other preferred embodiments, the peptide is attached directly to the substrate. See, Frey et al. *Anal. Chem.* 68:3187–3193 (1996). In a particularly preferred embodiment, the peptide is attached to a gold substrate through a sulfhydryl group on a cysteine residue. In another preferred embodiment, the peptide is attached through a thiol to a spacer arm which terminates in, for example, an iodoacetamide, chloroacetamide, benzyl iodide, benzyl bromide, alkyl iodide or alkyl bromide. Similar immobilization techniques are known to those of skill in the art. See, for example, Zull et al. *J. Ind. Microbiol.* 13:137–143 (1994).

In another preferred embodiment, the recognition moiety forms an inclusion complex with the analyte of interest. In a particularly preferred embodiment, the recognition moiety is a cyclodextrin or modified cyclodextrin. Cyclodextrins are a group of cyclic oligosaccharides produced by numerous microorganisms. Cyclodextrins have a ring structure which has a basket-like shape. This shape allows cyclodextrins to include many kinds of molecules into their internal cavity. See, for example, Szejtli, J., CYCLODEXTRINS AND THEIR INCLUSION COMPLEXES; Akademiai Klado, Budapest, 1982; and Bender et al., CYCLODEXTRIN CHEMISTRY, Springer-Verlag, Berlin, 1978.

Cyclodextins are able to form inclusion complexes with an array of organic molecules including, for example, drugs, pesticides, herbicides and agents of war. See, Tenjarla et al., *J. Pharm. Sci.* 87:425–429 (1998); Zughul et al., *Pharm. Dev. Technol.* 3:43–53 (1998); and Albers et al., Crit. Rev. Ther. Drug Carrier Syst. 12:311–337 (1995). Importantly, cyclodextrins are able to discriminate between enantiomers of compounds in their inclusion complexes. Thus, in one preferred embodiment, the invention provides for the detection of a particular enantiomer in a mixture of enantiomers. See, Koppenhoefer et al. *J. Chromatogr. A* 793:153–164 (1998).

The cyclodextrin recognition moiety can be attached to a SAM component, through a spacer arm or directly to the substrate. See, Yamamoto et al., *J. Phys. Chem. B* 101:6855–6860 (1997). Methods to attach cyclodextrins to other molecules are well known to those of skill in the chromatographic and pharmaceutical arts. See, Sreenivasan, K. *J. Appl. Polym. Sci.* 60:2245–2249 (1996).

D. Mesogenic Layer

Any compound or mixture of compounds which forms a mesogenic layer can be used in conjunction with the present invention. The mesogens can form thermotropic or lyotropic liquid crystals. The mesogenic layer can be either continuous or it can be patterned.

As used herein, "thermotropic liquid crystal" refers to liquid crystals which result from the melting of mesogenic solids due to an increase in temperature. Both pure substances and mixtures form thermotropic liquid crystals.

"Lyotropic," as used herein, refers to molecules which form phases with orientational and/or positional order in a solvent Lyotropic liquid crystals can be formed using amphiphilic molecules (e.g., sodium laurate, phosphatidylethanolamine, lecithin).

Both the thermotropic and lyotropic liquid crystals can exist in a number of forms including nematic, chiral nematic, smectic, polar smectic, chiral smectic, frustrated phases and discotic phases.

As used herein, "nematic" refers to liquid crystals in which the long axes of the molecules remain substantially parallel, but the positions of the centers of mass are randomly distributed. Nematic crystals can be substantially oriented by a nearby surface.

"Chiral nematic," as used herein refers to liquid crystals in which the mesogens are optically active. Instead of the director being held locally constant as is the case for nematics, the director rotates in a helical fashion throughout the sample. Chiral nematic crystals show a strong optical activity which is much higher than can be explained on the bases of the rotatory power of the individual mesogens. When light equal in wavelength to the pitch of the director impinges on the liquid crystal, the director acts like a, diffraction grating, reflecting most and sometimes all of the light incident on it. If white light is incident on such a material, only one color of light is reflected and it is circularly polarized. This phenomenon is known as selective reflection and is responsible for the iridescent colors produced by chiral nematic crystals.

"Smectic," as used herein refers to liquid crystals which are distinguished from "nematics" by the presence of a greater degree of positional order in addition to orientational order; the molecules spend more time in planes and layers than they do between these planes and layers. "Polar smectic" layers occur when the mesogens have permanent dipole moments. In the smectic A2 phase, for example, successive layers show anti ferroelectric order, with the direction of the permanent dipole alternating from layer to layer. If the molecule contains a permanent dipole moment transverse to the long molecular axis, then the chiral smectic phase is ferroelectric. A device utilizing this phase can be intrinsically bistable.

"Frustrated phases," as used herein, refers to another class of phases formed by chiral molecules. These phases are not chiral, however, twist is introduced into the phase by an array of grain boundaries. A cubic lattice of defects (where the director is not defined) exist in a complicated, orientationally ordered twisted structure. The distance between these defects is hundreds of nanometers, so these phases reflect light just as crystals reflect x-rays.

"Discotic phases" are formed from molecules which are disc shaped rather than elongated. Usually these molecules have aromatic cores and six lateral substituents. If the molecules are chiral or a chiral dopant is added to a discotic liquid crystal, a chiral nematic discotic phase can form.

TABLE 1

$R^{11}$—⌬—$X^{11}$—⌬—$R^{21}$

| X | Name |
|---|---|
| —C=N— | Schiff bases |
| —N=N— | diazo compounds |
| —N=N→O | azoxy compounds |
| $\overset{H}{-C}=N\to O$ | nitrones |
| $\overset{H}{-C}=\overset{H}{C}-$ | stilbenes |
| —C≡C— | tolans |
| $-\overset{O}{\underset{\parallel}{OC}}-$ | esters |
| — | biphenyls |

Presently preferred mesogens are displayed in Table 1. In Table 1, $R^{11}$ and $R^{21}$ are independently selected R groups. Presently preferred R groups include, but are not limited to, alkyl groups, lower alkyl, substituted alkyl groups, aryl groups, acyl groups, halogens, hydroxy, cyano, amino, alkoxy, alkylamino, acylamino, thioamido, acyloxy, aryloxy, aryloxyalkyl, mercapto, thia, aza, oxo, both saturated and unsaturated cyclic hydrocarbons, heterocycles, arylalkyl, substituted aryl, alkylhalo, acylamino, mercapto, substituted arylalkyl, heteroaryl, heteroarylalkyl, substituted heteroaryl, substituted heteroarylalkyl, substituted heterocyclic, heterocyclicalkyl In a presently preferred embodiment, $X^{11}$ is a bond linking the two phenyl groups and the mesogen is a biphenyl. In another preferred embodiment $X^{11}$ is a C=N bond and the mesogen is a Schiff base. In still further preferred embodiments, $R^{11}$ and $R^{21}$ are independently selected from the group consisting of alkyl, alkoxy and cyano moieties.

In a particularly preferred embodiment, the mesogen is a member selected from the group consisting of 4-cyano4'-pentylbiphenyl, N-(4-methoxybenzylidene)-4-butlyaniline and combinations thereof.

The mesogenic layer can be a substantially pure compound, or it can contain other compounds which enhance or alter characteristics of the mesogen. Thus, in one preferred embodiment, the mesogenic layer further comprises a second compound, for example and alkane, which expands the temperature range over which the nematic and isotropic phases exist. Use of devices having mesogenic layers of this composition allows for detection of the analyte recognition moiety interaction over a greater temperature range.

In another preferred embodiment, the analyte first interacts with the recognition moiety and the mesogenic layer is introduced in its isotropic phase. The mesogenic layer is subsequently cooled to form the liquid crystalline phase. The presence of tie analyte within regions of the mesogenic layer will disturb the equilibrium between the nematic and isotropic phases leading to different rates and magnitudes of nucleation at those sites. The differences between the nematic and isotropic regions are clearly detectable.

D. Patterned Liquid Crystals

One approach to the patterning of the mesogenic layer on flat and curved surfaces is based on the use of patterned SAMs of molecules to direct both the polar (away from the surface) and azimuthal (in the plane of the surface) orientations of the mesogenic layer. This method is simple and flexible, and any of the recently established procedures for patterning SAMs on surfaces (for example, microcontact printing or photo-patterning) (Talov et al., *J. Am. Chem. Soc.* 115: 5305 (1993); Kumar et al., *Acc. Chem. Res.* 28: 219 (1995), and references therein; Xia et al., *J. Am. Chem. Soc.* 117: 3274 (1995), and references therein can be used; Jackman et al., *Science* 269: 664 (1995)). Using any of these methods, SAMs which pattern liquid crystals can be easily extended to sizes ranging from hundreds of nanometers (Xia et al., *J. Am. Chem. Soc.* 117: 3274 (1995), and references therein) to millimeters and permit both planar (parallel to the surface) and homeotropic (perpendicular to the surface) orientation of mesogenic layers; methods based on the rubbing of polymer films mainly provide manipulation of the in-plane alignment of mesogenic layers and cannot homeotropically align mesogenic layers. One class of useful SAMs has surface energies (~19 mJ/m$^2$) about half those of films of polyimides used for alignment of liquid crystals; low-energy surfaces are less prone to contamination by molecular adsorbates and dust particles than are high-energy ones. Because SAMs can also be patterned on non-planar surfaces (Jackman et al., *Science* 269: 664 (1995)), patterned mesogenic structures formed with SAMs can be replicated on curved surfaces.

The capacity to pattern mesogenic layer orientations on nonplanar surfaces provides procedures for the fabrication of tunable hybrid diffractive-refractive devices. For example, devices based on combinations of diffractive and refractive optical processes permit aplanatic or chromatic correction in lenses, spectral dispersion, imaging from a single optical element, and other manipulations of light (Resler et al., *Opt. Lett.* 21, 689 (1996); S. M. Ebstein, ibid., p. 1454; M. B. Stem, *Microelectron. Eng.* 32, 369 (1996): Goto et al., *Jpn. J. Appl. Phys.* 31, 1586 (1992); Magiera et al., *Soc. Photo-Opt. Instrum. Eng.*, 2774, 204 (1996)). The capability to pattern mesogenic layers on curved surfaces also provides routes for the fabrication of displays with wide viewing angles.

In a presently preferred embodiment, the tunable hybrid device permits the manipulation of light. In a further preferred embodiment, the device is a refractive-diffractive device. In a still further preferred embodiment, the device permits imaging from a single optical element. In yet another preferred embodiment, the device permits aplanatic or chromatic correction in lenses. In still another preferred embodiment, the device allows for spectral dispersion.

In another presently preferred embodiment, the SAM is layered on a material suitable for use as an electrode. In a preferred embodiment, the material is a metal film. In a further preferred embodiment, the metal film is a gold film.

The patterned mesogenic layers of the instant invention can be tuned by the use of electric fields. In a preferred embodiment, the electric field is used to reversibly orient the mesogenic layer. In a still further preferred embodiment, the electric field is applied either perpendicular to, or in the plane of, the surface of the mesogenic layer. In another preferred embodiment, the oriented mesogenic layer modulates the intensity of light diffracted from the layer.

The discussion above, concerning SAM components, SAM components with reactive groups and SAM components bearing recognition moieties is equally applicable in the context of this aspect of the invention. Thus, the constituents of the SAM can be chosen from any of a wide variety of appropriate molecules. In a presently preferred embodiment, the SAM comprises mixtures of $R^{21}CH_2(CH_2)_{14}SH$ and $R^{31}CH_2(CH_2)_{15}SH$, where $R^{21}$ and $R^{31}$ are independently members elected from the group consisting of hydrogen, reactive groups and recognition groups, as discussed above.

E. Analytes

The devices and methods of the present invention can be used to detect any analyte, or class of analytes, which interact with a recognition moiety in a manner that perturbs the mesogenic layer in a detectable manner. The interaction between the analyte and recognition moiety can be any physicochemical interaction, including covalent bonding, ionic bonding, hydrogen bonding, van der Waals interactions, repulsive electronic interactions, attractive electronic interactions and hydrophobic/hydrophilic interactions.

In a preferred embodiment, the interaction is an ionic interaction. In this embodiment, an acid, base, metal ion or metal ion-binding ligand is the analyte. In a still further preferred embodiment, the interaction is a hydrogen bonding interaction. In a particularly preferred embodiment, the hybridization of an immobilized nucleic acid to a nucleic acid having a complementary sequence is detected. In another preferred embodiment, the interaction is between an enzyme or receptor and a small molecule which binds thereto.

In another embodiment, the analyte competes for the recognition moiety with another agent which has been bound to the recognition moiety prior to introducing the analyte of interest. In this embodiment, it is the process or result of the analyte displacing the pre-bound agent which causes the detectable perturbation in the mesogenic layer. Suitable combinations of recognition moieties and analytes will be apparent to those of skill in the art.

In presently preferred embodiments, the analyte is a member selected from the group consisting of acids, bases, organic ions, inorganic ions, pharmaceuticals, herbicides, pesticides, chemical warfare agents, noxious gases and biomolecules. Importantly, each of these agents can be detected as a vapor or a liquid. These agents can be present as components in mixtures of structurally unrelated compounds, racemic mixtures of stereoisomers, non-racemic mixtures of stereoisomers, mixtures of diastereomers, mixtures of positional isomers or as pure compounds. Within the scope of the invention is a device and a method to detect a particular analyte of interest without interference from other substances within a mixture.

Both organic and inorganic acids can be detected using the device and method of the present invention. In a preferred embodiment, the recognition moiety comprises a group which is protonated by the acid. The result of this protonation is a detectable perturbation in the configuration of the mesogenic layer. While not wishing to be bound by any particular theory of operation, the inventors currently believe that this perturbation can be achieved by a change in the size or conformation of the recognition moiety on protonation. Alternatively, the protonation may induce repulsion between proximate recognition moieties bearing charges of the same sign. Further, the protonation can induce an overall positive charge across the SAM which perturbs the electronic distribution of the molecules in the mesogenic layer. This perturbation can be due to an electronic redistribution in the mesogenic molecules or can be due to repulsive or attractive interaction between a charged mesogen and a similarly, or oppositely, charged SAM.

In another preferred embodiment, the invention provides a device and a method for detecting bases. The methods for the detection and the mechanisms which allow such detection of bases are substantially similar to those discussed above in the context of acid detection; the notable exception being that the base will preferably deprotonate a group on a SAM component, spacer arm or substrate.

Organic ions which are substantially non-acidic and non-basic (e.g., quaternary alkylammonium salts) can be detected by a recognition moiety. For example, a recognition moiety with ion exchange properties is useful in the present invention. A specific example is the exchange of a cation such as dodecyltrimethylammonium cation for a metal ion such as sodium, using a SAM presenting. Recognition moieties that form inclusion complexes with organic cations are also of use. For example, crown ethers and cryptands can be used to form inclusion complexes with organic ions such as quaternary ammonium cations.

Inorganic ions such as metal ions and complex ions (e.g., $SO_4^{-2}$, $PO_4^{-3}$) can also be detected using the device and method of the invention. Metal ions can be detected, for example, by their complexation or chelation by agents bound to a SAM component, spacer arm or the substrate. In this embodiment, the recognition moiety can be a simple monovalent moiety (e.g., carboxylate, amine, thiol) or can be a more structurally complex agent (e.g., ethylenediamine-pentaacetic acid, crown ethers, aza crowns, thia crowns). The methods of detection and the mechanisms allowing such detection are substantially similar to those discussed in the context of acid detection.

Complex inorganic ions can be detected by their ability to compete with ligands for bound metal ions in ligand-metal complexes. When a ligand bound to a SAM component, a spacer arm or a substrate forms a metal-complex having a thermodynamic stability constant which is less than that of the complex between the metal and the complex ion, the complex ion will cause the dissociation of the metal ion from the immobilized ligand. The dissociation of the metal ion will perturb the mesogenic layer in a detectable manner. Methods of determining stability constants for compounds formed between metal ions and ligands are well known to those of skill in the art. Using these stability constants, devices which are specific for particular ions can be manufactured. See, Martell, A. E., Motekaitis, R. J., DETERMINATION AND USE OF STABILITY CONSTANTS, 2d Ed., VCH Publishers, New York 1992.

Small molecules such as pesticides, herbicides, agents of war, and the like can be detected by the use of a number of different recognition moiety motifs. Acidic or basic components can be detected as described above. An agent's metal binding capability can also be used to advantage, as described above for complex ions. Additionally, if these agents bind to an identified biological structure (e.g., a receptor), the receptor can be immobilized on the substrate, a SAM component or a spacer arm. Techniques are also available in the art for raising antibodies which are highly specific for a particular small molecule. Thus, it is within the scope of the present invention to make use of antibodies against small molecules for detection of those molecules.

In a preferred embodiment, the affinity of an analyte for a particular metal ion is exploited by having a SAM component, spacer arm or substrate labeled with an immobilized metal ion. The metal ion generally must have available at least one empty coordination site to which the analyte can bind. Alternatively, at least one bond between the metal and the metal-immobilizing agent must be sufficiently labile in the presence of the analyte to allow the displacement of at least one bond of the immobilizing reagent by the analyte In a preferred embodiment, the agent detected by binding to an immobilized metal ion is an organophosphorous compound such as an insecticide or an agent of war (e.g., VX, O-ethyl-S-(2-diisopropylaminoethyl)-methylthiophosphonate). Exemplary compounds which exhibit affinity for organophosphorous agents include, but are not limited to, $Cu^{+2}$-diamine, triethylentetraamine- $Cu^{+2}$-chloride, tetraethylenediamine-$Cu^{+2}$-chloride and 2,2'-bipyridine-$Cu^+_2$-chloride. See, U.S. Pat. No. 4/549,427, issued to Kolesar, Jr., E. S. on Oct. 29, 1985.

In another preferred embodiment, antibodies to the particular agents are immobilized on the substrate, a SAM component or a spacer arm. Techniques for raising antibodies to herbicides, pesticides and agents of war are known to those of skill in the art. See, Harlow, Lane, MONOCLONAL ANTIBODIES: A LABORATORY MANUAL, Cold Springs Harbor Laboratory, Long Island, N.Y., 1988.

In a preferred embodiment, the herbicides are preferably members of the group consisting of triazines, haloacetanilides, carbamates, toluidines, ureas, plant growth hormones and diphenyl ethers. Included within these broad generic groupings are commercially available herbicides such as phenoxyl alkanoic acids, bipyridiniums, benzonitriles, dinitroanilines, acid amides, carbamates, thiocarbamates, heterocyclic nitrogen compounds including triazines, pyridines, pyridazinones, sulfonylureas, imidazoles, substituted ureas, halogenated aliphatic carboxylic acids, inorganics, organometallics and derivatives of biologically important amino acids.

In the embodiments discussed above, the preferred agent of war is a member of the group consisting of mustard and related vesicants including the agents known as HD, Q, T, HN1, HN2, HN3, nerve agents, particularly the organic esters of substituted phosphoric acid including tabun, sarin, isopropyl methylphosphonofluoridate, soman pinacolyl methylphosphonofluoridate. Other detectable analytes include incapacitants such as BZ, 3-quinuclidinyl benzilate and irritants such as the riot control compound CS.

Pesticides preferred for detection using the present invention include bactericides (e.g, formaldehyde), fumigants (e.g., bromomethane), fungicides (e.g., 2-phenylphenol, biphenyl, mercuric oxide, imazalil), acaricides (e.g., abamectin, bifenthrin), insecticides (e.g., imidacloprid, pralletbrin, cyphenothrin)

The present invention also provides a device and a method for detecting noxious gases such as CO, $CO_2$, $SO_3$, $H_2SO_4$, $SO_2$, NO, $NO_2$, $N_2O_4$ and the like. In a preferred embodiment, the SAM, the substrate or a spacer arm includes at least one compound capable of detecting the gas. Useful compounds include, but are not limited to, palladium compounds selected from the group consisting of palladium sulfate, palladium sulfite, palladium pyrosulfite, palladium chloride, palladium bromide, palladium iodide, palladium perchlorate, palladium complexes with organic complexing reagents and mixtures thereof.

Other compounds of use in practicing this embodiment of the present invention include, molybdenum compounds such as silicomolybdic acid, salts of silicomolybdic acid, molybdenum trioxide, heteropolyacids of molybdenum containing vanadium, copper or tungsten, ammonium molybdate, alkali metal or alkaline earth salts of molybdate anion, heteropolymolybdates and mixtures thereof.

Still further useful gas detecting compounds include, copper salts and copper complexes with an available coordination site. Alpha-cyclodextrin, beta-cyclodextrin, modified alpha- and beta-cyclodextrins, gamma-cyclodextrin and mixtures thereof are of use in practicing the present invention. See, U.S. Pat. No. 5/618,493, issued to Goldstein et al. on Apr. 8, 1997 and No. 5/071,526, issued to Pletcher et al. on Dec. 10, 1991.

In another preferred gas detecting embodiment, the substrate, SAM component or spacer arm is derivatized with a compound selected from the group consisting of amorphous hemoglobin, crystalline hemoglobin, amorphous heme, crystalline heme and mixtures thereof. The heme serves as a recognition moiety which is reactive towards the gas. See, U.S. Pat. No. 3/693,327, issued to Scheinberg, I. A. on Sep. 26, 1972.

When the analyte is a biomolecule, any recognition moiety which interacts with the biomolecule is useful in practicing the present invention. Thus, when the analyte is a nucleic acid, in one embodiment, the recognition moiety is a nucleic acid having a sequence which is at least partially complementary to the recognition moiety sequence. When the recognition moiety is a peptide, an antibody specific for that peptide can be used as the analyte. In another preferred embodiment, a protein, other than an antibody (e.g., enzyme, receptor) is the analyte.

In a presently preferred embodiment, the recognition moiety interacts with biotin and is avidin or an anti-biotin antibody. Other recognition moieties of use when the analyte is a biomolecule will be apparent to those of skill in the art.

F. Compound Libraries

The synthesis and screening of chemical libraries to identify compounds which have novel pharmacological and material science properties is a common practice. Libraries which have been synthesized include, for example, collections of oligonucleotides, oligopeptides, small or large molecular weight organic or inorganic molecules. See, Moran et al., PCT Publication WO 97/35198, published Sep. 25, 1997; Baindur et al., PCT Publication WO 96/40732, published Dec. 19, 1996; Gallop et al., J. Med. Chem. 37:1233–51(1994).

Thus, in a fourth aspect, the invention provides a device for synthesizing and screening a library of compounds, comprising:

(1) a synthesis component, comprising:
  (a) a first substrate having a surface;
  (b) a self-assembled monolayer on said surface, said monolayer comprising a reactive functionality; and
(2) an analysis component, comprising:
  (a) a second substrate having a surface; and
  (b) a mesogenic layer between said surface of said first substrate and said surface of said second substrate.

In a preferred embodiment, the second substrate has a self-assembled monolayer attached thereto. In yet another preferred embodiment, the second substrate is permeable to liquids, vapors, gases and combinations thereof. The permeable substrate allows analytes to come into contact with the self-assembled monolayer(s) and the mesogenic layer, while maintaining the overall integrity of the optical cell.

The discussion above concerning substrates, organic layers and mesogenic layers is applicable to each of the embodiments of this aspect of the invention. In a presently preferred embodiment, the substrate comprises a metal film. In a further preferred embodiment, the metal film is a member selected from the group consisting of gold, nickel, platinum, silver, palladium and copper. In a still further preferred embodiment, the metal film is obliquely deposited.

The organic layer can be constructed of any organic substance which associates with the substrate, preferably, the organic layer constituents are moieties selected from the group consisting of alkanethiols, functionalized alkanethiols and combinations thereof. In a further preferred embodiment, at least one component of the organic layer is a moiety which is a member selected from the group consisting of $R^{21}CH_2(CH_2)_{14}SH$ and $R^{31}CH_2(CH_2)_{15}SH$, wherein $R^{21}$ and $R^{31}$ are independently members selected from the group consisting of hydrogen, reactive groups and recognition moieties.

The discussion above concerning reactive groups is equally applicable to this aspect of the invention. In certain preferred embodiments, $R^{21}$ and $R^{31}$ are independently members selected from the group consisting of hydrogen, amine, carboxylic acid, carboxylic acid derivatives, alcohols, thiols, alkenes and combinations thereof.

The SAM can be patterned by any of the above-discussed methods for producing patterned substrates and organic layers. The discussion above concerning the patterning of substrates and the construction of organic layers from a mixture of components having different properties is generally applicable to this embodiment of the invention. In a presently preferred embodiment, the SAM is patterned by microcontact printing. In a further preferred embodiment, the microcontact printing utilizes a component which is distinct from the components of the self-assembled monolayer.

The mesogenic layer can comprise one or more mesogenic compounds. The discussion above concerning the nature of the mesogenic layer is generally applicable to this embodiment of the invention. In a presently preferred embodiment, the mesogenic layer comprises a mesogen which is a member selected from the group consisting of 4-cyano-4'-pentylbiphenyl, N-(4-methoxybenzylidene)4-butylanailine and combinations thereof.

In another preferred embodiment, the present invention provides a method for synthesizing and analyzing a combinatorial library of compounds using the above described device. The method comprises,
  (a) adding a first component of a first compound to a first region of said surface of said first substrate and a first component of a second compound to a second region of said surface of said first substrate;
  (b) adding a second component of said first compound to said first region of said surface of said first substrate and adding a second component of said second compound to said second region on said surface of said first substrate;
  (c) reacting said first and second components to form a first product and a second product;
  (d) applying said mesogenic layer to said surface of said first substrate;
  (e) adding an analyte to said first region and said second region; and
  (f) detecting said switch in said mesogenic layer from a first orientation to said second orientation, whereby said analyzing is achieved.

The sequential addition of components can be repeated as many times as necessary in order to assemble the desired library of compounds. Additionally, any number of solvents, catalysts and reagents necessary to effect the desired molecular transformations can be added before, concurrently or after the addition of the component.

Virtually any type of compound library can be synthesized using the method of the invention, including peptides, nucleic acids, saccharides, small and large molecular weight organic and inorganic compounds.

In a presently preferred embodiment, when the synthesis is complete, a second substrate is layered on top of the mesogenic layer. In a further preferred embodiment, the second substrate has an attached second self-assembled monolayer contacts said mesogenic layer. The discussion above concerning the permutations available when two substrates are utilized is generally applicable to this embodiment. In a still further preferred embodiment, the second substrate is a permeable substrate. In yet another preferred embodiment, the second substrate is patterned similar to the first substrate.

In a presently preferred embodiment, the libraries synthesized comprise more than 10 unique compounds, preferably more than 100 unique compounds and more preferably more than 1000 unique compounds.

In a fifth aspect, the present invention also provides a library of compounds synthesized on a self-assembled monolayer. The discussion above concerning libraries, SAMs, functionalized SAM components, mesogenic layers, and the like is generally applicable to this aspect of the invention.

G. The Device

The device of the present invention can be of any configuration which allows for the support of a mesogenic layer on an organic layer. The only limitations on size and shape are those which arise from the situation in which the device is used or the purpose for which it is intended. The device can be planar or non-planar. Thus, it is within the scope of the present invention to use any number of polarizers, lenses, filters lights, and the like to practice the present invention.

Although many changes in the mesogenic layer can be detected by visual observation under ambient light, any means for detecting the change in the mesogenic layer can be incorporated into, or used in conjunction with, the device. Thus, it is within the scope of the present invention to use lights, microscopes, spectrometry, electrical techniques and the like to aid in the detection of a change in the mesogenic layer.

In those embodiments utilizing light in the visible region of the spectrum, the light can be used to simply illuminate details of the mesogenic layer. Alternatively, the light can be passed through the mesogenic layer and the amount of light transmitted, absorbed or reflected can be measured. The device can utilize a backlighting device such as that described in U.S. Pat. No. 5,739,879, issued to Tsai, T.-S on Apr. 14, 1998. Light in the ultraviolet and infrared regions is also of use in the present invention.

Microscopic techniques can utilize simple light microscopy, confocal microscopy, polarized light microscopy, atomic force microscopy (Hu et al., *Langmuir* 13:5114–5119 (1997)), scanning tunneling microscopy (Evoy et al., *J. Vac. Sci. Technol A* 15:1438–1441, Part 2 (1997)), and the like.

Spectroscopic techniques of use in practicing the present invention include, for example, infrared spectroscopy (Zhao et al., *Langmuir* 13:2359–2362 (1997)), raman spectroscopy (Zhu et al., *Chem. Phys. Lett.* 265:334–340 (1997)), X-ray photoelectron spectroscopy (Jiang et al., *Bioelectroch. Bioener.* 42:15–23 (1997)) and the like. Visible and ultraviolet spectroscopies are also of use in the present invention.

Other useful techniques include, for example, surface plasmon resonance (Evans et al., *J. Phys. Chem. B* 101:2143–2148 (1997), ellipsometry (Harke et al., *Thin Solid Films* 285:412–416 (1996)), impedometric methods (Rickert et al., *Biosens. Bioelectron.* 11:757:768 (1996)), and the like.

In a presently preferred mode of using the device of the present invention, the optical cell comprises two substrates that are spaced from about 10 micrometers to about 10 millimeters apart, preferably from about 20 micrometers to about 5 millimeters apart, more preferably from about 50 micrometers to about 0.5 millimeters apart. In this embodiment, the analyte is drawn into the optical cell by any of a number of techniques including, but not limited to, capillarity, electroosmosis, electophoresis, and centrifugation. Once the analyte has entered the optical cell, it is then displaced by drawing a mesogenic phase into the cell.

In yet another preferred embodiment, the optical cell (i.e., substrate) is of approximately cylindrical cross-section and the recognition moieties are attached to the inner surface of the cylinder.

In a seventh aspect, the invention provides a low energy surface having a mesogenic layer anchored planarly thereon. Low energy surfaces offer the advantage of being easy to clean. Thus, devices constructed from these surfaces have fewer defects and will display enhanced optical proerties.

In an eighth aspect, the invention provides a method for controlling tilt in an organic layer comprising a haloorganosulfur moiety, having a halogen content, adsorbed onto a substrate, the method comprising selecting the halogen content of the haloorganosulfur. In a preferred embodiment, the tilt is selected to provide a desired optical texture in a mesogenic layer.

Thus, in another aspect, the invention provides a method for varying the optical texture of a mesogenic layer comprising a haloorganosulfur. The haloorganosulfur has a halogen content. The optical texture of the mesogenic layer is controlled by selecting the halogen content of the haloorganosulfur.

Other techniques and devices of use in the present invention will be apparent to those of skill in the art.

The following examples further illustrate the invention and should not be construed as further limiting. The contents of all references, patents and patent applications cited throughout this application are expressly incorporated by reference.

EXAMPLES

The detailed examples which follow illustrate the device and methods of the invention as applied to amplifying, and transducing into an optical signal, the interaction of a recognition moiety hosted in a self-assembled monolayer and an analyte which interacts with the recognition moiety.

Example 1 illustrates the use of SAMs bearing biotin to detect avidin and an anti-biotin antibody (goat anti-biotin). The binding of avidin or an antibody to the biotin produces a marked change in the appearance of the mesogenic layer which allows the presence of both the avidin and anti-biotin to be detected by visual inspection.

Example 2 illustrates the use of a SAM bearing a carboxylic acid recognition moiety to detect the presence of hexylamine vapor. Similar to the results in example 1, the binding of the analyte to the recognition moiety produced a marked change in the appearance of the mesogenic layer, which could be visually detected.

Example 3, illustrates that the orientation of a mesogenic layer is dependent on the ionization state and pKa of acidic recognition moieties on the SAM components. The liquid crystal used in Example 3 is a nematic liquid crystal and the SAM is formed from ($\omega$-mercaptoundecanoic acid.

Example 4 illustrates the quantitative detection of metal ions by their binding to SAMs with carboxylic acid terminal groups. Similar to the examples above the binding is amplified and transduced into an optical signal.

Example 5 demonstrates the patterning of SAMs on a substrate. Further, Example 5 demonstrates that the anchoring orientation of a mesogenic layer can be controlled by the nature of the SAM components and the features of the pattern.

Example 6 demonstrates that the anchoring of mesogneic layers can be varied by using surfaces comprising fluorinated organosulfur compounds.

EXAMPLE 1

Example 1 illustrates the amplification and transduction into optical outputs of receptor-mediated binding of proteins at surfaces. Spontaneously organized surfaces hosting ligands were designed so that protein molecules, upon binding to the ligands triggered changes in 1- to 20-micrometer thick films of supported liquid crystals.

Surfaces were designed with nanometer-scale topographies that could be erased by the specific binding of a protein to surface-immobilized ligands (FIG. 1A), thus leading to macroscopic changes in the orientations of liquid crystals supported on these surfaces. First, thin fins of polycrystalline gold were prepared (FIG. 1B) with roughnesses characterized by a maximum amplitude of $\approx$2 nm and a maximum wavelength of $\approx$50 nm (FIG. 1C). The deposition of the gold films was controlled so as to introduce an anisotropic roughness within the films (called hereafter "anisotropic gold films (V. K. Gupta et al., *Langmuir* 12, 2587 (1996)). Although subtle, the anisotropic roughness was easily detected by observing the orientations of supported liquid crystals (V. K. Gupta et al., *Langmuir* 12, 2587 (1996)). Second, mixed, self-assembled monolayers (SAMs) were formed from Biotin-$(CH_2)_2[(CH_2)_2O]_2NHCO(CH_2)_{11}SH$ (BiSH) (J. Spinke et al., *J. Chem. Phys.* 99, 7012 (1993)) and $CH_3(CH_2)_7SH$ ($C_8SH$) by immersion of the films of anisotropic gold in ethanolic solutions containing 9.6 $\mu$M of BiSH and 70.4 $\mu$M of $C_8SH$ for 8 hours (Mixed SAMs were also formed in a few minutes by using solutions that contained millimolar concentrations of the organothiols). The mixed SAMs were estimated to consist of 27% biotinylated species by linear interpolation of thicknesses ($\Delta$) of single component SAMs formed from BiSH ($\Delta_{BiSH}$=3.8 nm) and $C_8SH$ ($\Delta_{C8SH}$=1 nm) (All thickness measurements were performed using a Rudolph Auto ellipsometer with light (633 nm) incident at an angle of 70°. A refractive index of 1.45 was used to estimate the thickness of bound layers of thiols and proteins. Standard deviations of ellipsometric thicknesses (Δ) reported in this paper are +/−0.2 nm). Binding of the protein avidin (Av, 4.2 nm×4.2 nm×5.6 nm) (P. C. Weber et al., *Science*, 243, 85 (1989)) to biotin hosted within these SAMs was achieved by incubating the SAMs for 10–15 minutes in phosphate-buffered saline (PBS) (pH 7.4, 100 mM NaCl, 0.004% by volume Triton X-100) containing 0.5 μM of Av (K. L. Prime et al., *J. Am. Chem. Soc.* 115, 10714 (1993)). The surfaces were then rinsed in deionized water for ~30 seconds and dried with a stream of nitrogen for ~30 seconds. To form liquid crystal cells, two SAMs were spaced apart using thin plastic film Mylar™ or Saranwrap™) and then secured using paper clips (FIG. 2). Using capillarity, a drop of 4-cyano-4'-pentylbiphenyl (5CB) was drawn in its isotropic phase (isotropic-nematic transition ~34° C.) into the cavity formed by the two surfaces. The liquid crystal was then cooled towards room temperature: a nematic texture was observed to spread across a 1 cm×1 cm-sized cell in ~5–10 seconds. Optical images of the cell were recorded on a polarization microscope using transmission mode.

When two mixed SAMs supported on anisotropic gold films were paired to form a liquid crystal cell, the polarized light image of the liquid crystal cell was uniform and featureless (FIG. 3A). The liquid crystal within the cell was, therefore, uniformly oriented (FIG. 2A). When a second liquid crystal cell was prepared using mixed SAMs that were pretreated with PBS containing Av prior to filling with liquid crystal ($\Delta_{Av}$=2.6 nm), the polarized light image was highly non-uniform and colored (FIG. 3B). The orientation of the liquid crystal showed no memory of the anisotropic roughness of the gold film (When rotated between crossed polars, the intensity of light transmitted through the sample did not show a large modulation in intensity. This result indicates the absence of a preferred orientation of the liquid crystal within the cell. The general features of the optical textures were not influenced by variations in rates of cooling of the liquid crystal to the ambient temperature) and resembled optical images of liquid crystal supported on mixed SAMs formed on gold films with no anisotropic roughness (FIG. 3C). In contrast, the liquid crystal remained uniformly oriented when mixed SAMs were pretreated with PBS containing Av blocked with biotin (100-fold excess) ($\Delta_{blkd\ Av}$=0.9 nm, FIG. 3D) or a SAM formed from $C_8SH$ that was pretreated in PBS containing Av ($\Delta_{Av}$=0.4 nm) (K. L. Prime et al., *J. Am. Chem. Soc.* 115, 10714 (1993)). Therefore, specific binding of Av to mixed SAMs erases the effect of the nanometer-scale, anisotropic roughness of the gold on the orientation of the bulk liquid crystal and thus leads to a readily visualized change in the optical texture of the liquid crystal cell. It was estimated that within a 1 mm² area of the mixed SAM (an easily visible area), ~$10^{10}$ Av molecules (~1 ng or ~2.6 nm of coverage) control the orientations of ~$2\times10^{15}$ mesogens (a 2 μm-thick film of liquid crystal). The binding of each Av molecule to the surface is, therefore, amplified into a reorientation of >$10^5$ mesogens. Because less than half a monolayer of Av can change the orientation of the liquid crystal, and because liquid crystal films as thick as 100 μm can be oriented by surfaces, higher levels of amplification are possible (it has been demonstrated that specific binding of Av can cause reorientation of films of liquid crystals as thick as 20 μm (~$2\times10^6$ mesogens/protein).

Because the binding of Av to biotin is unusually strong for a protein-ligand interaction (dissociation constant, $K_d\sim10^{-15}$ M), the use of liquid crystals to detect the binding of antibodies to antigens ($K_d 10^{-9}$ M) was also demonstrated (H. Bagci et al., *FEBS*, 322, 47 (1993)). For example, the binding of affinity isolated, goat anti-biotin antibody (anti-Bi IgG) (Anti-Bi IgG was purchased from Sigma BioScience and antiFITC IgG was purchased from Molecular Probes. All measurements were performed in PBS containing 0.5 μM anti-Bi IgG and 0.004% Triton X-100. After binding the IgG in PBS, the samples were rinsed with deionized water and dried under a stream of nitrogen) to a mixed SAM formed from BiSH and $C_8SH$ ($\Delta_{anti-Bi\ IgG}$=5.5 nm) caused the orientation of a supported liquid crystal to become non-uniform (FIG. 3E). In contrast, neither a non-specific antibody such as rabbit polyclonal anti-fluorescein antibody (anti-FITC IgO, $\Delta_{anti-FITC\ IgC}$=0 nm) (FIG. 3F) nor bovine serum albumin (BSA, ΔBSA=1.4 nm) (the optical texture was the same as FIG. 3F) caused a change in the orientation of the liquid crystal. In addition, a SAM formed from $C_8SH$ did not significantly bind anti-Bi IgG ($\Delta_{anti-Bi\ IgG}$=0.1 nm) and thus oriented 5CB uniformly (the optical texture was the same as FIG. 3F).

The results above demonstrate two further principles. First, it is possible to control the anisotropy within gold films so that the immobilization of ligands (such as BiSH) on these surfaces does not disturb the uniform orientation of the liquid crystal prior to binding of proteins. Oligopeptides (e.g., Ala-Ala-Pro-Phe) have also been introduced into SAMs without disturbing the uniform orientation of liquid crystals (Uniform anchoring of nematic 5CB was measured on mixed SAMs formed on anisotropic gold films by coadsorption from an ethanolic solution of 9 mM $C_{11}SH$ and 1 mM $HS(CH_2)_{11}$-Ala-Ala-Pro-Phe-pNA, where Ala is alanine, Pro is proline, Phe is phenylalanine and pNA is p-nitroanilide.).

Second, the roughness of the gold film used in these experiments was such that the threshold surface concentration of Av or anti-Bi IgG needed to change the orientation of 5CB was greater than the level of non-specific adsorption but less than specific adsorption. This characteristic makes possible a sandwich-type assay in which a capture protein (macromolecular ligand) is supported on a surface, and the binding of a second protein (e.g., detecting antibody) to the capture protein is detected by a change in orientation of the liquid crystal. To demonstrate this principle, a mixed SAM was first treated with fluorescein-labeled avidin (FITC-Av) for 10 minutes (Fluorescein-labeled streptavidin (FITC-Av) was purchased from Pierce. All measurements were performed in PBS containing 0.5 μM FITC-Av and 0.004% Triton X-100. After binding the FITC-Av in PBS, the samples were rinsed with deionized water.). The bound FITC-Av ($\Delta_{FITC-Av}$=1 nm) was below the threshold required to trigger a change in the orientation of 5CB (FIG. 3G). The SAM supporting the bound FITC-Av was immersed into a solution of 0.5 μM anti-FITC IgG in PBS. The ellipsometric thickness of the bound protein after the second step was 3.5 nm and thus sufficient to trigger a change in the orientation of the liquid crystal (FIG. 3H). Anti-FITC IgG did not bind to a mixed SAM in the absence of bound FITC-Av ($\Delta_{anti-FITC\ IgG}$=−0.1 nm) nor did anti-FITC IgG blocked with fluorescein bind to a surface presenting FITC-Av ($\Delta_{FITC-Av/anti-FITC\ IgG}$=0.7 nm): both control experiments produced uniformly oriented liquid crystals (FIG. 3F and 3I).

By repeating the above experiments using Av, and by binding anti-Av IgG to an antigenic epitope on Av, concentrations of anti-Av IgG in solution as low as 2.3 nM have been detected (Studies based on stress-induced chromatic transitions in polymer films have reported limits of detection for specific binding of pentavalent cholera toxin to ganglioside $G_{M1}$ (molecular weight ~$10^5$ Da, $K_d$~$10^{-10}$ M) to be 100 ppm (~1 μM) when using liposomes in solution and 20 ppm (~0.2 μM) when using supported films of the polymer (D. Charych et al, *Science* 261, 585 (1993); D. Charych et al, *Chem & Biol* 3, 113 (1996); J. Pan et al., 13, 1365 (1997)).

Figure 4B:
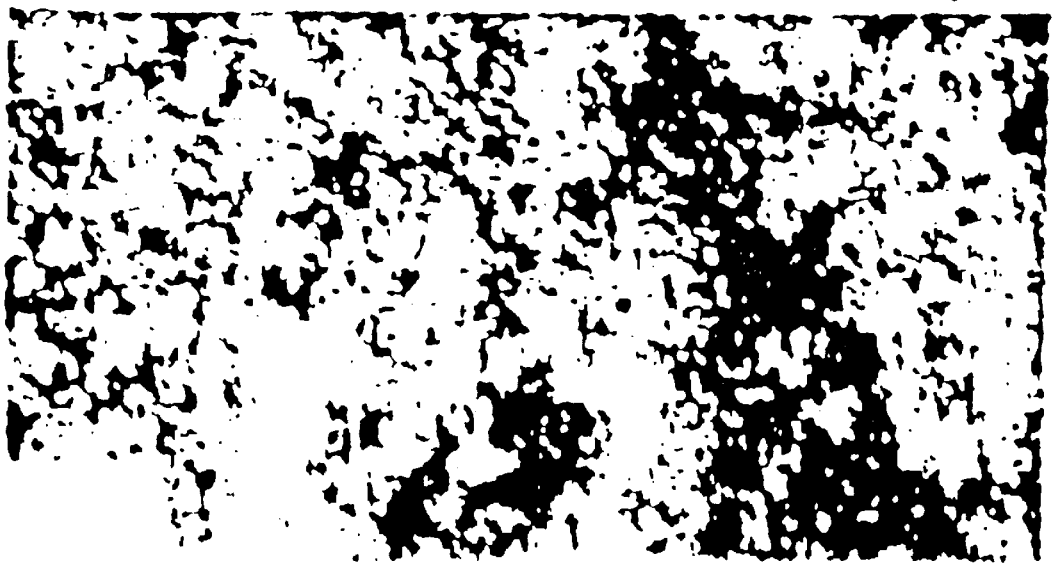
FIG. 4B displays an optical image (parallel polarizers) of largely untwisted LC formed between a mixed SAM pretreated with Av in PBS and a SAM formed from $C_{15}SH$. The image is bright because the polarization of light transmitted through the LC was not rotated and thus light was transmitted by the analyzer. We observed LC cells to be dark (parallel polarizers) when mixed SAMs were pretreated with blocked Av or BSA. The films of LC were 20 μm thick. The horizontal dimension in each image is 440 μm.
Figure 4A:
FIG. 4A displays an optical image through parallel polarizers of a TNLC (see FIG. 2B) formed between a SAM prepared from $C_8SH$ and a mixed SAM prepared from BiSH and $C_8SH$. The SAMs were supported on anisotropic gold films (the preferred direction of the gold was parallel on the two surfaces). The image is dark because the polarization of light transmitted through the TNLC was rotated by 90° and thus light was extinguished by the analyzer.
Figure 5A:
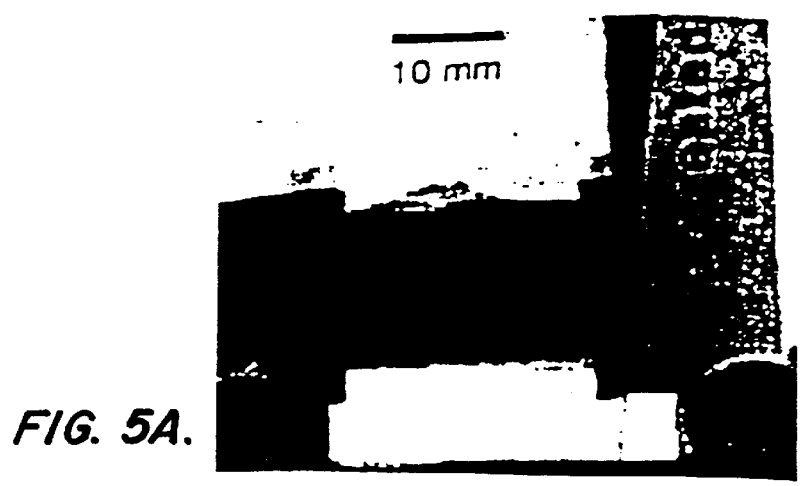
FIGS. 5A and 5B are optical images of LC sandwiched between two gold films, one supporting a SAM formed from $C_{15}SH$ and the other patterned with a mixed SAM formed from $C_8SH$ and BiSH and a SAM formed from $C_{16}SH$.
Figure 5B:
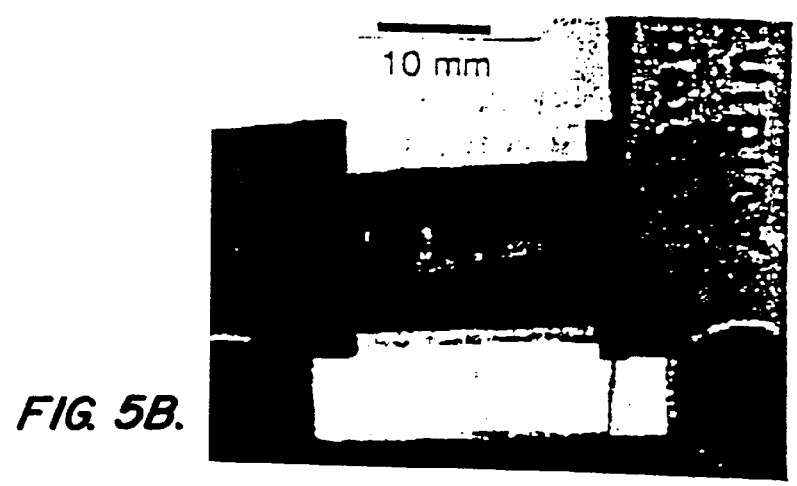
Figure 5C:
FIGS. 5C and 5D are optical images (parallel polarizers) of LC sandwiched between two gold films, one supporting a SAM formed from $C_{15}SH$ and the other supporting a grating-like pattern of SAMs formed from $C_{16}SH$ and a mixture of $C_8SH$ and BiSH. Patterned SAMs are shown without bound Av (C) and pretreated with Av in PBS (D).
Figure 5D:
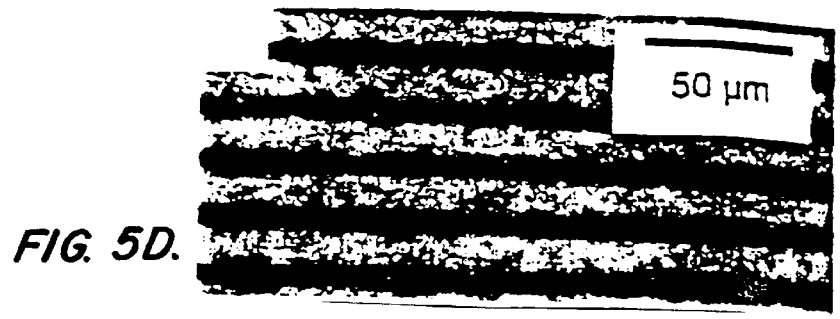
Figure 5E:
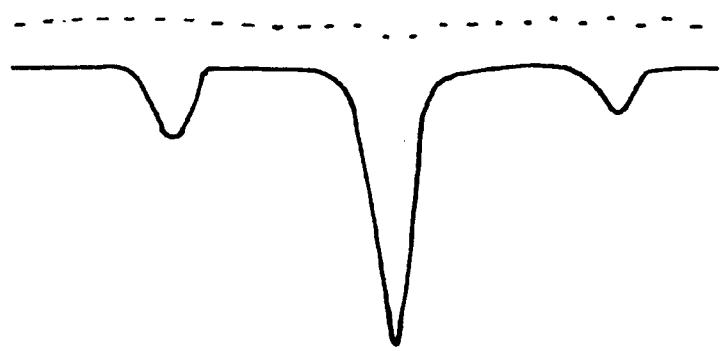
FIG. 5E is a diffraction pattern formed by laser light incident on the LC cell shown in (C) (dashed line) and (D) (solid line). The cells were held between parallel polarizers, and the spatial variation of the intensity of light in the diffraction pattern was obtained from a digital image of the pattern. The LC layers were 20 μm thick.
Figure 19E:
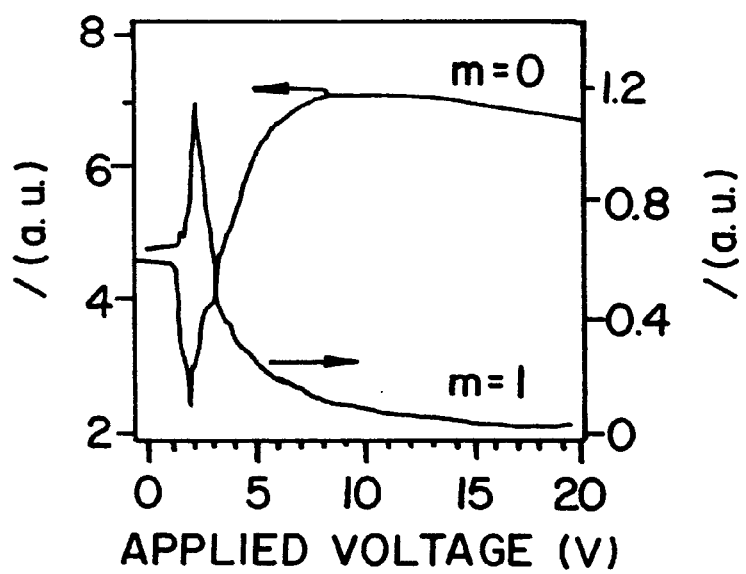
FIG. 19 displays optical images of gratings when illuminated with light with polarization either along the x or y direction and change in intensity of diffraction spots upon application of an electric field.

Twisted nematic liquid crystals (TN liquid crystals) are widely used in flat panel displays because reorientation of the twisted liquid crystal by an electric field provides high optical contrast ratios (The surfaces of a TNliquid crystal cell are designed such that the region of liquid crystal in contact with one surface is oriented at right angles to the region of liquid crystal in contact with the opposing surface (FIG. 2B). The liquid crystal sandwiched between the two surface regions of the cell undergoes a 90° twist-type deformation, and the polarization of linearly polarized light transmitted through such a cell is rotated by 90°. A twisted liquid crystal cell, when viewed between two parallel-polarizers, appears dark. In contrast, a cell containing liquid crystal that is not twisted appears bright between parallel polars (Liquid crystals: APPLICATIONS AND USES, B. Bahadur, Ed. (World Scientific, Singapore, 1990).). TNliquid crystals were also used to enhance the optical transduction of biotin-mediated binding of avidin to surfaces (FIG. 4). Optical read-out of the binding of proteins and ligands at surfaces can be further facilitated by using patterned SAMs (A. Kumar, et al., *Acc. Chem. Res.* 28,219 (1995), V. K. Gupta et al., *Science* 276, 1533 (1997)). Surfaces were designed such that binding of Av to biotin-derivatized regions of a patterned SAM caused area-specific untwisting of a TNliquid crystal cell (FIG. 5). Patterns so formed with sizes of a few centimeters provide an easily read indicator of the presence of a biomolecule in solution (FIG. 5A and 5B). By using micrometer-sized patterns, it was also demonstrated that the binding of biomolecules at surfaces can be detected optically by the diffraction of light from periodic liquid crystal structures which form only when the biomolecules are bound to the surfaces (FIG. 5C–E).

EXAMPLE 2

The following example illustrates the use of a SAM functionalized with a carboxylic acid moiety to detect the presence of hexylamine vapor.

Liquid crystals supported on surfaces can be used to detect the presence of small organic molecules (e.g., airborne pollutants such as hexylamine) or ions (e.g., heavy metals). The following experiment was designed to explore the effect of a relatively simple, in situ change in the structure of a surface (i. e.,transformation of a carboxylic acid into a amine salt) on the orientation of a supported liquid crystal.

The model system used comprised a 4-cyano-4'-pentylbiphenyl (5CB) liquid crystal supported on SAMs formed from $HS(CH_2)_{10}COOH$ on obliquely deposited films of gold. n-Hexylamine was used as a model small organic molecule. The amine was introduced into the liquid crystal device in the vapor phase.

Experiments were performed to determine whether the reorientation of a 5CB liquid crystal supported on monolayers terminated with carboxylic acid in the presence of vapor phase n-hexylamine was truly a surface induced phenomena. Our experiments compared 5CB orientation on 2 different monolayers (each exhibiting different surface functional groups) within the same n-hexylamine atmosphere. One surface was the $HS(CH_2)_{10}COOH$ monolayer. In the present example, the COOH terminal group is shown to interact with n-hexylamine and induce a reorientation of 5CB. The other monolayer was formed from $HS(CH_2)_{15}CH_3$ which terminates in a methyl group. The methyl group is, unreactive towards n-hexylamine.

Figure 6:
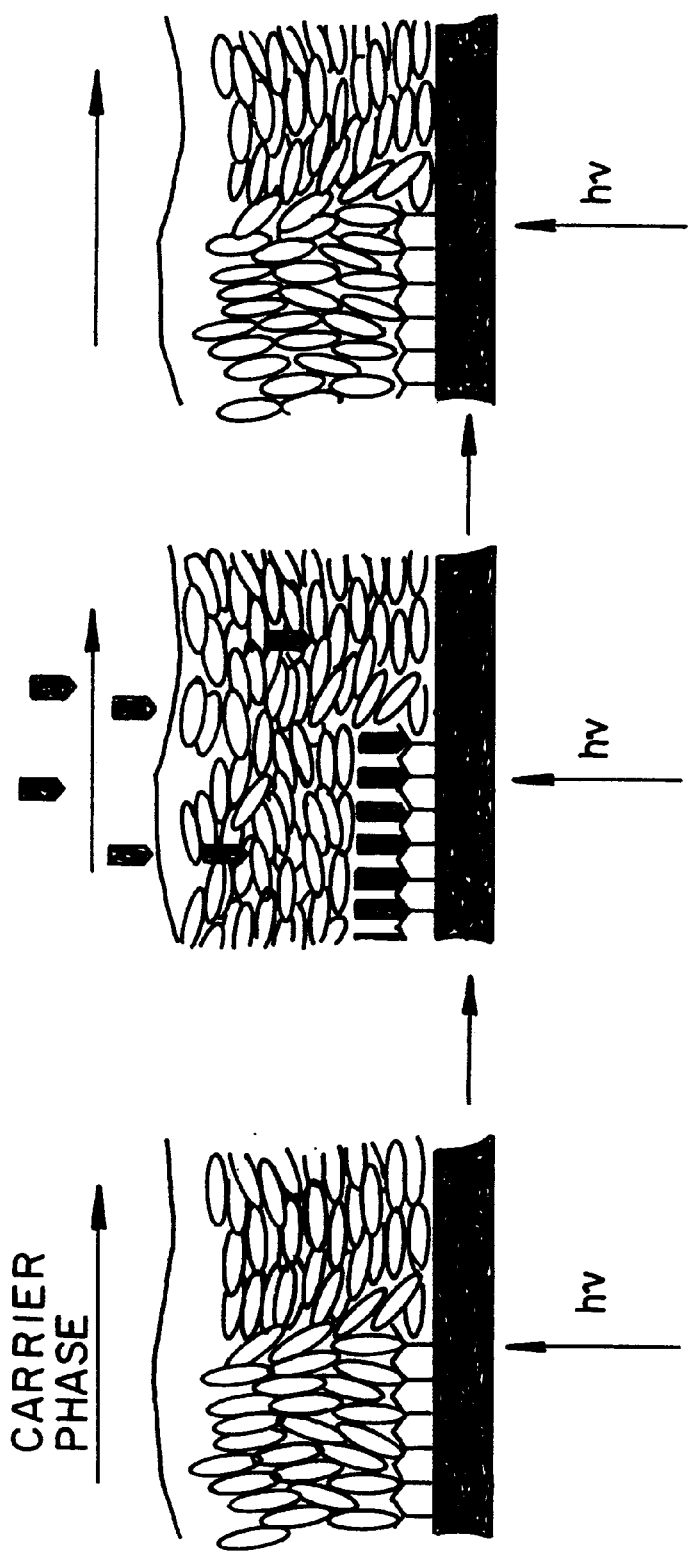
FIG. 6 is an illustration for an in situ, sensor where transitions in orientations of liquid crystal caused by small organic molecules at surfaces transduce molecular events into bulk phenomena.
Figure 7A:
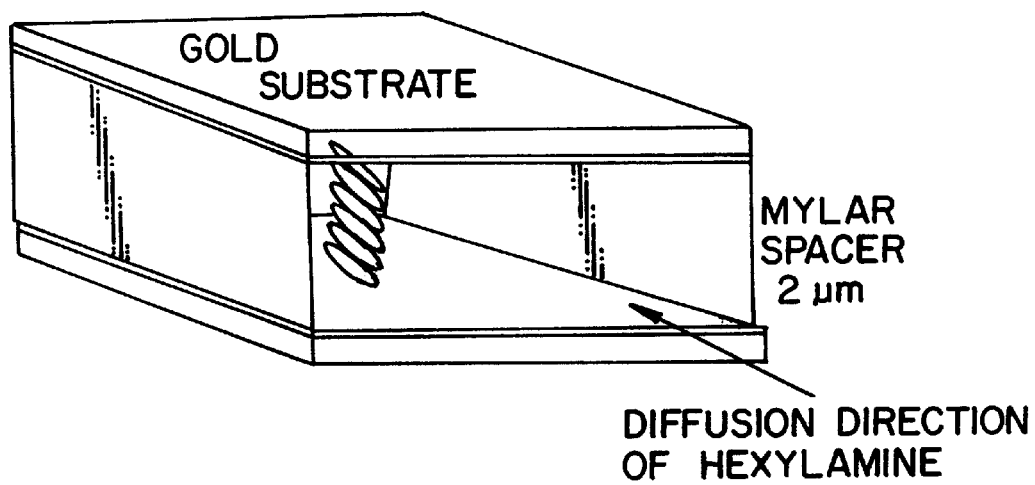
FIG. 7A is a schematic drawing of the direction of diffusion into an optical cell in a hexylamine atmosphere filled with 5CB supported on a SAM formed from $HS(CH_2)_{10}COOH$.
Figures 7B, 7C, 7D:
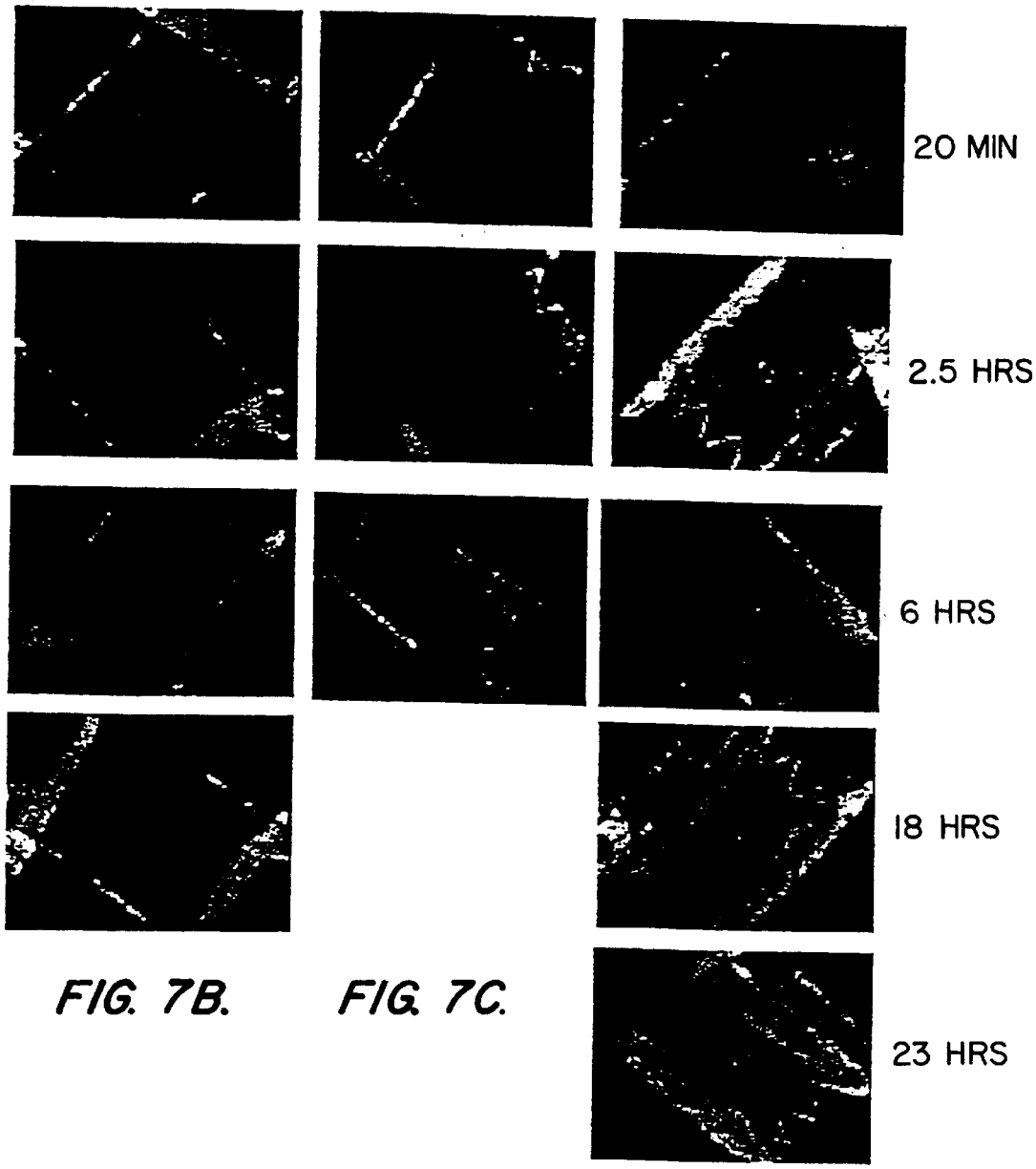
FIG. 7B is a control experiment of 5CB supported on a SAM formed from $HS(CH_2)_{15}CH_3$ within an optical cell.
FIG. 7C is a 5CB orientation on a SAM formed from $HS(CH_2)_{10}COOH$ within an optical cell in a hexylamine atmosphere<<1 vol %.
FIG. 7D displays a transition in 5CB orientation on a SAM formed from $HS(CH_2)_{10}COOH$ within an optical cell in a hexylamine atmosphere of approximately 1 vol %.

Optical cells were formed with SAMs of $HS(CH_2)_{10}COOH$ or $HS(CH_2)_{15}CH_3$ and subsequently filled with 5CB. FIG. 6 illustrates a scheme for an in situ sensor, wherein the transitions in orientations of the mesogenic layer caused by small molecules at surfaces transduce molecular events into bulk phenomena. FIG. 7a illustrates the schematic of vapor diffusion of n-hexylamine into these optical cells. FIG. 7b and 7c,d show photographs of these optical cells in a n-hexylamine atmosphere over time. No change in the 5CB orientation was observed for cell with the SAM formed from $HS(CH_2)_{15}CH_3$. All the images show that the cell is dark. However, as shown in FIG. 7d, a drastic change in the orientation of 5CB was observed traveling from the edge of the cell inwards as time progressed. The edge of the optical cell was no longer dark and the thickness increases with time.

Figures 8A, 8B:
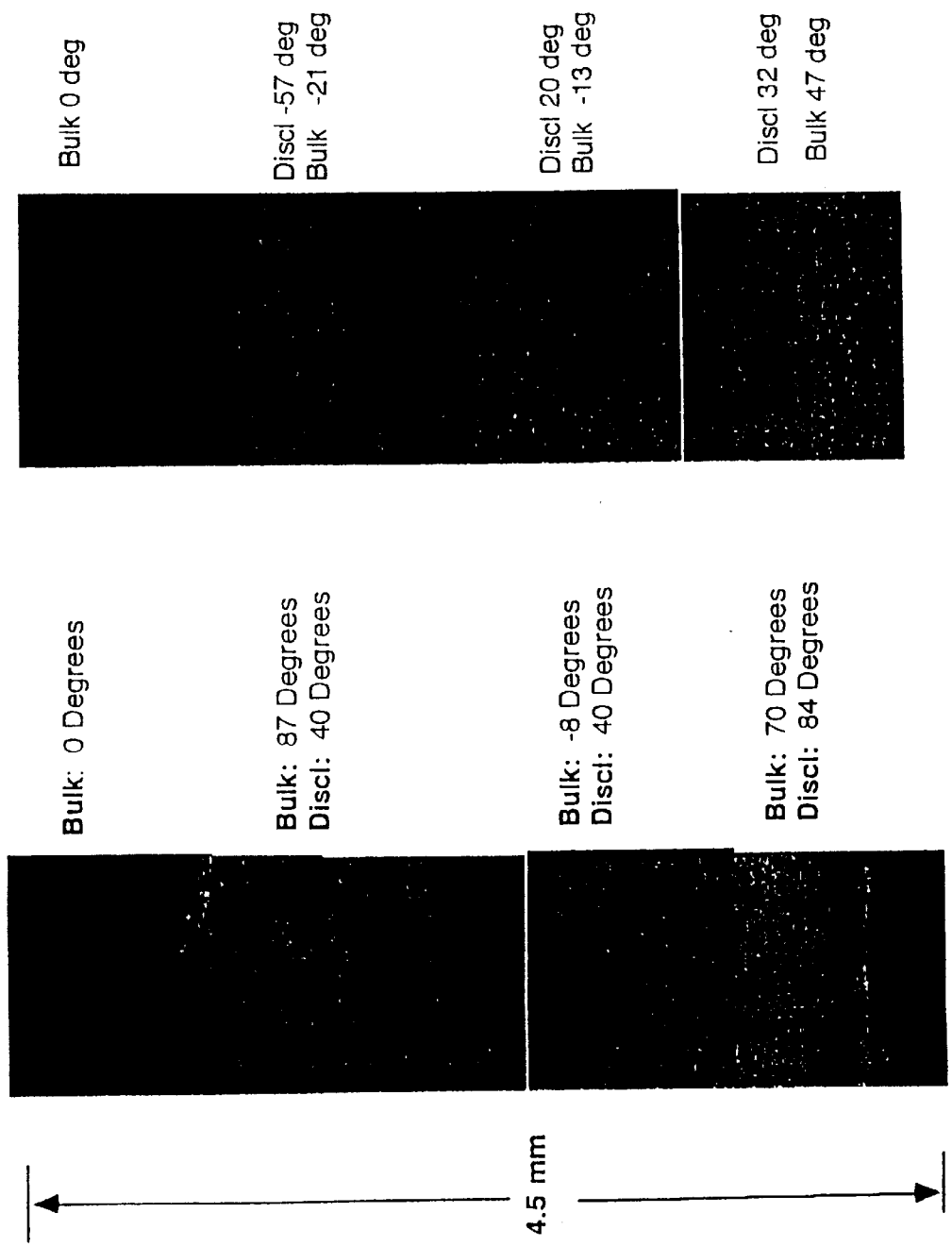
FIG. 8A displays a 5CB domain structure 8 hours after initial exposure.
FIG. 8B displays a domain structure after 19 hours.

The cell photographed in FIG. 7c was exposed to a very low vapor concentration of n-hexylamine while the cell in FIG. 7d was exposed to higher vapor concentrations. FIG. 8 demonstrates the effect of exposing the device to hexylamine over time. The cells shown in FIG. 8a are shown 8 hours after initial exposure. The cells in FIG. 8b are shown 19 hours after exposure.

These experiments indicate the change in 5CB orientation is induced by an interaction between the carboxylic acids at the surface of the SAM and the vapor phase analyte, hexylamine.

EXAMPLE 3

Example 3 illustrates the pH-dependent orientations of liquid crystals supported on self-assembled monolayers. The liquid crystal used in Example 3 is a nematic liquid crystal. The self-assembled monolayer is formed from ω-mercaptoundecanoic acid.

3.1 Materials $HS(CH_2)_{10}COOH$ was synthesized using published methods and characterized by NMR spectroscopy (MP 46.5–47° C). The liquid crystals tested, 5CB (K15, BDH, $T_{ni}$=34.5° C.) and MBBA (TCI and Aldrich $T_{ni}$=40° C.) have a nematic phase at room temperature.

3.2 Methods (3.2a) Cleaning of substrates.

Microscope slides made from premium float glass (Fishers' Finest) were used in these experiments. These slides were cleaned in piranha solution (70% $H_2SO_4$, 30% $H_2O_2$) and then in a base solution (70% KOH, 30% $H_2O_2$) under nitrogen agitation for 1 hour at 50° C. Between solutions and after the base wash, the slides were rinsed thoroughly in deionized water at 18.2 M Ω (Millipore). The slides were subsequently rinsed in ethanol followed by methanol. This step caused the slides to dry without residual spots. The slides were then dried in nitrogen and stored in a vacuum oven at 110° C. Storage in the oven minimized water adsorption onto the glass slides. All other glassware was cleaned in piranha solution prior to use.

(3.2b) Deposition of gold.

Semi-transparent films of gold (approximately 100 Å in thickness) were evaporated by electron beam (CH A Industries) onto stationary microscope slides from a fixed direction with 50° incidence from the surface normal. A 20 Å layer of titanium was used to promote adhesion between the glass and the gold. The rate of gold and titanium deposition was carefully controlled to 0.2 Å/sec within a system pressure less than 1×10$^{-6}$ Torr. In order to maintain high quality films the gold source was routinely cleaned in 3–4 cycles of aqua regia and piranha solutions at 50° C. for 30 minutes in each solution. This cycle was repeated 3–4 times with rinses in deionized water between each solution.

(3.2c) Formation of SAMs.

SAMs were formed in 1 mM HS(CH$_2$)$_{10}$COOH in ethanol for 1 hour. The SAMs were then immersed for approximately one minute in aqueous, pH solutions buffered between pH 2–12 and then blown dry with a stream of nitrogen gas to displace excess solution from the surface. Unless stated differently, the buffers were formed using the following salts: pH 1–2, 0.1 M H$_3$PO$_4$; pH 2.5–3.0, 1 mM NaH$_2$PO$_4$/H$_3$PO$_4$; pH 4–5, 1 mM NaO$_2$CCH$_3$/HO$_2$CCH$_3$; pH 6–7, 1 mM Na$_2$HPO$_4$/NaH2PO4; pH 8–9, 1 mM Na$_2$CO$_3$/NaHCO$_3$; pH 9–11, 1 mM Na$_2$HPO$_4$/Na$_3$PO$_4$; pH 11.5–12, 10 mM NaOH; pH 12–13, 0.1 M NaOH. The same counterion, Na+, was used throughout. Experiments were also performed using 0.01 mM–1 mM HCl.

(3.2d) Anchoring of LCs.

he anchoring of liquid crystals was studied by constructing optical cells from SAMs formed from HS(CH$_2$)$_{10}$COOH on each surface at same pH or from one surface formed from HS(CH$_2$)$_{10}$COOH and the opposing surface formed from CH$_3$(CH$_2$)$_{15}$SH. The evaporation direction between the opposing gold surfaces in the cell was oriented in the same direction. The surfaces were separated by mylar spacers with nominal thickness of 2, 12, and 30 μm and clamped together using binder clips. By interferometry techniques, 15–20% variation was observed for nominal cell thicknesses of 12, 30 μm. The thinner, 2 μm nominal thickness had greater variation, ranging from 2–4 μm. The cells were filled with liquid crystal by capillarity at a temperature above the clearing point in the isotropic state. The resultant optical texture was analyzed with a polarizing microscope (Olympus) after the cells were cooled to room temperature.

Surfaces presenting carboxylic acid groups and sodium carboxylate groups were prepared by immersion of the SAMs in aqueous solutions at low and high pH. The orientations of liquid crystals within cells (thickness 2–4 μm) was measured using SAMs pretreated at high and low pH.

3.3 Results

First, the out-of-plane orientation of the liquid crystals on SAMs pretreated at low and high pH was measured. Near planar orientation was observed using the crystal rotation technique. The polar angle from the surface was less than 1°, for 5CB.

Second, the in-plane (azimuthal) orientation of the liquid crystal was measured by using polarized light microscopy. The in-plane orientation of liquid crystal with respect to the gold evaporation direction was determined by using a quarter wave plate (QWP) and a thin 2 μm cell prepared with SAMs (at low or high pH) filled with liquid crystal. Using a QWP, the orientation of the director was determined by rotating the cell until the greatest the shift in retardation between the slow axis of the nematic director and the optical axis of the QWP was observed. The shift in retardation was measured on a Michel-Levy color chart from the first and second order interference colors. Whereas no changes were observed in the out-of-plane orientation of the liquid crystals as a function of the pH of pretreatment, the in-plane orientations of nematic 5CB and MBBA were observed to be different when both surfaces were pretreated at low and high pH. Under these pretreatments, a uniform texture of liquid crystal was observed throughout the cell. The in-plane orientation of the 5CB and MBBA, however, was observed to shift 90° based on the pH pretreatment of the surface at pH 2.5 (low pH) and 11.7 (high pH).

In cells filled with 5CB or MBBA, using surfaces immersed at pH 2.5, the liquid crystal oriented parallel to the direction of gold deposition as illustrated in FIG. 9a. However on monolayers conditioned at pH 11.7, the liquid crystals oriented perpendicular to the direction of gold deposition as shown in FIG. 9b. In both cases, there were no elastic deformation (twist, bend, or splay) in the bulk liquid crystal. These SAMs also exhibited reversible properties for orienting 5CB. Pretreatment of the SAM at pH 3.0 and subsequently at pH 11.7 resulted in 5CB orientation perpendicular to the deposition direction. The opposite pretreatment scheme results in parallel alignment.

Although the liquid crystals are known to contain significant amounts of water that could potentially erase the effect of the pretreatment of the surfaces (and thus the influence of the pretreatment of the surfaces on the orientations of the liquid crystals), the results described above demonstrate that this is not the case. The effect of the pretreatment of the liquid crystal changes the orientation of the liquid crystal. The concentration of water in our samples of 5CB was 42±7 mM as measured by Karl Fischer titration.

As described below, this effect can be further evidenced by the lateral patterning of a surface with COOH and COO$^-$Na$^+$ regions and observing the orientation of the liquid crystal in the vicinity of the boundary between the low and high pH regions. FIG. 10c shows the optical texture of a liquid crystal cell prepared by forming a SAM of HS(CH$_2$)$_{15}$CH$_3$ on one surface while the opposing surface was formed from HS(CH$_2$)$_{10}$COOH. The entire surface of HS(CH$_2$)$_{10}$COOH was pretreated at pH 3.0 and dried in nitrogen. This surface was then reversibly treated by half-dipping at pH 11.7 and carefully drying the surface in nitrogen. The anchoring of the liquid crystal was observed to be orthogonal on the adjacent regions of the acid surface pretreated at differing pHs. If ion exchange between the surfaces and the bulk liquid crystal was occurring, then time-dependent changes in the vicinity of this boundary would be observed. No change in the anchoring of the liquid crystal in the vicinity of the boundary over a period of 48 hours was observed.

In cells designed with SAMs of HS(CH$_2$)$_{15}$CH$_3$ on one surface and HS(CH$_2$)$_{10}$COOH on the opposing surface, pH pretreatment of HS(CH$_2$)$_{10}$COOH, can be used to induce a bulk elastic deformation of the liquid crystal. As illustrated in FIG. 10a, at low pH, 5CB was uniformly oriented since the same in-plane liquid crystal orientation was imposed by both surfaces. At high pH, the monolayer of HS(CH$_2$)$_{10}$COOH imposed an in-plane boundary condition orthogonal to the HS(CH$_2$)$_{15}$CH$_3$ surface resulting in a twisted bulk orientation for the liquid crystal. This result demonstrated that the strength of anchoring on both surfaces was sufficient to create a deformation in the bulk which rotated the polarization of light by 90°.

In this cell, of nominal thickness 12 μm, 5CB was sandwiched between SAMs formed from HS(CH$_2$)$_{15}$CH$_3$ and HS(CH$_2$)$_{10}$COOH at pH 3.0 (region I) or pH 11.7 (region II). When viewed through cross polars (FIG. 10c), region I which was composed of surfaces anchoring the nematic director in the same direction appears dark due to the extinction of transmitted light. The bulk orientation of the liquid crystal was uniform and along a single direction. In region II light was uniformly transmitted through cross polars suggesting the bulk orientation of the liquid crystal was twisted.

Observation under parallel polars (90° rotation of the analyzer) as shown in FIG. 10d indicated that region I turned bright while region II turned dark. This result indicates an approximate 90° twist in region II but not region I. The bulk orientation of 5CB can be controlled between uniform and twisted orientations in cells with surfaces supporting SAMs formed from $HS(CH_2)_{15}CH_3$ and SAMs formed from $HS(CH_2)_{10}COOH$ (at high or low pH).

How the liquid crystal bulk orientation changes in 12 μm cells with surfaces formed from $HS(CH_2)_{15}CH_3$ and $HS(CH_2)_{10}COOH$ as a function of pH between 1.7 and 13.2 was also investigated. The transition between a uniformly aligned cell to a twisted cell for SAMs formed from $HS(CH_2)_{10}COOH$ occurred, discontinuously between pH 3.8–4.0. The transition is visually illustrated in FIG. 11a at each pH through cross polars. Intermediate twist angles were not observed, however, at pH 3.8, twisted regions with dimensions of 100–1000 μm were observed within the uniformly oriented sample. The change in orientation from uniform to twisted alignment occurred through the proliferation of 90° twisted domains of liquid crystal.

Figure 11K:
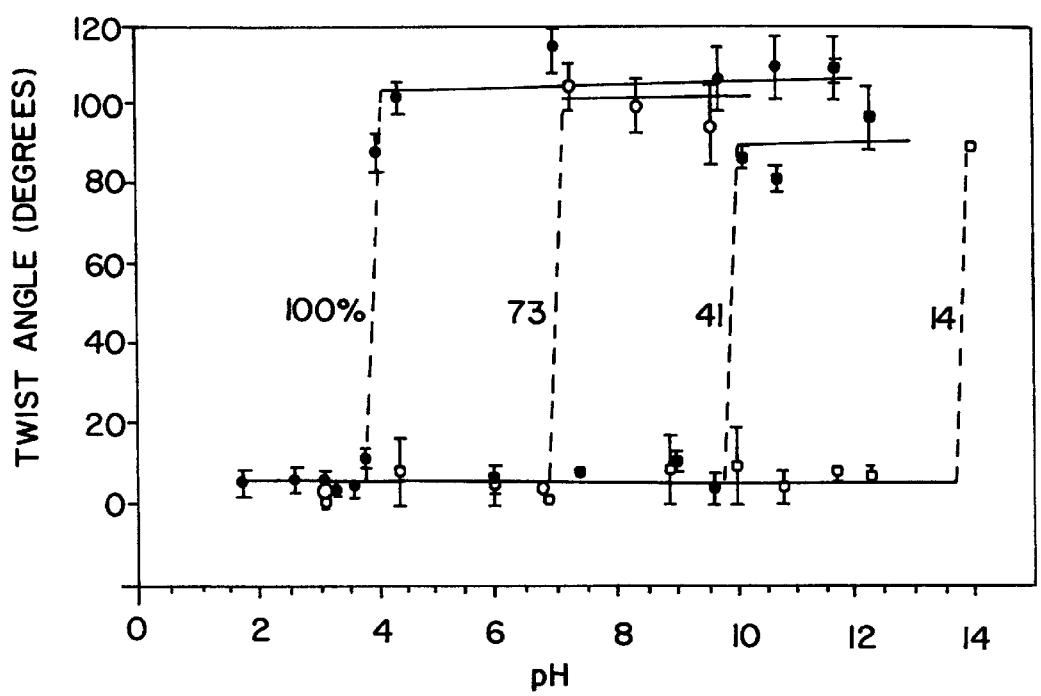
FIG. 11A displays textures of 5CB observed between cross polars in optical cells formed from SAMs of $HS(CH_2)_{15}CH_3$ on one surface and $HS(CH_2)_{10}COOH$ pretreated between pH 2–13 on the opposing surface. The deposition direction of gold is oriented parallel to the polarizer.
FIG. 11B is the measured twist angle as a function of the monolayer composition of $HS(CH_2)_{10}COOH$ and the surface pH pretreatment. The plot illustrates the ability to control the pH of the transition from uniform to twisted orientation.

The rotation of the polarization through the cell filled with 5CB provided a simple, quantitative method of observing the discontinuous change in; 5CB alignment. The twist angle was determined by simultaneously rotating the analyzer and the optical cell with respect to the polarizer to a minimum intensity. The twist angle as a function of pH is illustrated in FIG. 11b. A sharp discontinuity between pH 3.8 and pH 4.0 indicated a sharp, discontinuous, 90° in-plane reorientation of 5CB.

Loop disclinations formed in twisted areas as shown in region II in FIG. 10c, 10d and FIG. 11a at pH 11.7, 12.7. The twist angle within these loops were, in general, the supplementary angle to the measured twist angle of the overall phase. The disclination line appeared dark between cross polars and bright between parallel polars indicating a disclination line of strength S=½.

Twist angles for cells pretreated at pH>3.8 were approximately 95–105°. A 5–10° error occurred from the glass slides being slightly twisted on the sample holders during the evaporation process. Therefore the gold was not deposited exactly along the perpendicular axis of the glass slide. Minor errors also occurred (<5°) when aligning the two opposing surfaces against each other during cell construction.

Example 3 demonstrates that liquid crystals can be used to transduce into optical signals the transformation of a carboxylic acid group on a surface into a carboxylate salt. Small changes in structure of surfaces are known to influence the bulk orientation of liquid crystals. A discontinuous, 90° in-plane reorientation of 5CB is observed depending upon the number of methylene groups composing an alkanethiol monolayer. An odd number of methylene units resulted in anchoring parallel to the deposition direction of the gold while an even number resulted in anchoring perpendicular to the deposition direction. The differences in orientation are attributed to the different orientations of the terminal methyl group within SAMs formed from even and odd numbered alkanethiols.

The acidity of the SAMs can be decreased using mixtures of $HS(CH_2)_{10}COOH$ and $HS(CH_2)nCH_3$. Using this technique, the pH transition from uniform to twisted orientation was controlled by forming SAMs from a mixture of 1 mM 4:1, 2:1, 1:2 $HS(CH_2)_{10}COOH$ and $HS(CH_2)_{12}CH_3$. The pH dependent transition was shifted to pH 7, pH 10, and pH 14, respectively. FIG. 11b illustrates the discontinous transition as measured through the twist angle that was observed for all the monolayers that were tested.

Figure 12:
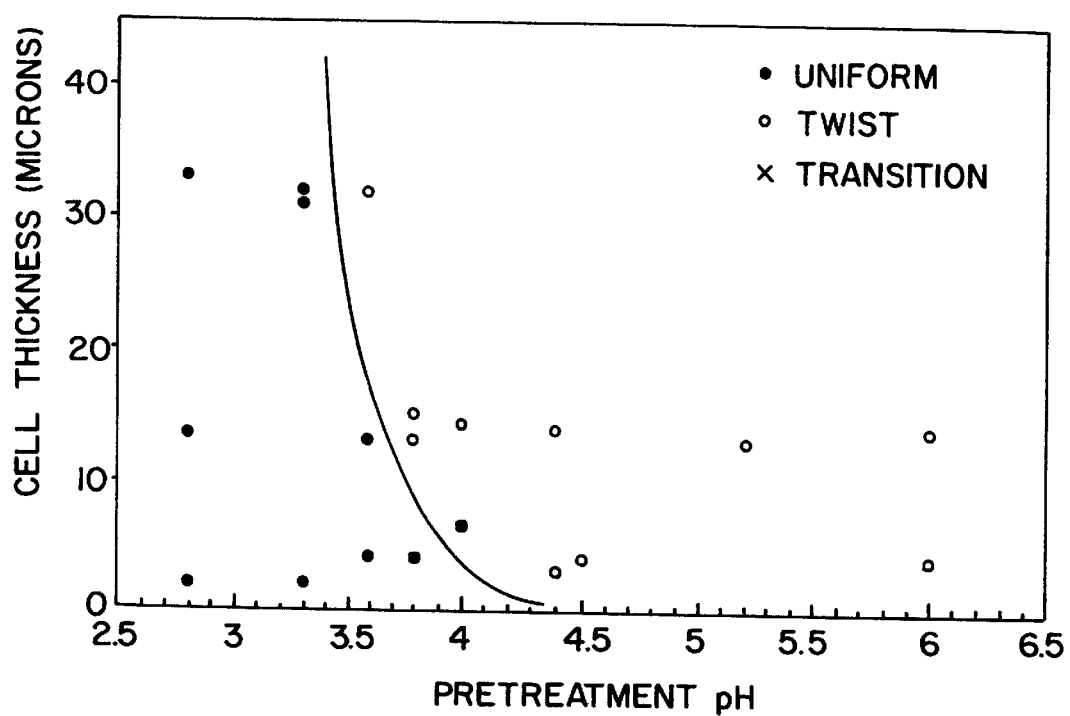
FIG. 12 illustrates a pH of anchoring transition between uniform and twisted 5CB orientation as a function of cell thickness. Black points represent uniform alignment, open points represent twisted orientation, and the X represents numerous patches of twist regions. The solid line indicates the discontinuous boundary between the uniform and twisted regions.

The pH transition from uniform to twisted alignment was shifted by 0.4 pH units through control of the cell thickness. Since the distortion energy due to the twist distortion varies as the inverse of cell thickness, higher anchoring energies (which manifest in higher pH pretreatments) were required to induce a twist distortion in thinner cells. FIG. 12 illustrates this dependence for three nominal cell thicknesses, 2 μm, 12 μm, and 30 μm over a pH range spanning uniform to twisted orientation. In the 2 μm cells, domains of twist as well as a complete twist in the bulk were observed over pH 3.8–4.0.

In cells prepared with $HS(CH_2)_{10}COOH$ on each surface, the orientation of 5CB went through the discontinuous, in-plane transition between pH 3.8 and 4.0. Since bulk distortions are not induced by these surfaces, we assumed this transition range is representative of the onset of ionization of the surface.

Figure 13:
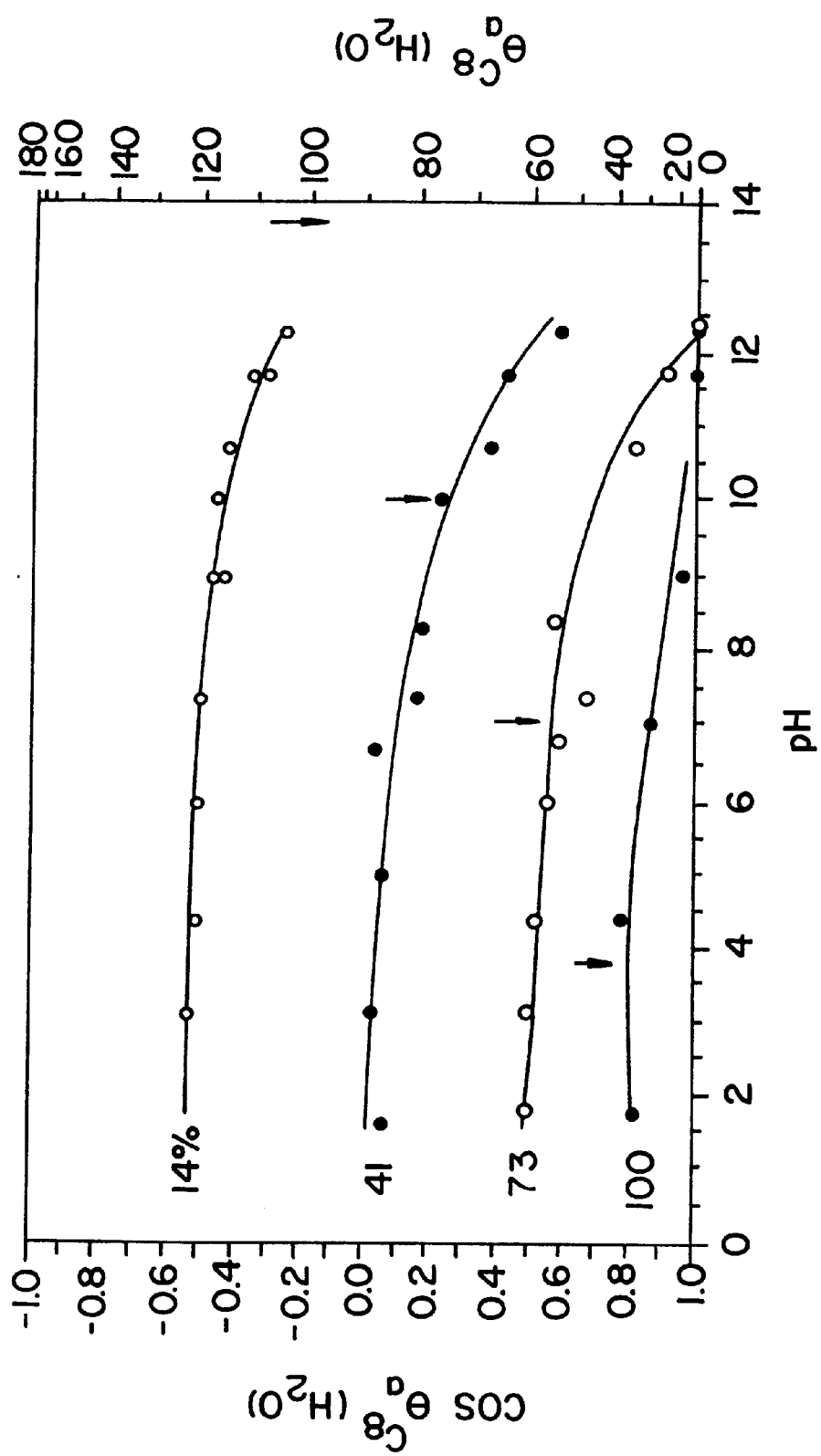
FIG. 13 displays advancing contact angles of buffered, aqueous solutions measured under cyclooctane on mixed monolayers of $HS(CH_2)_{11}CH_3$ and $HS(CH_2)_{10}COOH$, plotted as a function of pH. The curves are labelled by the proportion of chains in the monolayer that terminated by the COOH group. The solid arrows indicate the pH where a transition from uniform to twisted 5CB orientation was observed.

FIG. 13 plots $\Theta aC_8(H_2O)$ as a function of pH for monolayer prepared from mixtures $HS(CH_2)_{10}COOH$ and $HS(CH_2)_{12}CH_3$. The percentage of chains terminated with COOH is labelled for each titration curve. The bolded arrows indicate the pH range where 5CB orientations in optical cells reoriented from uniform to twisted alignment. A number of features are present in these curves. First, as observed by Bain, the contact angles at low pH were constant and decreased at higher pH. See, Bain, C. D.; Whitesides, G. M., *Langmuir*, 5:1370–1378 (1989)). Similarly, the breakpoint in the titration curves occurred at higher pH as the proportion of methyl terminated chains in the monolayer was increased. However, the pH transition for 5CB orientation increased with respect to the breakpoint pH (observed by contact angles) as the proportion of $HS(CH_2)_{10}COOH$ decreased on the surface. In fact, on a SAM formed from only $HS(CH_2)_{10}COOH$, the pH of the twist transition (pH 3.8–4.0) was observed to be less than the pH of the breakpoint (pH 5.0–5.5).

These results indicate a critical density of carboxylic acid terminal groups is required for the transition in 5CB from uniform to twisted. A linear relation is observed up to surface compositions of monolayers terminated with 41% carboxylic acid (2:1 $HS(CH_2)_{10}COOH$ and $HS(CH_2)_{12}CH$).

EXAMPLE 4

Example 4 illustrates the quantitative detection of metal ions by their binding to SAMs with carboxylic acid terminal groups. Similar to the examples above, the binding of the metal ion is amplified and transduced into an optical signal by a liquid crystal layer. We use the binding of copper ions from aqueous solutions as an example.

First, microscope slides were covered with semi-transparent layer of titanium (30 Angstroms in thickness) and then gold (140 Angstroms). These metals were deposited with an oblique angle of incidence (50 degrees from normal of slide) using an electron beam evaporator. The metal-coated microscope slides were then immersed into a 1 mM solution of 1 1-mercaptoundecanoic acid (HOOC $(CH_2)_{10}SH$) in ethanol for 1 hour. This procedure lead to the formation of SAMs that presented HOOC-groups at their outer surfaces.

Second, aqueous solutions of $Cu^{2+}$ were prepared from $Cu(ClO_4)_2$ with concentrations ranging between 1 mM–20 mM. The gold films supporting SAMs were then immersed for 5 minutes into these solutions of $Cu^{2+}$ below pH 5.5. After removal from the aqueous solution, the surfaces were vigorously dried under nitrogen and then absolute ethanol in order to remove any nonspecifically attached $Cu^{2+}$.

Third, surfaces treated as described above were assembled into optical cells with a thickness (cavity thickness) of 12 micrometers. The cells were filled with 4-cyano-4 pentylbiphenyl (5CB) by capillarity at a temperature above the clearing temperature of 5CB. The resultant optical texture was analyzed with a polarizing microscope (Olympus) after the cells were cooled to room temperature.

Figure 14A:
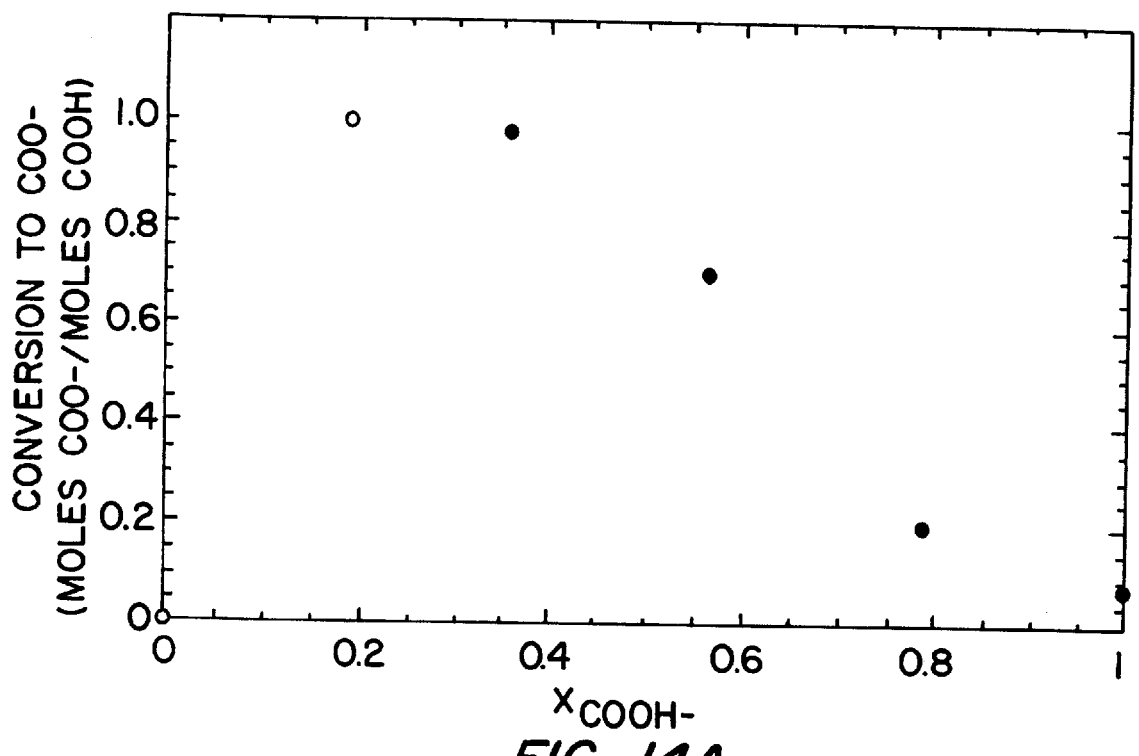
FIG. 14A The abscissa of 14A is the mole fraction of $COOH/COO^- Na^+$ within a mixed SAM formed from $HS(CH_2)_{11}CH_3$ and $HS(CH_2)_{10}COOH$. The ordinate is the extent of conversion of $COOH$ to $COO^- Na^+$. By varying the composition of the mixed SAM, the extent of conversion has been systematically moved between 8% and 100%.
Figure 14B:
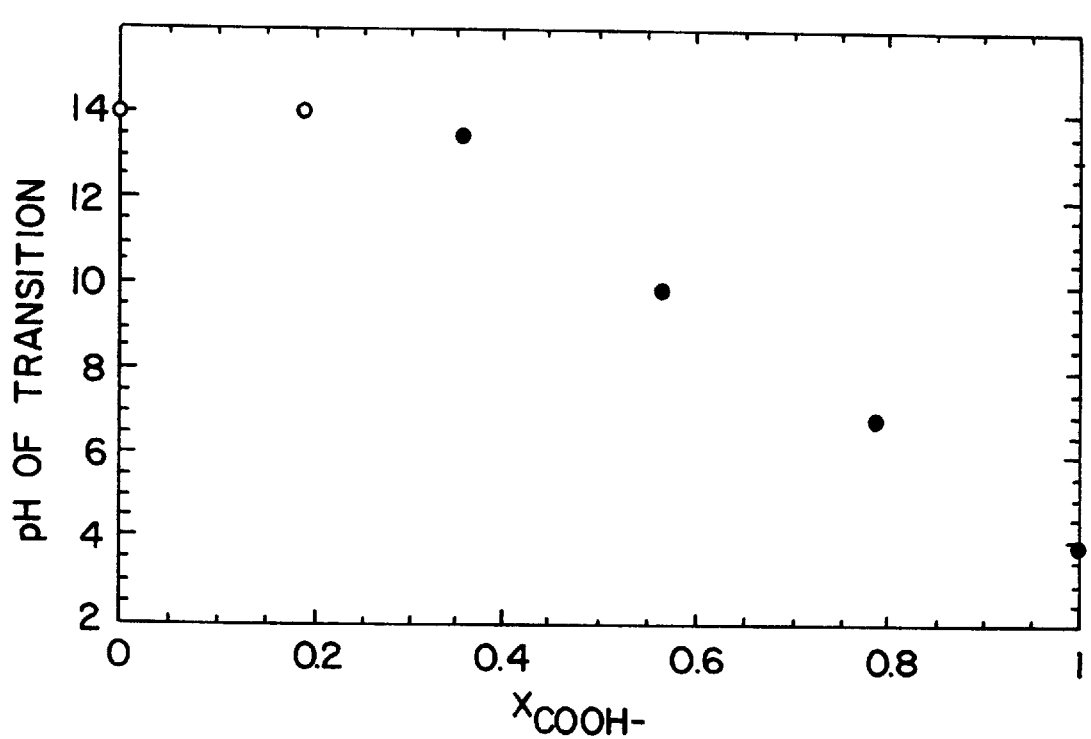
FIG. 14B shows the corresponding bulk pH of the solution used to transform the acid to its salt.

When the concentration of $Cu^{2+}$ in solution was 0.01 mM or less, the alignment of the LC was uniform and planar (FIG. 14A). When the concentration of $Cu^{2+}$ in solution was 0.1 mM and 1 mM, the alignment of the LC was non-uniform and planar (FIG. 14B and 14C). When the concentration of $Cu^{2+}$ in solution was 18 mM, the alignment of the LC was homeotropic (FIG. 14D).

Further evidence of the $Cu^{2+}$ binding to the carboxylic acid functionalized surface was observed in patterned optical cells. In these devices, the two opposing surfaces were half-dipped into 1 mM $Cu(ClO_4)_2$. The other side of the surface were left unpretreated. The resultant patterned cell clearly illustrated the difference between regions exposed to $Cu^{2+}$ (which are nonuniform.) (FIG. 14E).

EXAMPLE 5

Example 5 illustrates the control of the alignment of liquid crystals using patterned SAMs.

The patterning of mesogenic layers on surfaces is illustrated by fabrication of three linear diffraction gratings (FIG. 15). These gratings differ in the manner of distortion of the mesogenic layers and thus their optical properties. Patterned SAMs were prepared by microcontact printing with an elastomeric stamp (Kumar et al., *Acc. Chem. Res.* 28, 219 (1995), and references therein). The stamp was inked with an ethanolic solution of $CH_3(CH_2)_{15}SH$ and put in contact with ultrathin (100 Å thick), semi-transparent films of polycrystalline gold. SAMs were then formed on the unreacted areas of gold by immersion the gold films in ethanolic solutions containing 1 mM of a second alkanethiol for 2 hours. Two surfaces supporting SAMs were subsequently paired and spaced apart with Mylar film. The space between the surfaces was filled with the nematic mesogen 4-cyano-4'-pentylbiphenyl (5CB) by capillarity. A polarizing microscope with white light was used to image the patterned liquid crystals. Descriptions of experimental procedures have been reported elsewhere (Drawhorn et al., *J. Phys. Chem.* 99, 16511 (1995); Gupta et al., *Langmuir* 12, 2587 (1996)).

Fabrication of the periodic liquid crystal structure shown in FIG. 15A (grating A) requires uniform planar anchoring of the liquid crystal on the top surface of the cell and patterned planar anchoring of the mesogen with orthogonal azimuthal orientations in adjacent stripes on the bottom surface. Planar anchoring of nematic liquid crystals can be achieved by using single-component SAMs formed from $CH_3(CH_2)_{n-1}SH$ (n=4 to 17) on gold. (The observation of planar anchoring of mesogens on surfaces with energies as low as alkanethiols on gold (19 mN/m) is unusual. For example, monolayers formed from octadecyltrichlorosilane on silica have surface energies as low as alkanethiols on gold (19 mN/m) yet cause homeotropic anchoring of mesogens. The anisotropic part of the dispersion force acting between 5CB and gold influences anchoring of 5CB on SAMs formed from $CH_3(CH_2)_{n-1}SH$ (Miller et al., *Appl. Phys. Lett.* 69, 1852 (1996)).

The anchoring is azimuthally uniform on SAMs supported on films of gold deposited with a 50° angle of incidence (Gupta et al., *Langmuir* 12, 2587 (1996)). Oblique deposition of silicon oxide ($SiO_x$) and metals can be used to align mesogens at surfaces (Urbach et al., ibid. 25, 479 (1974); J. L. Janning, ibid 21, 173 (1972)). This method, however, is not economically competitive with methods based on rubbed polymers when uniform alignment of a mesogen over a large area is required. In contrast, when patterned orientations of mesogens are required, processes based on rubbing become complex, and oblique deposition of metals can form the basis of simple and economical procedures.

The anchoring of 5CB is perpendicular to the direction of deposition of the gold on SAMs formed from odd alkanethiols (for example, n=11; FIG. 15A) and parallel to the direction of deposition of gold on SAMs formed from even alkanethiols (for example, n=12; FIG. 15B) (Gupta et al., *Phys. Rev. E* 54, 4540 (1996)); the alignment of 5CB on "bare," obliquely deposited gold is planar and perpendicular to the direction of deposition of the gold). Differences in the orientation of the methyl groups at the surface of SAMs formed from odd and even alkanethiols on gold direct the in-plane orientation of the nematic mesogen (Gupta et al., *Phys. Rev. E* 54, 4540 (1996)); the orientation of methyl groups exposed at the surface of SAMs formed from $CH_3(CH_2)_{n-1}SH$ on gold differ for odd and even alkanethiols because the aliphatic chains within these SAMs are tilted away from the surface normal by 30° (Nuzzo et al., *J. Am. Chem. Soc.* 112, 558 (1990)). In contrast, chains within SAMs formed from alkanethiols on silver and perfluorinated alkanethiols on gold are tilted by less than 10° to 15°, and there is no odd-even variation in the orientation of the methyl groups ($CH_3$ or $CF_3$) at the surface of these SAMs (Laibinis et al., ibid., 113, 7152 (1991)); (Lenk et at., *Langmuir* 10, 4610 (1994)). No odd-even dependence was observed for the orientation of 5CB on SAMs formed from alkanethiols on silver or perfluorinated alkanethiols on gold: the anchoring of 5CB was perpendicular to the direction of deposition of the gold; a 90 azimuthal reorientation of a mesogen on a corrugated surface can be caused by a coupling of elastic and flexolectric effects.

Figure 17C:
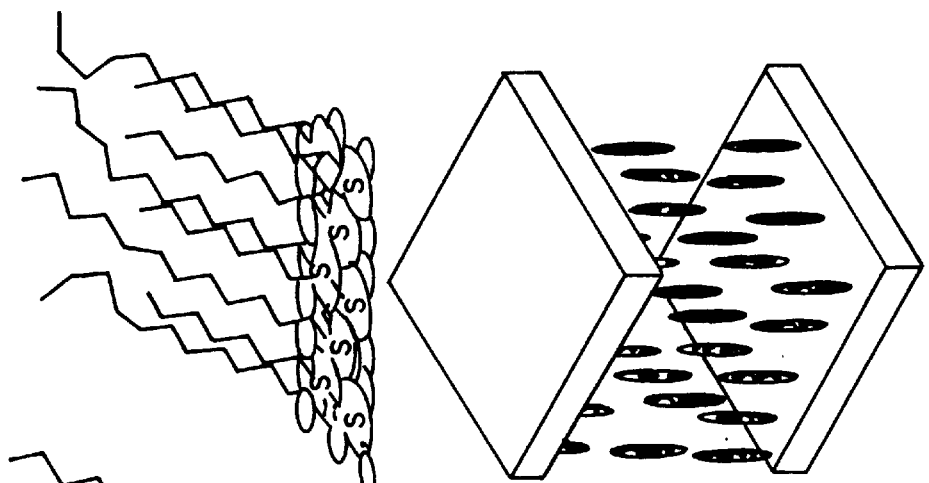
FIG. 17 (A to C) displays the range of anchoring modes of a mesogenic layer on organic layers having different compostions.
Figure 17B:
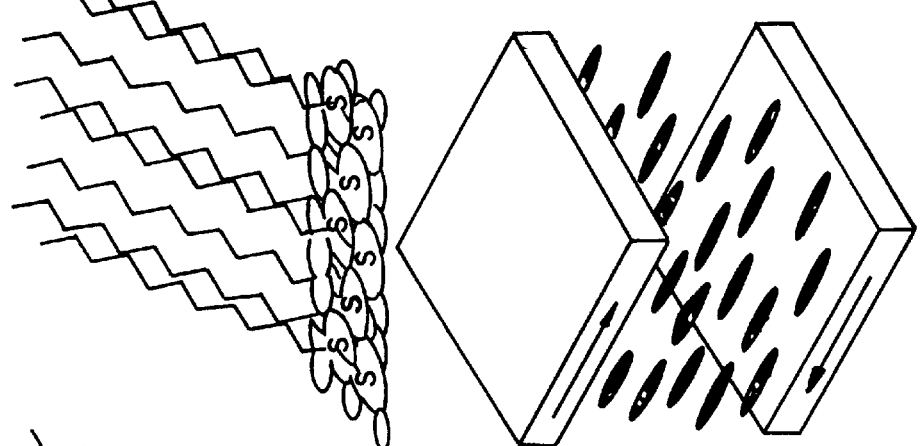
Figure 17A:
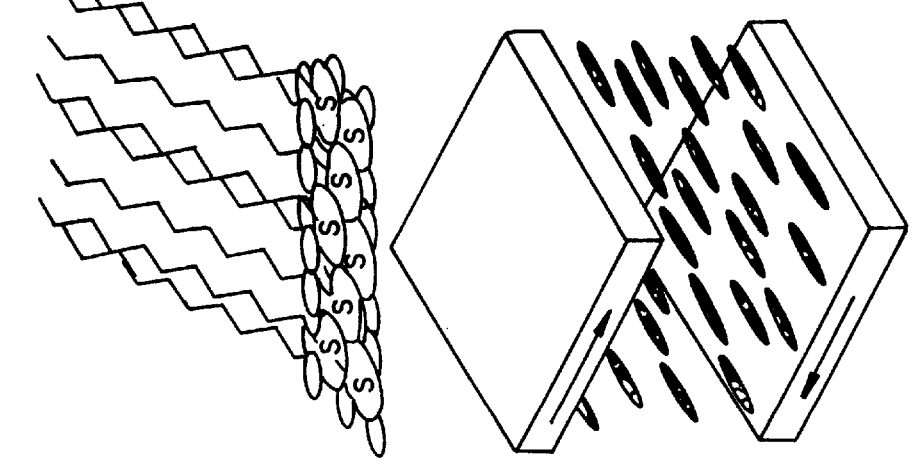

Patterned SAMs formed from $CH_3(CH_2)_{14}SH$ and $CH_3(CH_2)_{15}SH$ on obliquely deposited gold were used to fabricate grating A. The polarization of linearly polarized light is not changed by transmission (along the z direction in FIG. 17A) through the regions of the mesogenic layer with uniform planar anchoring but is rotated by 90° upon transmission through regions of the mesogenic layer that are twisted by 90° (Yeh, P., OPTICAL WAVES IN LAYERED MEDIA (Wiley, N.Y., 1988)). When viewed through crossed polars, therefore, twisted regions of grating A appear bright (light is transmitted by the analyzer) and uniform regions appear dark (light is extinguished by the analyzer) (FIG. 17A). The periodic change in refractive index across the grating causes diffraction of laser light (FIG. 17B).

The grating in FIG. 15B (grating B) is based on homeotropic anchoring of the mesogenic layer on the top surface of the cell and patterned planar and homeotropic anchoring of the mesogenic on the bottom surface. Light incident on grating B with a linear polarization along the x direction will experience a periodic change in refractive index and will be diffracted. In contrast, light with polarization along they direction will experience no spatial variations in refractive index and will not be diffracted. Mixed SAMs formed by coadsorption of long and short alkanethiols on gold to homeotropically anchor 5CB (FIG. 16C) (Drawhorn et al.,*J. Phys. Chem.* 99, 16511 (1995)) Gupta et al., *Langmuir* 12, 2587 (1996); Yeh, P., OPTICAL WAVES IN LAYERED MEDIA (Wiley, N.Y., 1988)).

The planar to homeotropic transition in anchoring of 5CB observed on mixed SAMs formed from long and short alkanethiol on gold differs from past reports in which Langmuir-Blodgett films of lecithin were used: the anchoring of 5CB is homeotropic for all packing densities of lecithin (Hiltrop et al., *Ber. Bunsen-Ges. Phys. Chem.* 98, 209 (1994)) in a grating of type B. A polarized light micrograph of the mesogenic grating viewed through crossed polars is shown in FIG. 17C. Dark stripes correspond to regions of the grating in which the polarization of linearly polarized light was not changed by transmission through the mesogen; these stripes remained dark when the sample was rotated between the crossed polars, thus confirming homeotropic anchoring in these regions. Bright stripes correspond to regions of the mesogenic layer distorted by planar anchoring of the layer on the bottom surface and homeotropic anchoring of the layer on the top surface of the cell. Patterned homeotropic and planar anchoring of mesogens has not been demonstrated in past work that was based on photo-alignment or rubbing techniques.

In contrast to grating B, the diffraction of light by the grating in FIG. 15C (grating C) was polarization insensitive. When grating C was viewed under crossed polars, either uniformly bright stripes (FIG. 17D, polarization of incident light between x and y) or uniformly dark stripes (polarization of incident light along x or y) was observed. The boundaries between stripes, which correspond to regions in which two different distortions of the mesogens meet, were visible in the optical micrographs (dark lines in FIG. 17D). The lack of measurable contrast between adjacent stripes for all polarizations of incident light is consistent with the mesogenic layer structure of grating C. A similar type of layer structure has been reported by Chen and co-workers who use a two-step rubbing process (Chen et al., *Appl. Phys. Lett.* 67,2588 (1995)).

The polarization sensitivity of gratings B and C was further tested by viewing these gratings with linearly polarized light (not crossed polars). When grating B was viewed with light having a linear polarization along the x direction, the grating pattern was visible (FIG. 18A) because the incident light experienced a spatially periodic refractive index. With light polarized along they direction, however, only faint edges of the stripes were Seen (FIG. 18B); these edges did not cause measurable diffraction of light. In contrast, because grating C is insensitive to the polarization of incident light, the grating was visible upon illumination by light with polarization along x or y (FIG. 18C and 18D).

Tuning of these patterned mesogen structures was possible by using electric fields. When gold surfaces supporting SAMs were used as electrodes, an electric field could be applied perpendicular to the surfaces. Reversible application of the electric field reorients the mesogens and thus modulated the intensity of light diffracted from the gratings (FIG. 18E). In-plane electric fields were also used (in-plane switching refers to the use of an electric field that is applied parallel to the surface of the cell). Devices based on in-plane switching of a mesogen have been used in FPDs with wide viewing angles (Ohe et al., *Appl. Phys. Lett.* 69, 623 (1996); Ohta et al., *IEICE (Inst. Electron Inf. Commun. Eng.) Trans. Electron.* E79-C, 1069 (1996)) to reorient these patterned mesogenic structures. We observe SAMs to be stable upon application of an electric field across a cell filled with mesogen. Past studies have reported electrochemical desorption of SAMs in aqueous solutions of electrolytes (Widrig et al., *J. Electroanal. Chem.* 310, 335 (1991); Waliquid crystalzak et al., *Langmuir* 7, 2687 (1991)). In general, the alignment of mesogens on SAMs formed from long-chain alkanethiols is stable over months. Stability over years can be achieved by using polymerizable SAMs (T. Kim et al., *Langmuir* 12, 6065 (1996)) or mesogens doped with alkanethiols or reducing agents to prevent oxidative degradation of the SAMS.

Figure 19A:
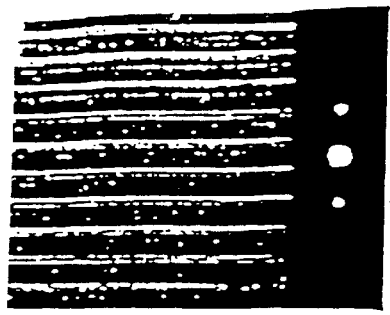
Figure 19C:
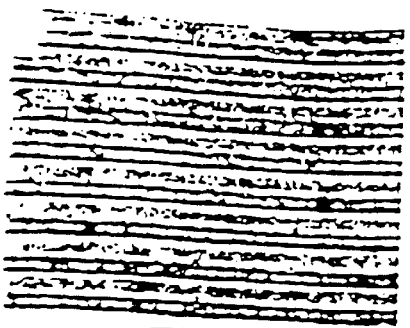
Figure 19B:
Figure 19D:
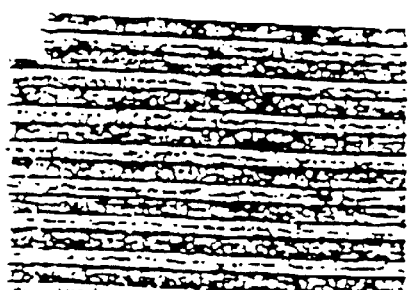
Figure 20A:
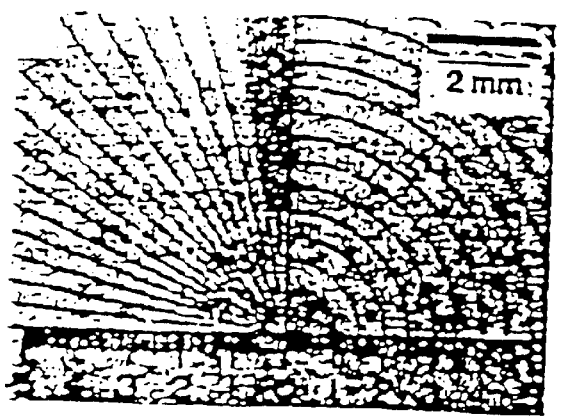
FIG. 20 displays the complex LC structure formed with patterned SAMs.
Figure 20B:
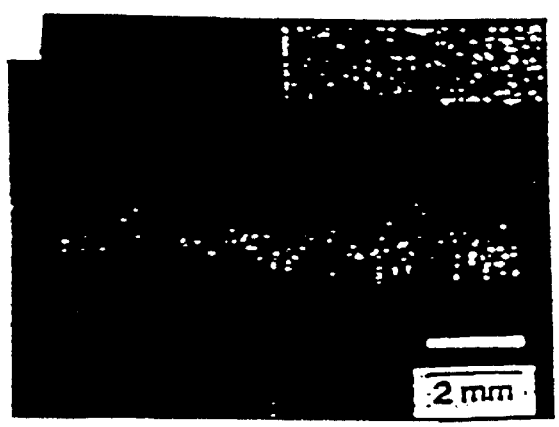
Figure 21A:
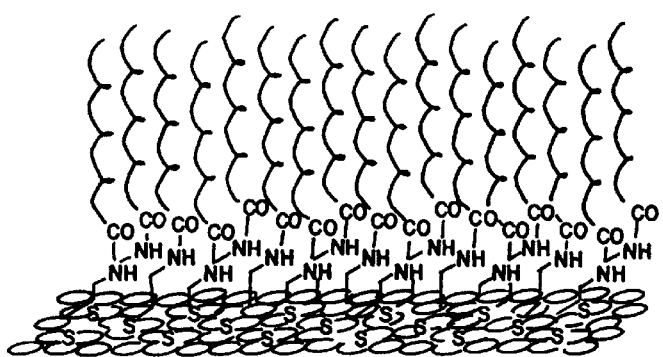
FIG. 21 displays cartoons of SAMS formed from (a) 1: $CF_3(CF_2)_7CONH(CH_2)_2SH$; (b) 2: $CF_3(CF_2)_7(CH_2)_2SH$; (c) 3: $CF_3(CF_2)_7(CH_2)_{11}SH$; (d) 5: $CH_3(CH_2)_{11}SH$. The semifluorinated chains form a helical conformation within the SAM; the axis of the helix is almost normal to the surface for SAMs formed from 3.
Figure 21B:
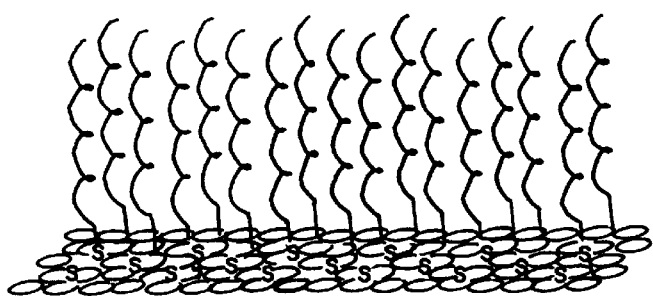
Figure 21C:
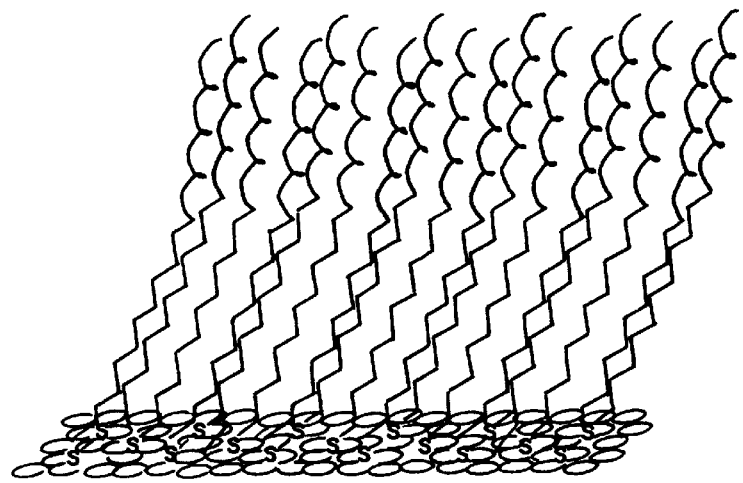
Figure 21D:
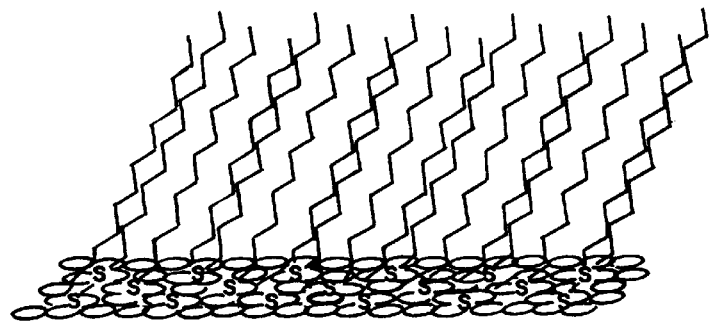

The methods reported here permit fabrication of complex mesogen structures in two simple processing steps. Surfaces can be patterned with regions of mesogens that differ in shape and have sizes ranging from micrometers to centimeters (FIG. 19A). The mesogens can also be patterned on nonplanar surfaces (FIG. 19B).

EXAMPLE 6

6.1 Materials and Methods

Hexadecane was purchased from Aldrich and passed through a column of alumina before use. The semifluorinated thiols $CF_3(CF_2)_7CONH(CH_2)_2SH$ (1), $CF_3(CF_2)_7(CH_2)_2SH$ (2) and $CF_3(CF_2)_7(CH_2)_{11}SH$ (3) were available from previous studies. See, Drawhorn, R. A. et al, 1995, *J. Phys. Chem.*, 99, 16511; Solution compositions of 1:1 and 3:1 were needed to form surface compositions of 1:1 for mixed SAMs formed from 1 and 2 and 1 and 3, respectively. Decanethiol (4), dodecanethiol (5) and hexadecanethiol (6) were purchased from Aldrich, and 4-n-pentyl4'-n-cyanobiphenyl (5CB, $T_{NI}=35°$ C., $T_{KN}=24°$ C.) was purchased from EM Sciences. Anhydrous ethanol was purchased from Quantum.

6.1a Sample preparation

Glass microscope slides were cleaned in "piranha" solution (70:30 concentrated $H_2SO_4/30\%$ $H_2O_2$, WARNING: piranha solution reacts strongly with organic compounds and should be handled with extreme caution; do not store the solution in closed containers) for 30 minutes at 90° C. Substrates of gold were prepared by evaporation (100 Å at 0.2 Å/s, $P<5\times10^{-6}$ torr, with epicyclic rotation of sample relative to the incident flux of Au) onto microscope slides. See, Gupta, V. K, et al., 1996, *Chemistry of Materials*, 8, 1366. Approximately 10 Å of titanium was used to promote adhesion between the gold and glass microscope slides. Self-assembled monolayers were formed for 2 hours in ethanolic solutions that contained a 1 mM total concentration of thiol. Binary mixed SAMs were formed by coadsorption of the thiols such that the compositions of SAMs were 1:1 for SAMs formed from 1 and 2 and from 1 and 3. The compositions of the SAMs were estimated by XPS [Solution compositions of 1:1 and 3:1 were needed to form surface compositions of 1:1 for mixed SAMs formed from 1 and 2 and 1 and 3, respectively.; Laibinis, P. E., et al., 1992, *J. Phys. Chem.*, 96, 5097. The compositions of mixed SAMs formed under these conditions were determined by the kinetics of chemisorption.

6.1b Contact Angles

Advancing and receding contact angles of hexadecane were measured using a Rame-Hart goniometer and environmental chamber. A drop of hexadecane was placed in contact with the surface using the needle of a syringe. By increasing or s decreasing the volume of the drop, the advancing and receding contact angles were measured. The environmental chamber was purged with nitrogen during measurements of the contact angles to avoid contamination of the SAMs. All contact angles reported are the averages of at least 12 measurements at four different places on the sample.

6.1c Polarized Light Microscopy

Self-assembled monolayers supported on films of gold were paired and spaced apart by 2 or 25 μm spacers of mylar to form optical cells. A drop of SCB was heated into its isotropic phase, drawn between the surfaces of the optical cells by capillary action, and then cooled slowly into its nematic phases (~1° C./minute). A polarized light microscope (Olympus) was used to observe the optical textures of the liquid crystals at room temperature. See, Gupta, V. K. et al., 1996, *Langmuir,* 12, 2587.; Gupta, V. K., et al., 1996, *Chemistry of Materials,* 8, 1366. Conoscopic interference figures (Gupta, V. K. et al., 1996, *Langmuir,* 12, 2587; Gupta, V. K., et al., 1996, *Chemistry of Materials,* 8, 1366) were used to confirm the orientation of the direction of liquid crystals relative to the substrates in uniformly anchored samples.

6.2 Results 6.2a Single component SAMs Formed From Semi Fluorinated Thiols

The cartoons presented in FIG. 21 summarize the structure of SAMs formed from 1–3 and 5. All four compounds form densely packed and highly ordered SAMS. The semifluorinated chains are, in general, tilted away from the normal less than the chains in SAMs formed from alkanethiols; the semifluorinated chains appear to lie normal to the surface when they contain short ($—CH_{2\text{-}}$)$_n$ sequences (e.g., 1 and 2) The perfluorinated chains (outer region) within SAMs formed from 3 are tilted away from the normal more than the perfluorinated chains within SAMs formed from 1 and 2. The tilt of the aliphatic chains (inner region) in SAMs formed from 3 is less than the tilt of the aliphatic chains of 5 (Solution compositions of 1:1 and 3:1 were needed to form surface compositions of 1:1 for mixed SAMs formed from 1 and 2 and 1 and 3, respectively.]. Evidence for hydrogen bonding between C=O and NH within SAMs formed from 1 has been observed in IR spectra: the hydrogen bonding does not appear to alter the packing density of the chains on the surface.

Self-assembled monolayers formed from 1–3 were characterized by ellipsometry and contact angles of hexadecane, in addition to the IR measurements reported above. The ellipsometric thicknesses of SAMs formed from 1–3 were measured to be 17 Å, 15 Å and 26 Å, respectively, consistent with the formation of densely packed. The advancing and receding contact angles of hexadecane were 75–76° and 71–73°, respectively, for all samples with the exception of the advancing contact angle measured on SAMs formed from 3. All contact angles are consistent with presentation of $CF_3$ and $CF_2$ groups at the outer surface of each SAM. See, Ulman, A., 1991, *An Introduction to Ultrathin Organic Films: From Langmuir-Blodgett to Self Assembly* (San Diego, Calif.: Academic Press). The advancing contact angle of hexadecane measured on SAMs formed from 3 was 79°, suggesting that the outer regions of this SAM was structured differently than SAMs formed from 1 or 2 (see comment above regarding tilt of chains). Optical cells assembled with surfaces supporting SAMs formed from 3 did not fill by capillary action when 2μm-thick mylar was used to space apart the surfaces of the cells. Reported, therefore, are results for 3 with cells with surfaces spaced apart by 25 μm-thick mylar.

Optical textures of 5CB anchored on SAMs formed from 1–3 and 5 are shown in FIG. 22. Optical textures of 5CB anchored on SAMs formed from 6 have been published elsewhere and are similar to 5. See, Gupta, V. K., et al., 1996, *Langmuir,* 12,2587.; Gupta, V. K.; Miller, W. J.; Pike, C. L. et al., 1996, *Chemistry of Materials,* 8, 1366. The diffuse, meandering branches emerging from defects of strength ½ (two branches) within 5CB supported on SAMs formed from either 1 or 2 (FIG. 22a and 22b) are consistent with planar and azimuthally degenerate anchoring of 5CB. In contrast, the optical textures of SCB in contact with SAMs formed from 5 (FIG. 22e) have a grainy appearance with characteristic dimensions that are much smaller than observed with SAMs formed from either 1 and 2. Although meandering branches and ½ defects are not generally observed when SCB is anchored on SAMs formed from alkanethiols, measurements of the polar anchoring of SCB on SAMs formed from $CH_3(CH_2)_{11}SH$ (an alkanethiol that forms a SAM of similar thickness to 1 or 2) confirm planar anchoring. See, Gupta, V. K., et al., 1996, *Chemistry of Materials,* 8, 1366. Thus, the anchoring of 5CB on SAMs formed from semifluorinated thiols 1 and 2 and alkanethiols is planar. We note also that the spatial correlation of the azimuthal alignment of the director is greater on SAMs formed from semifluorinated thiols than SAMs formed from alkanethiols.

Figure 22A:
FIG. 22 displays optical textures of 5CB supported on SAMs from (a) 1: $CF_3(CF_2)_7CONH(CH_2)_2SH$; (b) 2: $CF_3(CF_2)_7(CH_2)_2SH$; (c) 3: $CF_3(CF_2)_7(CH_2)_{11}SH$ (all orthoscopic observation); (d) 3: $CF_3(CF_2)_7(CH_2)_{11}SH$ (conoscopic observation); (d) 5: $CH_3(CH_2)_{11}SH$ (orthoscopic). the rectangles in a and b enclose ½ defects. The lateral dimension of each orthoscopic figure is 550 μm.
Figure 22B:
Figure 22C:
Figure 22D:
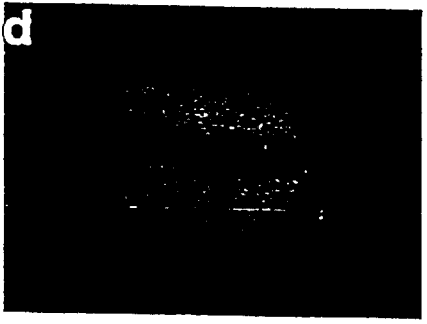
Figure 22E:
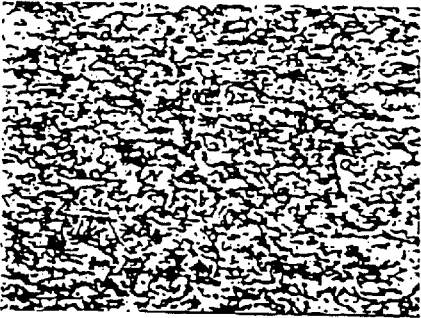
Figure 23A:
FIG. 23 displays cartoons of mixed SAMs formed by coadsorption of (a) 1: $CF_3(CF_2)_7CONH(CH_2)_2SH$ and 2: $CF_3(CF_2)_7(CH_2)_2SH$; ($\Delta t=2$ Å); (b) 1: $CF_3(CF_2)_7CONH(CH_2)_2SH$ and 3: $CF_3(CF_2)_7(CH_2)_{11}SH$; ($\Delta t=9$ Å) and (c) 4: $CH_3(CH_2)_9SH$ and 6: $CH_3(CH_2)_{15}SH$ ($\Delta t=9$ Å). These cartoons illustrate differences in the height of the chains within the mixed SAMs, and their relative degrees of conformational freedom.
Figure 23B:
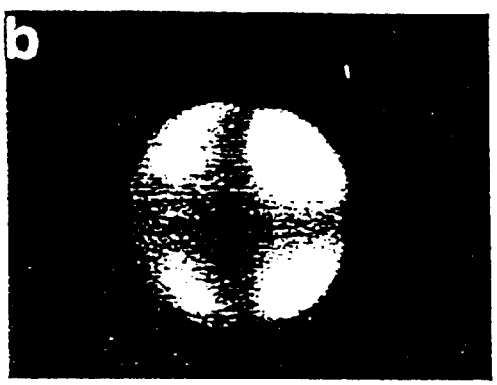
Figure 23C:
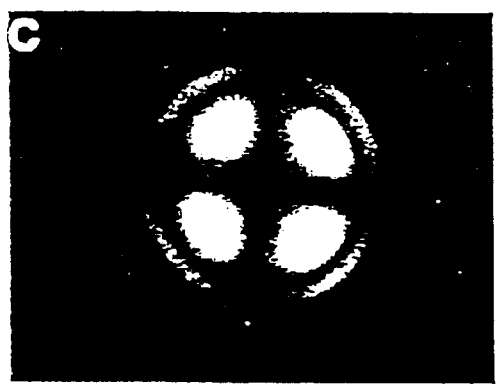
Figure 23D:
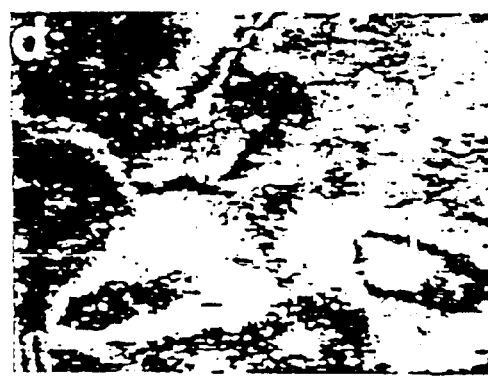

The optical textures of 5CB anchored on SAMs formed from 3 were different from 1 and 2. The textures observed on SAMs formed from 3 were not schlieren, but "marbled" (FIG. 22c). The characteristic dimension of the domains was larger than for SAMs formed from $CH_3(CH_2)_{15}SH$ (a monolayer of similar thickness to 3). In domains that were large enough to obtain a conoscopic image (FIG. 22d), the position of the interference fringes indicated a tilt of the optical axis (>>15°) away from the surface normal.

6.2b Mixed SAMs formed by Coadsorption of Semifluorinated Thiols.

Self-assembled monolayers were formed by coadsorption of either 1 and 2 or 1 and 3. The compositions of the mixed SAMs were confirmed to be 1:1 by XPS. FIG. 23 shows schematic illustrations of the mixed SAMs formed from the semifluorinated thiols, and a mixed SAM formed from 5 and 6. In the discussion that follows we use the variable Δt to denote the difference in the length of the short and long chains within mixed SAMs.

The contact angles were consistent with the presentation of $CF_2$ and $CF_3$ groups at the surface of the SAM except perhaps for the receding contact angle of SAMs formed from 1 and 3 (68°, see below).

The IR band corresponding to the amide II stretch (NH in-plane bending, 1545 cm$^{-1}$) measured using SAMs formed from 1 and 2 is similar to the position of the amide II stretch measured using SAMs formed from 1. This observation indicates hydrogen bonding takes place within the mixed SAM which, in turn, suggests incomplete mixing—and possibly islanding—of 1 and 2 within the mixed SAMs; hence, ideal mixing of species within the mixed SAM formed from 1 and 2 has not occurred. In contrast, the FTIR spectra measured with SAMs formed from 1 and 3 does show a shift of the amide II frequency to lower wave numbers, from which it can be inferred that there is true mixing of the two species within the SAM. The influence of the level of molecular mixing within the mixed SAMs on the anchoring or liquid crystals and (and contact angles) is unknown. The degree of mixedness could, however, account for the lower receding contact angles of hexadecane measured on SAMs formed from 1 and 3 (see above).

Figure 24A:
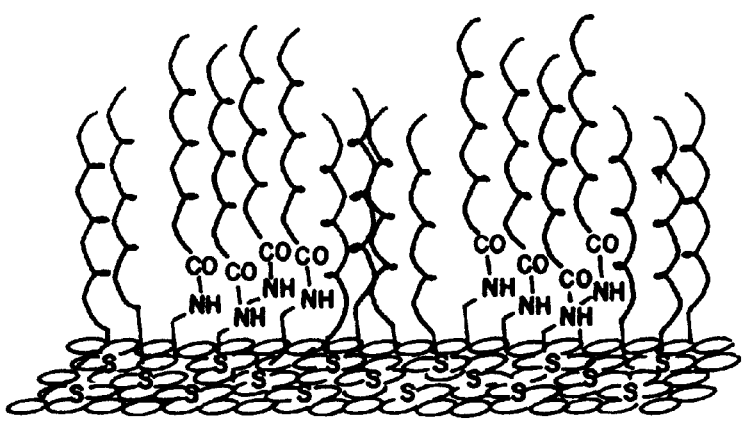
FIG. 24 displays optical textures of 5CB supported on SAMs formed by coadsorption of (a) 1: $CF_3(CF_2)_7CONH(CH_2)_2SH$ and 2: $CF_3(CF_2)_7(CH_2)_2SH$ (orthoscopic observation); (b) 1: $CF_3(CF_2)_7CONH(CH_2)_2SH$ and 2: $CF_3(CF_2)_7(CH_2)_2SH$ (conoscopic observation); (c) 1: $CF_3(CF_2)_7CONH(CH_2)_2SH$ and 3: $CF_3(CF_2)_7(CH_2)_{11}SH$ (conoscopic observation); and (d) 4: $CH_3(CH_2)_9SH$ and 5: $CH_3(CH_2)_{11}SH$ (orthoscopic observation). The rectangle in (d) encloses a ½ defect. The lateral dimension of each orthoscopic figure is 550 μm.
Figure 24B:
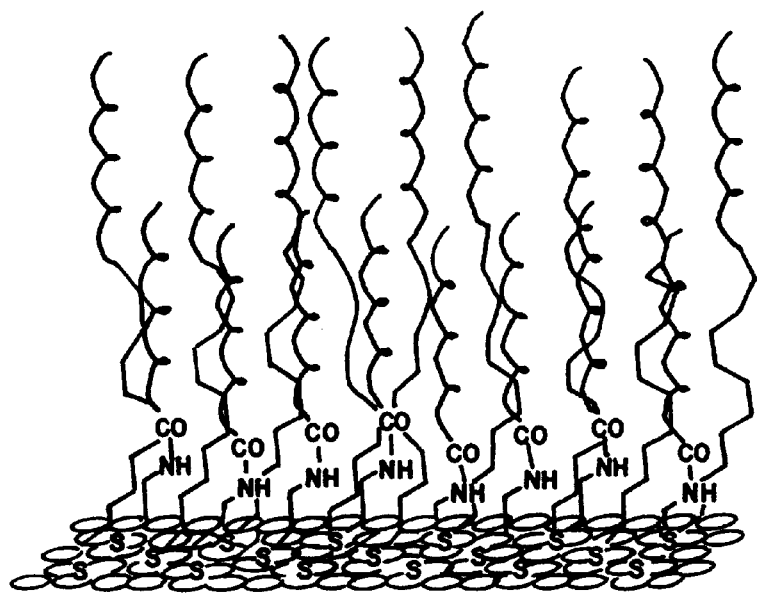
Figure 24C:
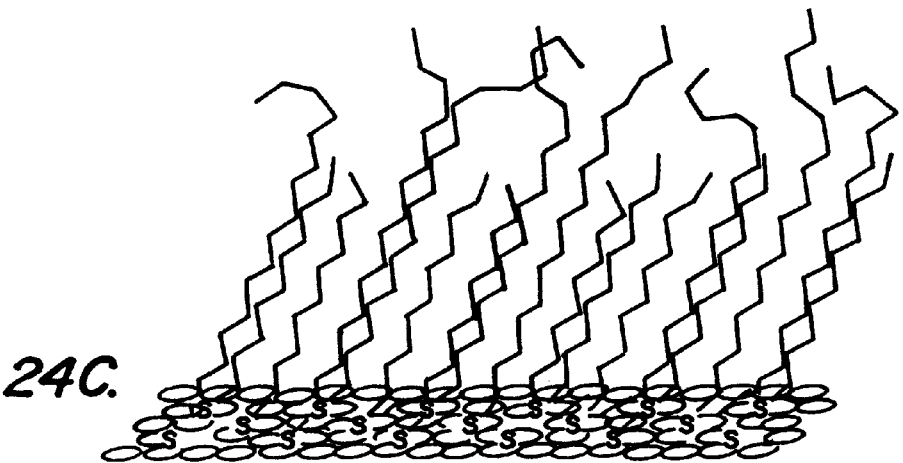

The optical textures of 5CB anchored on mixed SAMs formed from 1 and 2 ($\Delta_t$=2 Å) were schieren (FIG. 24a), although no defects with strength ½ could be found. Conoscopic images obtained from regions removed from defects showed interference fringes consistent with a tilt of the director (≈15°–20°) away from the surface normal (FIG. 24b). In contrast, mixed SAMs formed from 1 and 3 ($\Delta_t$=9 Å) caused homeotropic anchoring of 5CB (FIG. 24c). Mixed SAMs formed from 4 and 5 ($\Delta_t$=3 Å) cause near-planar anchoring (FIG. 24d) while past studies have shown that homeotropic anchoring is obtained on mixed SAMs formed from 4 and 6 ($\Delta_t$=9 Å).

What is claimed is:

1. A method of visually detecting an analyte-recognition moiety complex formed by an interaction between an analyte and a recognition moiety for said analyte by transducing said interaction to an organic mesogenic layer, said method comprising:
(a) interacting said analyte with a surface comprising said recognition moiety, thereby forming an analyte-recognition moiety complex, said surface comprising:
  (i) a substrate;
  (ii) a self-assembled organosulfur or oganosilane monolayer bound to substrate; and
  (iii) said recognition moiety bound to said self-assembled monolayer;
(b) contacting said analyte-recognition moiety complex with said organic mesogenic layer, thereby anchoring said organic mesogenic layer onto said self-assembled monolayer and causing at least a portion of a plurality of mesogens proximate to said recognition moiety to detectably switch from a first orientation to a second orientation, thereby transducing said interaction to said mesogenic layer, said transducing causing said mesogenic layer to register a visually detectable feature; and
(c) visually detecting said feature.

2. The method according to claim 1, wherein said self-assembled monolayer is formed from:

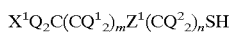

wherein,
$X^1$ is a member selected from the group consisting of H, halogen and recognition moieties;
Q, $Q^1$ and $Q^2$ are independently members selected from the group consisting of H and halogen;
$Z^1$ is a member selected from the group consisting of —$CQ_2$—, —$CQ^1{}_2$—, —C $Q^2{}_2$—, —O—, —S—, —$NR^4$—, —C(O)$NR^4$ and $R^4NC(O)$—,
in which;
$R^4$ is a member selected from the group consisting of H, alkyl, substituted alkyl, aryl, substituted aryl, heteroaryl and heterocyclic groups;
m is a number between 0 and 40; and
n is a number between 0 and 40.

3. The method according to claim 1, wherein said recognition moiety comprises a member selected from the group consisting of organic functional groups, metal chelates, organometallic compounds and combinations thereof.

4. The method according to claim 1, wherein said organic functional group is a member selected from the group consisting of amines, carboxylic acids, drugs, chelating agents, crown ethers, cyclodextrins and combinations thereof.

5. The method according to claim 1, wherein said recognition moiety is biotin.

6. The method according to claim 1, wherein said recognition moiety is a biomolecule.

7. The method according to claim 6, wherein said biomolecule is a member selected from the group consisting of antibodies, nucleic acids, peptides, enzymes and receptors.

8. The method according to claim 1, wherein said mesogenic layer comprises:

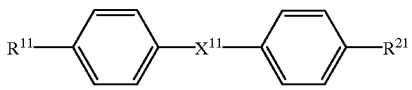

wherein,
$R^{11}$ and $R^{21}$ are members independently selected from the group consisting of alkyl groups, lower alkyl, substituted alkyl groups, aryl groups, acyl groups, halogens, hydroxy, cyano, amino, alkoxy, alkylamino, acylamino, thioamido, acyloxy, aryloxy, aryloxyalkyl, mercapto, thia, aza, oxo, both saturated and unsaturated cyclic hydrocarbons, heterocycles, arylalkyl, substituted aryl, alkylhalo, acylamino, mercapto, substituted arylalkyl, heteroaryl, heteroarylalkyl, substituted heteroaryl, substituted heteroarylalkyl, substituted heterocyclic and heterocyclicalkyl; and
$X^{11}$ is a member selected from the group consisting of —C═N—, —N═N(O)—, C═N(O)═N(O)—,— HC═CH—, —C≡C— and —OC(O)—

9. The method according to claim 1, wherein said visually detecting detects a change in reflectance, transmission, absorbance, dispersion, diffraction, polarization and combinations thereof, of light impinging on said plurality of mesogens.

10. The method according to claim 1, wherein said analyte is a member selected from the group consisting of vapors, gases and liquids.

11. The method according to claim 10, wherein said vapor is a member selected from the group consisting of vapors of a single compound and vapors of a mixture of compounds.

12. The method of claim 10, wherein said gas is a member selected from the group consisting of a single gaseous compound and mixtures of gaseous compounds.

13. The method of claim 10, wherein said liquid is a member selected from the group consisting of a single liquid compound, mixtures of liquid compounds, solutions of solid compounds and solutions of gaseous compounds.

14. The method according to claim 1, wherein said recognition moiety comprises a member selected from the group consisting of metal ions, metal-binding ligands, metal-ligand complexes, nucleic acids, peptides, cyclodextrins, acids, bases, antibodies, enzymes and combinations thereof.

15. The method according to claim 1, wherein from about 10 to about $10^8$ mesogens undergo said switching for each molecule of analyte interacting with said analyte.

16. The method according to claim 1, wherein from about $10^3$ to about $10^6$ mesogens undergo said switching.

17. The method according to claim 1, wherein said first orientation is a member selected from the group consisting of uniform, twisted, isotropic and nematic and said second orientation is a member selected from the group consisting of uniform, twisted, isotropic and nematic, with the proviso that said first orientation and said second orientation are different orientations.

18. The method according to claim 17, wherein said detecting is achieved by a method selected from the group consisting of visual observation, microscopy, spectrometry, electronic techniques and combinations thereof.

19. The method according to claim 18, wherein said microscopy is a member selected from the group consisting of light microscopy, polarized light microscopy, atomic force microscopy, scanning tunneling microscopy and combinations thereof.

20. The method according to claim 18, wherein said spectroscopic technique is a member selected from the group consisting of infrared spectroscopy, raman spectroscopy, x-ray spectroscopy, visible light spectroscopy, ultraviolet spectroscopy and combinations thereof.

21. The method according to claim 18, wherein said electronic technique is a member selected from the group consisting of surface plasmon resonance, ellipsometry, impedometric methods and combinations thereof.

* * * * *